United States Patent
Wada et al.

(10) Patent No.: US 9,766,216 B2
(45) Date of Patent: Sep. 19, 2017

(54) REDUCTION OF MIGRATION SHIFT ASSAY INTERFERENCE

(75) Inventors: H. Garrett Wada, Atherton, CA (US); Irina G. Kazakova, Los Gatos, CA (US); Yutaka Miki, Takarazuka (JP); Toshinari Ohashi, Amagasaki (JP); Futoshi Kanke, Midlothian, VA (US)

(73) Assignee: Wako Pure Chemical Industries, Ltd., Osaka (JP)

(*) Notice: Subject to any disclaimer, the term of this patent is extended or adjusted under 35 U.S.C. 154(b) by 702 days.

(21) Appl. No.: 10/821,657

(22) Filed: Apr. 8, 2004

(65) Prior Publication Data

US 2005/0170362 A1    Aug. 4, 2005

Related U.S. Application Data

(60) Provisional application No. 60/462,636, filed on Apr. 14, 2003, provisional application No. 60/500,177, filed on Sep. 4, 2003.

(51) Int. Cl.

| | |
|---|---|
| C12Q 1/68 | (2006.01) |
| G01N 30/86 | (2006.01) |
| G01N 33/53 | (2006.01) |
| G01N 33/538 | (2006.01) |
| G01N 33/561 | (2006.01) |
| B01L 3/00 | (2006.01) |
| G01N 30/02 | (2006.01) |
| G01N 30/34 | (2006.01) |

(52) U.S. Cl.
CPC .... *G01N 30/8644* (2013.01); *B01L 3/502753* (2013.01); *G01N 33/5306* (2013.01); *G01N 33/538* (2013.01); *G01N 33/561* (2013.01); *B01L 3/5027* (2013.01); *B01L 2300/0816* (2013.01); *B01L 2400/0415* (2013.01); *B01L 2400/0487* (2013.01); *G01N 30/02* (2013.01); *G01N 30/34* (2013.01)

(58) Field of Classification Search
CPC ............ C12Q 1/6834; C12Q 2565/629; C12Q 2565/125; G01N 33/6845; G01N 27/44773; B01L 3/502715; B01L 3/50273; B01L 2400/0421; B01L 2200/027; B01L 2300/069; B01L 2300/0883; B01L 3/5027; B01L 9/527

See application file for complete search history.

(56) References Cited

U.S. PATENT DOCUMENTS

| | | | |
|---|---|---|---|
| 5,284,558 A * | 2/1994 | Linhardt et al. | 204/451 |
| 5,571,680 A * | 11/1996 | Chen | 435/7.4 |
| 5,611,903 A * | 3/1997 | Janssens et al. | 204/454 |
| 5,630,924 A | 5/1997 | Fuchs et al. | |
| 5,948,227 A | 9/1999 | Dubrow | |
| 6,403,338 B1 | 6/2002 | Knapp et al. | |
| 6,537,433 B1 | 3/2003 | Bryning et al. | |
| 2001/0055591 A1 * | 12/2001 | Walston et al. | 424/94.63 |
| 2002/0079223 A1 * | 6/2002 | Williams et al. | 204/549 |
| 2002/0122793 A1 * | 9/2002 | Liu et al. | 424/94.61 |
| 2002/0128234 A1 | 9/2002 | Hubbell et al. | |
| 2004/0144649 A1 * | 7/2004 | Kawabata et al. | 204/451 |
| 2008/0273171 A1 * | 11/2008 | Huth et al. | 351/205 |

FOREIGN PATENT DOCUMENTS

| | | |
|---|---|---|
| EP | 1061370 A2 * | 12/2000 |
| EP | 1376126 A1 * | 1/2004 |
| EP | 1376126 A1 | 1/2004 |
| JP | WO 02/082083 A1 * | 10/2002 |
| WO | WO-02/27316 A2 | 4/2002 |
| WO | WO-02/082083 A1 | 10/2002 |
| WO | WO-03/015901 A1 | 2/2003 |

OTHER PUBLICATIONS

Bickel et al. Proceedings Natl Acad. Sci. 1992 vol. 89 p. 1001.*
Wolfe et al. Electrophoresis Mar. 23, 2002 vol. 23 p. 727.*
Kaniansky et al. Anal Chem 2000 vol. 72 p. 3596.*
Stathakis et al. Journal of Chromatography A 1998 vol. 817 p. 227.*
Stalcup et al. Anal Chem 1994 vol. 66 p. 3054.*
Fukkui et al. 1996 Nucleic acid Research vol. 24 p. 3962.*
Krylov et al. (Anal Chem 2000 vol. 72 p. 111R).*
Kaniansky et al. (Analytical chemistry 2000 vol. 72 p. 3596).*
Brown et al. (The journal of biological chemistry 1994 vol. 269 p. 26801).*
Xu et al. (Journal of Leukocyte Biology vol. 72 Aug. 2002 p. 410).*
Kautz et al. (Journal of American Chemistry Society 2001 vol. 123 p. 3159).*
Nilsson et al. (Journal of Virology Jul. 2001 vol. 75 p. 5796).*
Barme et al (Electrophoresis 1998 vol. 19 p. 1445).*
Gubitz et al. (Journal of Chromatography A 1997 vol. 792 p. 179).*
Zetterberg et al. (Journal of General Virology 2002 vol. 83 p. 2007).*

* cited by examiner

Primary Examiner — Katherine Salmon
(74) Attorney, Agent, or Firm — White & Case LLP

(57) ABSTRACT

This invention provides methods and compositions, e.g., to reduce interference from non-specific binding sample constituents in a migration shift assay. Interference due to non-specific binding of sample constituents to an affinity substance (e.g., an affinity molecule or a conjugate of an affinity molecule and a charged carrier molecule) is prevented by, e.g., binding the constituents to charged polymers such as heparin sulfate.

The present invention also provides methods to concentrate an analyte of interest with high concentration and to detect the analyte with high sensitivity, and further to optimize the reaction conditions for easily concentrating the analyte. Such objects of the present invention are attained, for example, by concentrating a complex of the analyte and a conjugate which is formed by contacting the analyte in a sample with an affinity molecule bound to a charged carrier molecule such as DNA.

61 Claims, 14 Drawing Sheets

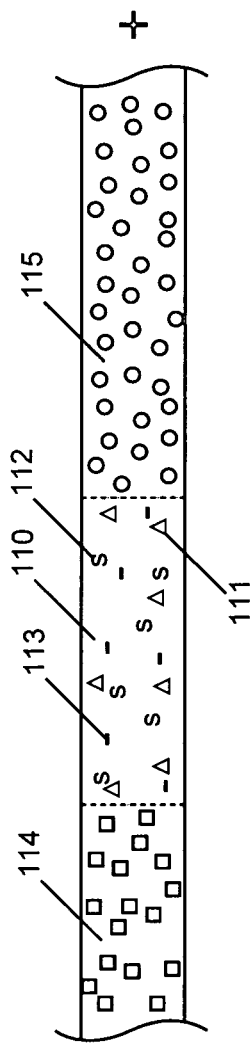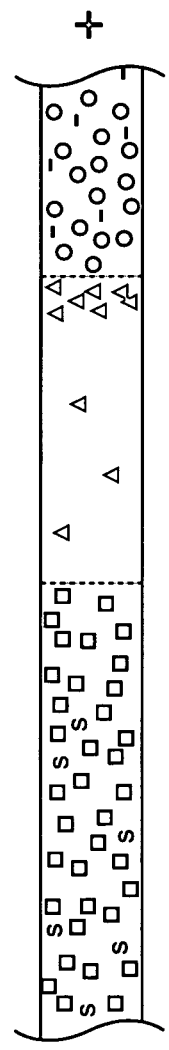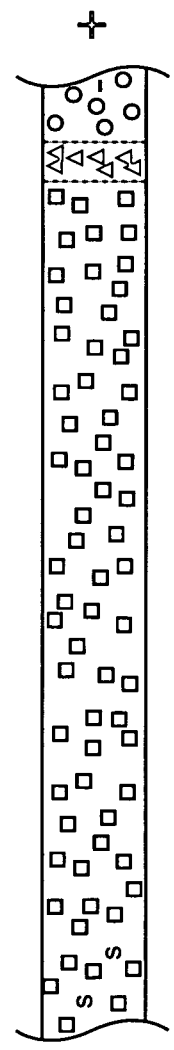

SEQUENCE LISTING

```
<160> NUMBER OF SEQ ID NOS: 3

<210> SEQ ID NO 1
<211> LENGTH: 26
<212> TYPE: DNA
<213> ORGANISM: Artificial
<220> FEATURE:
<223> OTHER INFORMATION: forward primer for PCR reaction

<400> SEQUENCE: 1
ggttagcaac ttactaccgg attttg                                      26

<210> SEQ ID NO 2
<211> LENGTH: 28
<212> TYPE: DNA
<213> ORGANISM: Artificial
<220> FEATURE:
<223> OTHER INFORMATION: reverse primer for PCR reaction

<400> SEQUENCE: 2
cctagcaaac tcggaagatt ttttcaga                                    28

<210> SEQ ID NO 3
<211> LENGTH: 28
<212> TYPE: DNA
<213> ORGANISM: Artificial
<220> FEATURE:
<223> OTHER INFORMATION: forward primer for PCR reaction

<400> SEQUENCE: 3
atctatgact gtacgccact gtccctag                                    28
```

REDUCTION OF MIGRATION SHIFT ASSAY INTERFERENCE

CROSS-REFERENCE TO RELATED APPLICATIONS

This patent application claims priority to U.S. provisional patent application Ser. Nos. 60/462,636, filed Apr. 14, 2003, and 60/500,177, filed Sep. 4, 2003, the entire contents of which are incorporated by reference herein.

FIELD OF THE INVENTION

This invention is in the field of methods and compositions to reduce interference in migration shift assays. The present invention provides, e.g., charged polymers to block sample constituents which interfere with a migration shift assay, and corresponding methods of using these polymers and compositions to reduce interference. This invention is also in the field of methods to highly concentrate a sample in a microfluidic device. The present invention also provides, e.g., charged carrier molecules and methods using such molecules to concentrate the sample.

BACKGROUND OF THE INVENTION

Migration shift assays are useful methods to detect and quantify associations between biomolecules. A change in the retention time of a molecule in an electrophoretic or chromatographic assay, for example, can indicate the presence of a binding molecule. Binding can be specific, such as in the case of antibody-antigen interactions, or non-specific, such as the ionic attraction of a positively charged molecule to a negatively charged polymer. Interference from non-specific interactions of sample constituents in a migration shift assay should be minimized to prevent biasing of assay results.

Migration shift analysis on separation media can take many forms. For example, a change in retention time of a free nucleic acid can be observed by size exclusion chromatography (SEC) when it is bound to a protein. The SEC resin can include pores large enough for the free nucleic acid to enter, but too small for the nucleic acid/protein pair to enter. The nucleic acid/protein pair flows quickly in the volume around the SEC resin while the free nucleic acid flows more slowly through the total volume inside and outside of the resin. There is a "shift" in retention time between the free nucleic acid and the nucleic acid/protein pair. In addition, the size of a detected nucleic acid/protein peak can be interpreted to quantify the amount of the protein in the original sample. The presence of an interfering sample constituent can invalidate the results of a shift detection or quantitative assay.

In another example of migration shift analysis, free nucleic acid and a nucleic acid/protein pair can be separated by capillary electrophoresis (CE) through a separation media of a sieving polymer or gel which restricts the migration of large molecules, but allows freer flow of small molecules. In CE, an electroosmotic buffer flow is created by a direct electric current through a capillary tube. When current is applied, positively charged ions, and their associated solvating water molecules, migrate toward the cathode, creating an electroosmotic flow. A sample can be transported by this flow through a sieving polymer separation media in the lumen of a capillary tube to separate sample molecules by size for detection of a migration shift. The larger nucleic acid/protein pair will be entangled and impeded more than the free nucleic acid and thus exit the media later. A fluorescence or absorbance detector, for example, can monitor elution from the capillary tube to detect timed peaks which can be plotted on a chart to measure the time difference or "migration shift" between elution of the free nucleic acid and the nucleic acid/protein pair.

Recently, significant progress has been made in the application of microfluidics-based technologies which utilize microscale channel devices in various fields, for example, analysis of DNA, RNA, protein and metabolites. Advantages of such microfluidic technologies include reduction of reagent volume, higher resolution, shorter operation time, and easier solution handling.

A problem arises with some complex samples, such as samples derived from a human body such as blood or cell lysates, which can contain interfering constituents that bind non-specifically to assay components. For example, when the specific binding interaction of interest is the binding of a transcription factor to a specific target DNA sequence, a non-specific binding sample constituent can interfere with detection of the migration shift measurement. The interfering constituent can bind to the target DNA resulting in an insoluble complex that will not migrate in the separation media. The interfering constituent can create noisy background or false positive peaks by binding to the target DNA. In any case, non-specific binding of the target DNA can reduce the sensitivity and/or accuracy of the migration shift analysis.

Non-specific binding has been a problem in studies of DNA binding proteins. This problem was addressed in Brehm, BBRC 63: 24-31, 1975, where an anion exchange resin (QAE-Sephadex) was used to adsorb negatively charged blood serum proteins while washing away positively charged proteins that could non-specifically bind to the negatively charged DNA molecule. Adsorbed proteins were eluted from the QAE-Sephadex then applied to DNA-cellulose.

Proteins that bound to the DNA cellulose were identified as DNA binding proteins. Although this technique may have washed away some positively charged proteins that would have bound non-specifically to the DNA-cellulose, some of the proteins washed away were probably unidentified DNA binding proteins.

Instead of removing all positively charged proteins before a DNA binding assay, polyanion blocking agents can be added to assay solutions to minimize non-specific binding. In Carthew, et al., Cell 43: 439-448, 1985, poly dIdC was added to running buffers of a DNA binding gel electrophoresis migration shift assay to reduce the effect of proteins that bind non-specifically to the DNA. In such a strategy, poly-dIdC can compete with the target DNA for the non-specific DNA binding molecules, thereby reducing non-specific binding interference while enhancing the migration shift signal of any specifically bound proteins. Theoretically, DNA binding proteins specific for the target DNA can be detected, even if they are positively charged, since they can bind stronger to the target DNA, having both electrostatic and specific binding affinities. Although this blocking technology provides one way to enhance detection of DNA binding proteins, it fails to describe methods to enhance detection of migration shifts resulting from other types of specific binding interactions.

Migration shifts can be observed in other interactions of affinity molecules with analytes. Migration shifts can be observed, for example, when an antibody binds to an antigen, or when a polysaccharide binds to a lectin. However, chromatography or electrophoresis of these molecules often provides broad and poorly resolved peaks due to multiple conformations and unstable charge density in these molecules. The diversity of possible affinity molecule/analyte pairs can also require development of a special migration shift assay for each pair. These problems can be avoided if the affinity molecule is linked to a carrier polymer that is highly resolved in assays under a standard set of conditions. An example of technology using a carrier/affinity molecule conjugate is described, e.g., in Japanese Patent Application number WO 02/082083, "Method for Electrophoresis", which is hereby incorporated by reference in its entirety. Although use of uniform carrier molecules for affinity molecules in migration shift analyses can improve resolution, a problem remains with interference due to non-specific binding.

A need therefore remains for methods to block the interference in migration shift assays, particularly in assays utilizing affinity molecule carriers. Migration shift assays of crude or complex samples can benefit from compositions, methods and apparatus that can block interference due to non-specific binding interactions with the migrating molecules. The present invention provides these and other features that will become apparent upon review of the following.

As mentioned above, migration shift assays provide very efficient separation and detection of the target analyte molecule (also referred to herein as the "objective substance" or "analyte of interest"). Moreover, the use of such migration shift assays in combination with microfluidic devices increases the efficacy of the assay. In order to increase the sensitivity of migration shift assays which use microfluidic devices, various methods for concentrating an objective substance (e.g., an analyte of interest) in a sample before applying the sample to a separation region of the device where the migration shift assay occurs, can be employed including, for example, (i) Field Amplification Sample Stacking (FASS), a method for concentrating the sample which utilizes the difference of electrical conductivities of a concentration domain and a separation domain (e.g., patent application Ser. No. 10/206,386 for "Microfluidic Methods, Devices and Systems for In Situ Material Concentration", Weiss, D. J., Saunders, K., Lunte, C. E. *Electrophoresis* 2001, 22, 59-65; Britz-McKibbin, P., Bebault, G. M., Chen, D. D. Y. *Anal Chem.* 2000, 72, 1729-1735, Ross, D., Locascio, L. E. *Anal Chem.* 2002, 71, 5137-5145, the entire contents of which are incorporated by reference herein.), (ii) Field Amplification Sample Injection (FASI), a method for concentrating the sample by inserting a minute plug of water between the concentration domain and the separation domain in the FASS (e.g., "Field amplified sample injection in high-performance capillary electrophoresis", Chien, R. L et al. *J. Chromatogr.* 1991, 559, 141-148, the entire contents of which are incorporated by reference herein), (iii) Isotachophoresis (ITP), a method for concentrating the sample which utilizes the difference of mobilities of ions in the domain sandwiched between a leading electrolyte solution and a trailing electrolyte solution (e.g., Everaerts, F. M., Geurts, M. Mikkers, F. E. P., Verheggen, T. P. E. M *J Chromatogr.* 1976, 119, 129-155; Mikkers, F. E. P., Everaerts, F. M., Peek, J. A. F. *J. Chromatogr.* 1979, 168, 293-315; and Mikkers, F. E. P., Everaerts, F. M., Peek, J. A. F. *J. Chromatogr.* 1979, 168, 317-332, Hirokawa, T, Okamoto, H. Ikuta, N., and Gas, B., "Optimization of Operational Modes for Transient Isotachophoresis Preconcentration-CZE," Analytical Sciences 2001, Vol. 17 Supplement i185, the disclosures of which are incorporated in their entirety by reference herein), (iv) Isoelectric Focusing (IF), a concentration/separation method which utilizes the difference of isoelectric points between the substances (e.g., "High performance isoelectric focusing using capillary electrophoresis instrumentation", Wehr T, et al. *Am. Biotechnol. Lab.* 1990, 8, 22, "Fast sand high-resolution analysis of human serum transferring by high-performance isoelectric focusing in capillaries", Kilar F. et al., *Electrophoresis* 1989, 10, 23-29, the entire contents of which are incorporated by reference herein.), and (v) Solid Phase Extraction (SPE), a concentration/separation method which utilizes a specific interaction between a solid phase (e.g., a solid phase with a bound adsorbent such as a receptor) and an objective substance to adsorb the objective substance to the solid phase (e.g., "Microchip-based purification of DNA from Biological Samples", Breadmore M. et al. *Anal. Chem.* 2003, 75, 1880-1886, the entire contents of which are incorporated by reference herein.).

However, when the objective substance is concentrated by using the above-mentioned conventional methods, unnecessary constituents (e.g., so-called "noise constituents" which interfere with the detection of the objective substance) are often concentrated simultaneously with the objective substance. As a result, when the sample concentrated by a conventional method is used as the sample for separation and detection, the detection sensitivity may be limited due to the increased background and noise levels. Furthermore, the conventional concentration methods which utilize electrophoresis such as FASS, ITP and IF cannot efficiently and highly concentrate an objective substance having a very large molecular weight or relatively low electrical charge.

That is, in the above-mentioned concentration methods, when the objective substance is assumed to be spherical, the mobility of the substance is shown by the following formula:

$$\mu_e = q/6 \ldots r$$

wherein $\mu_e$ is the electrophoretic mobility of a particular ion, q is the electrical charge of the ion, is the viscosity of a solution and r is a radius of the ion. As is clear from the above-mentioned formula, when the objective substance has a very large molecular weight and/or a small electrical charge, the electrophoretic mobility ($\mu_e$) of the objective substance is reduced because r in the formula becomes large and/or q in the formula becomes small. Accordingly, when using such conventional concentration methods, it is difficult to highly concentrate an objective substance which has a very large molecular weight and/or a small electrical charge in a short time. Additionally, in the conventional concentration methods, in order to concentrate the objective substance in the sample, optimization of the reaction condition is often difficult, particularly when the objective substance coexists in a complex sample with various unnecessary interfering constituents (e.g., noise constituents) other than the objective substance which tend to get concentrated along with the objective substance. This is especially true in the case of serum samples used in the clinical diagnostics field, which samples contain a variety of substances to be measured with wide varieties of molecular weight and electrical charge distributions. As mentioned above, the development of a method to concentrate the objective substance efficiently and highly to detect the objective substance with high sensitivity and without increasing the background and noise levels, especially in connection with the use of microfluidic devices, would be advantageous. The present invention provides such methods and other features that will become apparent upon review of the following.

BRIEF SUMMARY OF THE INVENTION

The present invention provides methods and compositions, e.g., to reduce sample constituent interference with separation of, e.g., a complex of an analyte and an affinity molecule from any free (e.g., unbound) affinity molecule, particularly separation of a complex of an analyte and a conjugate of an affinity molecule and a charged carrier molecule from any free (e.g., unbound) conjugate, which makes it possible to sensitively and specifically detect or identify the analyte of interest in a sample.

In one representative embodiment of a method of the present invention, a method of detecting or identifying an analyte of interest in a sample is disclosed which generally comprises: (i) contacting the sample containing the analyte with one or more affinity molecules to form a complex of the analyte and the affinity molecule(s), wherein the affinity molecule(s) has/have an affinity against the analyte; (ii) separating the complex and any unbound affinity molecule(s) in the presence of a charged polymer by using a separation channel in a microfluidic device comprising at least one separation channel having at least one microscale dimension of between about 0.1 and 500 microns; and (iii) detecting the complex to identify the presence of the analyte or to determine an amount of the analyte in the sample, wherein the charged polymer reduces interference with detecting.

In one embodiment of the invention, at least one affinity molecule is labeled with a detectable marker such as a fluorescent dye, a luminescent dye, a phosphorescent dye, a fluorescent protein, a luminescent protein or particle, a radioactive tracer, a chemiluminescent compound, a redox mediator, an electrogenic compound, an enzyme, a colloidal gold particle, or a silver particle. Alternatively, where the affinity molecule forms a conjugate with a charged carrier molecule, at least one of the affinity molecule and the charged carrier molecule forming the conjugate is generally labeled by a detectable marker.

Several other methods of determining or identifying an analyte of interest in a sample, such as a sample derived from a human body, are further disclosed. In one alternative representative embodiment, a method for determining or identifying an analyte in a sample derived from a living body is disclosed which generally comprises: (i) contacting the sample containing the analyte with one or more affinity molecules, at least one of which is labeled by a detectable marker, to form a complex containing the analyte and the affinity molecule(s) labeled by the detectable marker; (ii) separating the complex from any free affinity molecule labeled by the detectable marker which is not involved in forming the complex in a microfluidic channel of a microfluidic device in the presence of a charged polymer; (iii) measuring an amount of the separated complex or detecting a presence of the separated complex; and (iv) determining an amount of the analyte in the sample on the basis of the measured amount or identifying a presence of the analyte in the sample on the basis of the detected presence; wherein the affinity molecule has a property capable of binding to the analyte, and wherein when two or more affinity molecules are used, each affinity molecule has a property capable of binding with the analyte at a different site on the analyte from every other affinity molecule(s).

In another alternative embodiment, a method for determining or identifying an analyte in a sample derived from a living body is disclosed which generally comprises: (i) contacting the sample containing the analyte with one or more conjugates of an affinity molecule and a charged carrier molecule, wherein at least one of the one or more conjugates is labeled by a detectable marker, to form a complex containing the analyte and the conjugate labeled by the detectable marker; (ii) separating the complex from the conjugate labeled by the detectable marker which is not involved in the complex in a microfluidic channel of a microfluidic device in the presence of a charged polymer; (iii) measuring an amount of the separated complex or detecting a presence of the separated complex; and (iv) determining an amount of the analyte in the sample on the basis of the measured amount or identifying a presence of the analyte in the sample on the basis of the detected presence; wherein the affinity molecule in the conjugate has a property capable of binding to the analyte, and when two or more conjugates are used, each affinity molecule in the conjugate has a property capable of binding with the analyte at a different site on the analyte from every other affinity molecule, and wherein the charged carrier molecule has a property capable of causing a change in a separation (e.g., migration) property of the analyte by binding to the analyte through the affinity molecule to form a complex of the analyte, the affinity molecule and the charged carrier molecule.

In yet another alternative embodiment of the invention, a method for determining or identifying an analyte in a sample derived from a living body is disclosed which generally comprises: (i) contacting the sample containing the analyte with one or more affinity molecules and one or more conjugates of an affinity molecule and a charged carrier molecule, wherein either at least one of the affinity molecule or at least one of the conjugate is labeled by a detectable marker, to form a complex containing the analyte, the affinity molecule and the conjugate; (ii) separating the complex from any free affinity molecule labeled by the detectable marker or the conjugate labeled by the detectable marker which is not involved in forming the complex in a microfluidic channel of a microfluidic device in the presence of a charged polymer; (iii) measuring an amount of the separated complex or detecting a presence of the separated complex; and (iv) determining an amount of the analyte in the sample on the basis of the measured amount or identifying a presence of the analyte in the sample on the basis of the detected presence; wherein the affinity molecule and the affinity molecule in the conjugate have a property capable of binding to the analyte, and each affinity molecule has a property capable of binding with the analyte at a different site on the analyte from every other affinity molecule, and wherein the charged carrier molecule has a property capable of causing a change in a separation (e.g., migration) property of the analyte by binding to the analyte through the affinity molecule to form a complex of the analyte, the affinity molecule and the charged carrier molecule.

In still another alternative embodiment of the present invention, a method for determining an analyte in a sample derived from a living body is disclosed which generally comprises: (i) contacting the sample containing the analyte with the analyte labeled by a detectable marker or an analogue of the analyte labeled by a detectable marker and one or more affinity molecule to form a first complex of the analyte in the sample and the affinity molecule and a second complex of the labeled analyte or the labeled analogue and the affinity molecule; (ii) separating the second complex from any free labeled analyte or free labeled analogue which is not involved in forming the second complex in a microfluidic channel of a microfluidic device in the presence of a charged polymer; (iii) measuring an amount of the separated second complex or an amount of the separated free labeled analyte or the separated free labeled analogue; and (iv) determining an amount of the analyte in the sample on the basis of the measured amount; wherein the affinity molecule has a property capable of binding to the analyte in the sample and the labeled analyte or a property capable of binding to the analyte in the sample and the labeled analogue, and wherein when two or more affinity molecules are used, each affinity molecule has a property capable of binding with the analyte in the sample and the labeled analyte at a different site on the analyte in the sample and a different site on the labeled analyte from every other affinity molecule or each affinity molecule has a property capable of binding with the analyte in the sample and the labeled analogue at a different site on the analyte in the sample and a different site on the labeled analogue from every other affinity molecule.

Another embodiment of the invention discloses a method for determining an analyte in a sample derived from a living body, which generally comprises: (i) contacting the sample containing the analyte with the analyte labeled by a detectable marker or an analogue of the analyte labeled by a detectable marker and one or more conjugate of an affinity molecule and a charged carrier molecule to form a first complex of the analyte in the sample and the conjugate and a second complex of the labeled analyte or the labeled analogue and the conjugate; (ii) separating the second complex from any free labeled analyte or free labeled analogue which is not involved in forming the second complex in a microfluidic channel of a microfluidic device in the presence of a charged polymer; (iii) measuring an amount of the separated second complex or an amount of the separated free labeled analyte or the separated free labeled analogue; and (iv) determining an amount of the analyte in the sample on the basis of the measured amount; wherein the affinity molecule in the conjugate has a property capable of binding to the analyte in the sample and the labeled analyte or the analyte in the sample and the labeled analogue, and when two or more conjugates are used, each affinity molecule in the conjugate has a property capable of binding with the analyte in the sample and the labeled analyte at a different site on the analyte in the sample and a different site on the labeled analyte from every other affinity molecule, or each affinity molecule in the conjugate has a property capable of binding with the analyte in the sample and the labeled analogue at a different site on the analyte in the sample and a different site on the labeled analogue from every other affinity molecule, and wherein the charged carrier molecule has a property capable of causing a change in a separation (e.g., migration) property of the labeled analyte or the labeled analogue by binding to the labeled analyte or the labeled analogue through the affinity molecule to form a complex of the labeled analyte or the labeled analogue, the affinity molecule and the charged carrier molecule.

Further alternatively, a method for determining an analyte in a sample derived from a living body is disclosed which generally comprises: (i) contacting the sample containing the analyte with the analyte labeled by a detectable marker or an analogue of the analyte labeled by a detectable marker, one or more affinity molecule and one or more conjugate of an affinity molecule and a charged carrier molecule to form a first complex of the analyte in the sample, the affinity molecule and the conjugate and a second complex of the labeled analyte or the labeled analogue, the affinity molecule and the conjugate; (ii) separating the second complex from any free labeled analyte or free labeled analogue which is not involved in forming the second complex in a microfluidic channel of a microfluidic device in the presence of a charged polymer; (iii) measuring an amount of the separated second complex or an amount of the separated free labeled analyte or the separated free labeled analogue; and (iv) determining an amount of the analyte in the sample on the basis of the measured amount; wherein the affinity molecule and the affinity molecule in the conjugate have a property capable of binding to the analyte in the sample and the labeled analyte or the analyte in the sample and the labeled analogue, and each affinity molecule has a property capable of binding with the analyte in the sample and the labeled analyte at a different site on the analyte in the sample and a different site on the labeled analyte from every other affinity molecule or each affinity molecule has a property capable of binding with the analyte in the sample and the labeled analogue at a different site on each of the analyte in the sample and a different site on the labeled analogue from every other affinity molecule, and wherein the charged carrier molecule has a property capable of causing a change in a separation (e.g., migration) property of the labeled analyte or the labeled analogue by binding to the labeled analyte or the labeled analogue through the affinity molecule to form a complex of the labeled analyte or the labeled analogue, the affinity molecule and the charged carrier molecule.

In another alternative embodiment, a method for determining an analyte in a sample is disclosed which generally comprises: (i) contacting the sample containing the analyte with the analyte bound to a charged carrier molecule or an analogue of the analyte bound to a charged carrier molecule and one or more affinity molecule labeled by a detectable marker to form a first complex of the analyte bound to the charged carrier molecule or the analogue bound to a charged carrier molecule and the labeled affinity molecule and a second complex of the analyte in the sample and the labeled affinity molecule; (ii) separating the first complex from any second complex in a separation channel of a microfluidic device in the presence of a charged polymer; (iii) measuring an amount of the separated first complex or an amount of the second complex; and (iv) determining an amount of the analyte in the sample on the basis of the measured amount; wherein the affinity molecule has a property capable of binding to the analyte in the sample and the analyte bound to the charged carrier molecule or the analyte in the sample and the analogue bound to the charged carrier molecule, and wherein when two or more affinity molecules are used, each affinity molecule has a property capable of binding with the analyte in the sample and the analyte bound to the charged carrier molecule at a different site on the analyte in the sample and a different site on the analyte bound to the charged carrier molecule from every other affinity molecule or each affinity molecule has a property capable of binding with the analyte in the sample and the analogue bound to the charged carrier molecule at a different site on the analyte in the sample and a different site on the analogue bound to the charged carrier molecule from every other affinity molecule, and wherein the charged carrier molecule has a property capable of causing a change in a separation (e.g., migration) property of the first complex by binding to the analyte or the analogue to form a complex of the analyte or the analogue, the affinity molecule and the charged carrier molecule.

The present invention further describes compositions for separating a free conjugate of a charged carrier polymer and an affinity molecule, and a complex of an analyte in a sample and the conjugate, which in one embodiment comprises a separation media and a charged polymer. The present invention also provides methods to concentrate the objective substance, e.g., a complex of an analyte and a conjugate of an affinity molecule and a charged carrier molecule, particularly a complex of an analyte, an affinity substance and a conjugate of an affinity molecule and a charged carrier molecule, into high concentration prior to the separation and the detection by using a microfluidic device, which makes it possible to detect or identify the analyte of interest in a sample sensitively and specifically. The present invention further provides methods to optimize the reaction conditions for easily concentrating the objective substance.

In one representative embodiment of a method of the present invention, a method of concentrating an analyte of interest in a sample is disclosed which generally comprises: (i) contacting the sample containing the analyte with one or more of a conjugate of an affinity molecule and a charged carrier molecule to form a complex of the analyte and the conjugate; (ii) concentrating the complex by using a concentration channel in a microfluidic device comprising at least one concentration channel having at least one microscale dimension of between about 0.1 and 500 microns, wherein the charged carrier molecule causes a change in a migration property of the analyte by binding to the analyte through the affinity molecule to form a complex of the analyte, the affinity molecule and the charged carrier molecule.

The present invention further provides methods, e.g., to concentrate the objective substance, e.g., a complex of an analyte and a conjugate of an affinity molecule and a charged carrier molecule, particularly a complex of an analyte, an affinity substance and a conjugate of an affinity molecule and a charged carrier molecule and to reduce sample constituent interference with separation of the complex from any free (e.g., unbound) affinity molecule and/or free conjugate, which makes it possible to detect or identify the analyte of interest in a sample sensitively and specifically.

In one representative embodiment of a method of the present invention, a method of detecting or identifying an analyte of interest in a sample is disclosed which generally comprises: (i) contacting the sample containing the analyte with one or more a conjugate of an affinity molecule and a charged carrier molecule to form a complex of the analyte and the conjugate; (ii) concentrating the complex by using a concentration channel in a microfluidic device comprising at least one concentration channel having at least one microscale dimension of between about 0.1 and 500 microns; (iii) separating the complex and any unbound conjugate by using a separation channel in a microfluidic device comprising at least one separation channel having at least one microscale dimension of between about 0.1 and 500 microns; and (iv) detecting the complex to identify the presence of the analyte or to determine an amount of the analyte in the sample; wherein the charged polymer reduces interference with detecting; and wherein the charged carrier molecule causes a change in a migration property of the analyte by binding to the analyte through the affinity molecule to form a complex of the analyte, the affinity molecule and the charged carrier molecule.

BRIEF DESCRIPTION OF THE DRAWINGS

FIG. 11 is a schematic diagram of selective removal of sample constituents during ITP.

DETAILED DESCRIPTION

I. Migration Shift Assay

Figure 1A:
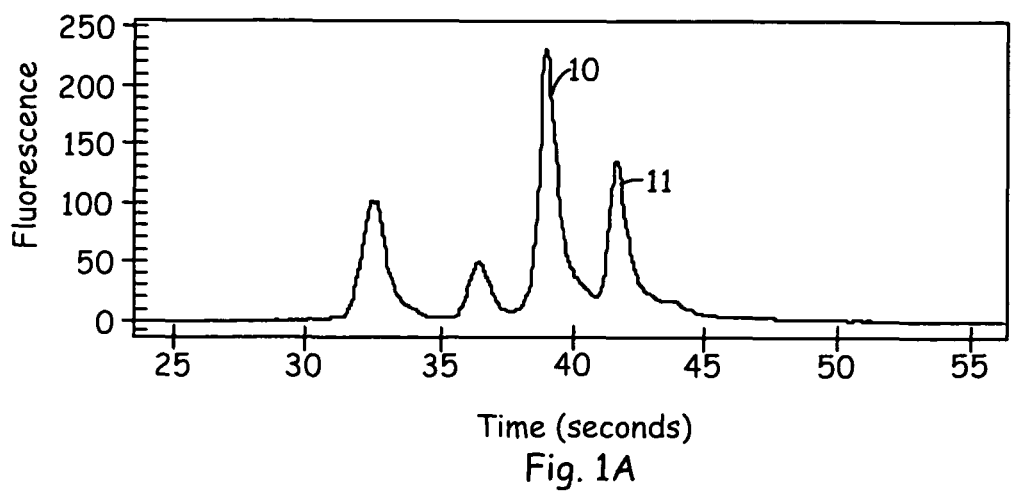
FIG. 1A shows a migration shift chart of an assay without interfering sample constituents.

The present invention can be applied to, e.g., so-called migration shift assays. In the present invention, migration shift assays are performed for the purpose of separating and analyzing an objective substance (e.g., an analyte of interest) and a substance having an affinity against the objective substance (e.g., an affinity molecule), which are contacted to form a complex of the objective substance and the affinity substance, after which the complex is separated from the affinity substance which is not involved in the complex (e.g., the free or unbound affinity substance) on the basis of a migration rate difference between them by using a microfluidic device, and the separated complex or the free affinity substance is analyzed. That is, migration shift assays of the invention include, e.g., detection of migration rate differences, e.g., between an affinity molecule and an affinity molecule/analyte complex, and in particular between a charged carrier molecule/affinity molecule conjugate with and without bound analyte using a microfluidic device.

As a migration shift assay, there can be exemplified the following methods: (i) a method, which generally comprises contacting the sample containing the analyte with the affinity molecule to form a complex containing the analyte and the affinity molecule, separating the complex from free affinity molecule which is not involved in forming the complex in a separation channel of a microfluidic device, measuring an amount of the separated complex or the free affinity molecule or detecting a presence of the separated complex, and determining an amount of the analyte in the sample on the basis of the measured amount or identifying a presence of the analyte in the sample on the basis of the detected presence; (ii) a method, which generally comprises contacting the sample containing the analyte with a conjugate of the affinity molecule and a charged carrier molecule to form a complex containing the analyte and the conjugate, separating the complex from free conjugate which is not involved in forming the complex in a separation channel of the microfluidic device, measuring an amount of the separated complex or the free conjugate or detecting a presence of the separated complex, and determining an amount of the analyte in the sample on the basis of the measured amount or identifying a presence of the analyte in the sample on the basis of the detected presence; (iii) a method, which generally comprises contacting the sample containing the analyte with (a) the affinity molecule and (b) the conjugate of the affinity molecule and the charged carrier molecule to form a complex containing the analyte, the affinity molecule and the conjugate, separating the complex from free affinity molecule and/or free conjugate which is not involved in forming the complex in a separation channel of a microfluidic device, measuring an amount of the separated complex or the free affinity molecule (and/or free conjugate) or detecting a presence of the separated complex, and determining an amount of the analyte in the sample on the basis of the measured amount or identifying a presence of the analyte in the sample on the basis of the detected presence; (iv) a method, which generally comprises contacting the sample containing the analyte with (a) an analyte labeled by a detectable marker and (b) the conjugate of the affinity molecule and the charged carrier molecule to form a complex containing the labeled analyte and the conjugate, separating the complex from free labeled analyte which is not involved in forming the complex in a separation channel of a microfluidic device, measuring an amount of the separated complex or the free labeled analyte, and determining an amount of the analyte in the sample on the basis of the measured amount or identifying a presence of the labeled analyte; and (v) a method, which generally comprises contacting the sample containing the analyte with (a) an analyte labeled by a charged carrier molecule and (b) one or more affinity molecules which have capabilities to bind both the analyte and the analyte bound to the charged carrier molecules and at least one of the affinity molecules is labeled by a detectable marker to form a complex of the analyte labeled with the charged carrier molecule and the affinity molecule labeled by a detectable marker, separating the complex from free form of the affinity molecule labeled by a detectable marker, measuring an amount of the separated complex or the free affinity molecule labeled by a detectable marker, and determining an amount of the analyte in the sample on the basis of the measured amount or identifying a presence of the labeled affinity molecule. In methods (iv) and (v), one can use a labeled analogue of the analyte as long as the analogue of the analyte has a capability to bind to the antibody.

II. Methods of the Invention

The present invention provides methods to reduce interference, e.g., in the above-described migration shift assays, and compositions which are used for practicing such methods. It is a characteristic of the present invention that in the above-mentioned migration shift assays the separation of the objective substance/affinity substance complex and the free affinity substance which is not involved in the complex is conducted in the presence of a charged polymer, and the separated complex or the free affinity substance is analyzed.

In the present invention, the term "objective substance" generally means a substance to be measured or identified (e.g., an analyte of interest in the sample), the term "affinity substance" generally means an affinity molecule and/or a conjugate of an affinity molecule and a charged carrier molecule, and the term "objective substance/affinity substance complex" means an analyte/affinity molecule complex, analyte/conjugate of an affinity molecule and a charged carrier molecule complex or an analyte/affinity molecule/conjugate of an affinity molecule and a charged carrier molecule complex.

If the sample contains an analyte which binds specifically to the affinity substance (e.g., the affinity molecule or a conjugate of the affinity molecule and charged carrier molecule), the complex will appear larger upon separation. This apparent size shift or "migration shift" indicates the presence of the analyte. However, in the presence of sample constituents that bind non-specifically to the affinity substance (e.g., especially where the affinity substance is conjugated with a carrier molecule), a false positive migration shift can be observed or an insoluble complex, which will not migrate in the separation channel, may be formed. The method of the invention provides charged polymers which can reduce the interference caused by the interfering constituents.

Figure 1B:
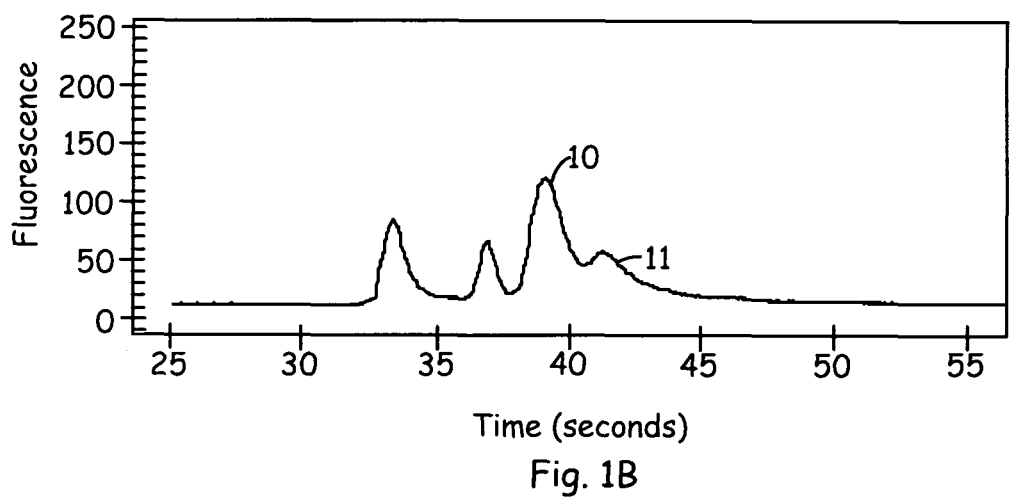
FIG. 1B shows the assay with added sample interfering constituents.
Figure 1C:
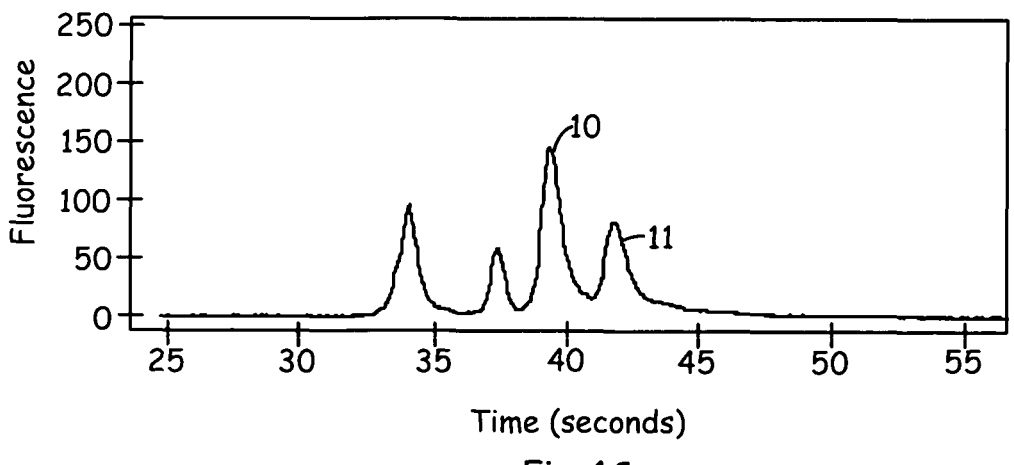
FIG. 1C shows reduction of interference by addition of a charged polymer.

For example, in a migration shift assay where the charged carrier molecule is DNA, serum constituents would interfere with the assay. Addition of a charged polymer such as heparin sulfate can reduce the interference. FIG. 1A shows an electropherogram chart of a migration shift in a separation media between conjugate peak 10 and conjugate/analyte complex peak 11. When serum is added to the sample, interfering constituents change the retention time, height, and area of complex peak 11, as shown in FIG. 1B. Addition of a charged polymer to the assay can reduce the interfering changes, as shown in FIG. 1C.

The method of the present invention can be carried out, for example, in the following way(s). That is, a sample containing the analyte is contacted with at least one affinity molecule to form a complex of the analyte and the affinity molecule, and the resulting complex is separated from any unbound affinity molecule in the presence of a charged polymer by using a separation channel in a microfluidic device comprising at least one separation channel having at least one microscale dimension of between about 0.1 and 500 microns. After that, it is possible to identify the presence of the analyte or to determine an amount of the analyte in the sample by detecting the complex.

A. Charged Polymer

The charged polymer of the invention can block interference with the migration shift assay by interacting with sample constituents that interfere with the assay. Without being bound to a particular theory, it is believed the charged polymer, having the same charge as the affinity molecule and/or charged carrier molecule in the conjugate, reduces interference in migration shift assays due to binding of oppositely charged interfering sample constituents that otherwise would have bound to the affinity molecule and/or charged carrier molecule in the conjugate. Charged polymer binding to interfering constituents can prevent, e.g., false positive migration shifts due to non-specific binding of constituents to the affinity molecule and/or the conjugate, or failed assays due to formation of an insoluble complex with the affinity molecule and/or the conjugate/constituent complexes.

The charged polymers of the invention can be, e.g., a polymer with a net charge (positive or negative) opposite to the sample constituent. The charged polymers having the same type (positive or negative) of net charge as the corresponding affinity substance (e.g., the affinity molecule and/or the conjugate) are preferable. The charged polymer of the invention may comprise a polyanionic polymer which can include, e.g., polysaccharides such as heparin, heparin sulfate, chondroitin sulfate, dextran sulfate, polytungstic acid, phosphotungstic acid, hyaluronic acid, dermatan sulfate and polyanethole sulfonic acid; polynucleotides such as DNA (e.g., plasmid DNA, calf thymus DNA, salmon sperm DNA, DNA coupled to cellulose, synthetic DNA, etc.) and RNA; polypeptides such as polyamino acid (e.g., polyaspartic acid, polyglutamic acid, etc.) and synthetic polypeptide; synthetic macromolecular compounds such as poly-dIdC, polyvinyl sulfate, polyacrylate; ceramics such as glass particles, colloidal glass, and glass milk; and complexes thereof. The charged polymer may also comprise a polycationic polymer which can include, e.g., polysaccharides such as chitosan and derivatives thereof; polypeptides such as polylysine, polyhistidine, polyarginine, protamine, histone, ornithine; synthetic macromolecular compounds such as polyallylamines, polyethyleneimine, polyvinylamine; polyamines such as spermine and spermidin; cationic lipids; ceramics; and complexes thereof. In a preferred embodiment of the invention, the charged polymer comprises anionic polysaccharides, preferably heparin sulfate.

In the present invention, the above-mentioned charged polymer may be used singly or in proper combination.

In order to separate the objective substance/affinity substance complex (e.g., analyte/affinity molecule complex, or analyte/conjugate complex or analyte/affinity molecule/conjugate complex) and the free affinity substance which is not involved in the complex (e.g., free affinity molecule or free conjugate) in the presence of the charged polymer, the separation is conducted in the presence of the charged polymer. For example, the charged polymer is preferably present in a separation channel of a microfluidic device comprising at least one separation channel. Specifically, it is preferable to add the charged polymer to the separation media packed in the separation channel. The presence of the charged polymer in the separation media can reduce carryover of interfering sample constituents between sample runs. Alternatively or additionally, the charged polymer may be present in the solution (e.g., water, a buffer such as tris-buffer, phosphate buffer, Veronal buffer, borate buffer, Good's buffer, SSC buffer, TBE buffer, TAE buffer, etc., used in hybridization assays, immunoassays, and the like) containing the objective substance and the objective substance/affinity substance complex, and the obtained solution containing the charged polymer, the objective substance and objective substance/affinity substance complex is then applied to the separation channel. Further, the charged polymer may be present in a solution to be used for applying a solution containing the objective substance and the objective substance/affinity substance complex to the microfluidic device, e.g., an eluent and a running buffer to be used in the separation (e.g., water, a buffer such as tris-buffer, phosphate buffer, Veronal buffer, borate buffer, Good's buffer, SSC buffer, TBE buffer, TAE buffer, etc., used in hybridization assays, immunoassays, and the like).

In the above-mentioned methods, in order that the charged polymer is present in the solution containing the objective substance and the objective substance/affinity substance complex, the following methods are exemplified. (i) the charged polymer is added to a sample containing the objective substance or a solution containing the sample, and the obtained solution containing the objective substance and the charged polymer is contacted with the affinity substance; (ii) the charged polymer is added to a solution containing the affinity substance, and the obtained solution containing the affinity substance and the charged polymer is contacted with the sample containing the objective substance or the solution containing the sample; (iii) the sample containing the objective substance or the solution containing the sample and the affinity substance are added to a solution containing the charged polymer; or (iv) the sample containing the objective substance or the solution containing the sample is contacted with the affinity substance and the obtained solution containing the objective substance and the objective substance/affinity substance complex is mixed with a solution containing the charged polymer. In the above-mentioned methods, the charged polymer can be added as a solution or as a dry powder.

In the present invention, by mixing the charged polymer with the sample before contact with the affinity substance (e.g., the affinity molecule, the conjugate of the affinity molecule and the charged carrier molecule), a kinetic advantage and/or precipitates of some interfering substances can be obtained. Such precipitates can be removed by filtration or centrifugation. Having both the charged polymer and the affinity substance (e.g., the affinity molecule, the conjugate of the affinity molecule and charged carrier molecule) in solution can allow the affinity substance to bind an analyte with a high affinity even if the analyte also binds non-specifically to the charged polymer. Therefore, the charged polymer is preferably present in at least the separation step (e.g., in the separation media), but it additionally and/or alternatively may be present in the contacting step of the sample containing the objective substance with the affinity substance (e.g., the affinity molecule and/or the conjugate) for forming the complex as well. In a preferred embodiment of the invention, the charged polymer is present in both the separation step (e.g., in the separation media) between the objective substance/affinity substance complex and the free affinity substance and the contacting step of the sample containing the objective substance and the affinity molecule for forming the complex to increase the recovery of objective substance existing in the sample. In the above-mentioned methods, in order that the charged polymer is present in the contacting step of the sample containing the objective substance with the affinity molecule for forming the complex, the following methods are exemplified: (i) The charged polymer is added to a sample containing the objective substance or a solution containing the sample, and the obtained solution containing the objective substance and the charged polymer is contacted with the affinity substance; (ii) the charged polymer is added to a solution containing the affinity substance, and the obtained solution containing the affinity substance and the charged polymer is contacted with the sample containing the objective substance or the solution containing the sample; and (iii) the sample containing the objective substance or the solution containing the sample and the affinity substance are added to a solution containing the charged polymer. In the above-mentioned methods, the charged polymer can be added as a solution or as a dry powder.

The sample solution can also contact the charged polymer on a solid support to adsorb interfering constituents before application to the separation media. The charged polymer can optionally be attached to a solid support for easy separation of the charged polymer from the sample. The solid support can be, e.g., any solid matrix compatible with adsorption interactions or linkage chemistries necessary to attach the particular charged polymer to the solid support.

The solid support can be, e.g., glass, plastic, cellulose, and the like. The solid support can be, e.g., in the form of beads, granules, porous surfaces, or flat surfaces. In many cases, solid supports with large surface to volume ratios can provide more efficient blocking of interfering constituents than those with lower ratios. The attaching of the charged polymer to the solid support may be conducted in a conventional manner usually used in this field, for example, as shown by Walsh M K et al. [J. Biochem. Biophys. Methods (2001) 47(3): 221-31].

In case of the charged polymer being present in the separation between the objective substance/affinity substance complex and the free affinity substance, the concentration of the charged polymer in the separation step (e.g., in the separation media within the separation channel) may be variable depending on the kind of the charged polymer to be used. Generally, the concentration of the charged polymer may be any concentration at which the presence of the charged polymer reduces the sample constituent interference with separation of an analyte/affinity molecule complex and any free affinity molecule, particularly separation of an analyte/conjugate of an affinity molecule and a charged carrier molecule complex and the free conjugate in a migration shift assay. The concentration of the charged polymer in the separation channel (e.g., within the separation media) is usually between about 0.01 to 5% (w/v), preferably about 0.05 to 2% (w/v), more preferably about 0.5 to 1.5% (w/v), for example about 1% (w/v).

In case that the charged polymer is present in the contacting step of the sample containing the objective substance with the affinity substance for forming the complex, the concentration of the charged polymer present in the solution (e.g., buffer) may be variable depending on the kind of the charged polymer to be used. Generally, the concentration of the charged polymer may be any concentration at which the presence of the charged polymer can reduce the interference without affecting any interaction between the analyte and the affinity substance. The concentration of the charged polymer in the solution containing the objective substance and the affinity substance (e.g., the affinity molecule, the conjugate of the affinity/carrier molecule) is usually between about 0.001 to 2% (w/v), for example between about 0.01 to 2% (w/v), preferably between about 0.001 to 1% (w/v), for example between about 0.02 to 1% (w/v), more preferably between about 0.001 to 0.05% (w/v), for example between about 0.025 to 0.5% (w/v), for example about 0.01% to 0.05% (w/v).

B. Sample

Samples of the present invention can be any material potentially containing an analyte of interest. Samples can include, e.g., a serum, a plasma, a whole blood, a tissue extract, a cell extract, a nuclear extract, a culture media, a microbial culture extract, members of a molecular library, a clinical sample, a sputum specimen, a stool specimen, a cerebral spinal fluid, a urine sample, a uro-genital swab, a throat swab, an environmental sample, and/or the like. Where the analyte is not free in solution, it can be released into a solution by grinding, lysis, extraction, filtering, centrifugation, and other appropriate techniques known in the art. In other words, samples to which the invention is applicable may be exemplified by the following: body fluids such as a serum, a plasma, a cerebrospinal fluid, a synovial fluid, a lymph fluid, etc., excretions such as urine, feces, etc., specimens of biological origin such as an expectoration, a purulent matter, a dermal exfoliation, etc., environmental specimens such as food, a beverage, tap water, seawater, water of lakes and marshes, river water, factory waste water, washings for semiconductors, washings after washing of medical instruments, etc., and their processed products reconstituted by dissolving in water or a buffer usually used in this field, for example, tris-buffer, phosphate buffer, Veronal buffer, borate buffer, Good's buffer, etc.

C. Analyte of Interest (Objective Substance)

Analytes can include, e.g., serum proteins such as peptide chains (e.g., C-peptide, angiotensin I, etc.), proteins [e.g., immunoglobulin A (IgA), immunoglobulin E (IgE), immunoglobulin G (IgG), immunoglobulin M (IgM), immunoglobulin D (IgD), $\beta_2$-microglobulin, albumin, their degradation products], ferritin, etc.; enzyme proteins such as amylase, alkaline phosphatase, γ-glutamyl-transferase, acidic phosphatase, lipase (e.g., pancreatic, gastric, etc.), creatine kinase (e.g., CK-1, CK-2, mCK, etc.), lactic acid dehydrogenase (e.g., LDH1 to LDH5, etc.), glutamic acid-oxaloacetic acid transaminase (e.g., AStm, ASTs, etc.), glutamic acid-pyruvic acid transaminase (e.g., ALtm, ALTs, etc.), choline esterase (e.g., ChE1 to ChE5, etc.), leucine aminopeptidase (e.g., C-LAP, AA, CAP, etc.), renin, protein kinase, tyrosine kinase, etc.; proteins or peptides or glycosyl antigens derived from microorganisms, for example, bacteria such as tubercule bacillus, pneumococci, *Corynebacterium diphteriae, Neisseria meningitidis*, gonococci, staphylococci, streptococci, intestinal bacteria, *Escherichia coli, Helicobacter pylori*, etc., viruses such as Rubella virus, Herpes virus, Hepatitis viruses, ATL virus, AIDS virus, influenza virus, *adenovirus, enterovirus, poliovirus*, EB virus, HAV, HBV, HCV, HIV, HTLV, etc., fungi such as *Candida, Cryptococcus*, etc., spirochaete such as *leptospira, Treponema pallidum*, etc., *chlamydia, mycoplasma*, and the like; a variety of allergens causing allergies such as asthma, allergic rhinitis, atopic dermatitis, etc., for example, house dust, mites such as *Dermatophagoides farinae, Dermatophagoides pteronyssinus*, etc., pollen of Japanese cedar, Japanese cypress, *Pasplum*, common ragweed, *Phleum pratense, Anthoxanthum odoratum*, rye, etc., animals such as cat, dog, crab, etc., food such as rice, albumen, etc., fungi, insects, wood, drugs, chemicals, and the like; lipids such as lipoproteins, etc.; proteases such as trypsin, plasmin, serine protease, etc.; tumor marker protein antigens such as alpha feto protein (AFP), prostate specific antigen (PSA), carcinoembryonic antigen (CEA), PGI, PGII, $\alpha^2$-macroglobulin, etc., sugar chains (e.g., CA19-9, PIVKA-II, CA125, tumor marker glycosyl antigen sugar chain such as sugar chain possessed by a material containing a special sugar chain produced by cancer cells, e.g., ABO glycosyl antigen, etc.); lectin (e.g., concanavalin A, lectin of Lens esculenta, lectin of *Phaseolus vulgaris*, stramonium lectin, wheat germ lectin, etc.); phospholipids (e.g., cardiolipin, etc.); lipopolysaccharides (e.g., endotoxin, etc.); chemical substances [for example, hormones such as steroid hormones, human chorionic gonadotropin (hCG), PTH, T3, T4, thyroid-stimulating hormone (TSH), insulin, luteinizing hormone (LH), FSH, prolactin, etc., environmental hormones such as tributyltin, nonylphenol, 4-octyl-phenol, di-n-butyl phthalate, dicyclohexyl phthalate, benzophenone, octachlorostyrene, di-2-ethylhexyl phthalate, etc.]; receptors (e.g., receptors for estrogen, THS, etc.); ligands (e.g., estrogen, TSH, etc.); nucleic acids; analytes conjugated to carrier proteins; analytes conjugated to nucleic acids and antibodies thereto. In this connection, the antibodies used in the present invention as an affinity molecule also include Fab, Fab' or F(ab')$_2$ fragments as degradation products produced by degradation with a proteinase such as papain or pepsin or by chemical degradation. The present invention is useful, for example, in measuring the following analytes; e.g., alpha feto protein, serum proteins, tumor markers, enzymes, hormones, HCG, TSH, FSH, LH, analytes conjugated to carrier proteins, analytes conjugated to nucleic acids, and the like.

D. Affinity Molecule

The affinity molecule (e.g., affinity substance) may be any one which has a specific affinity for the analyte of interest in the sample, and for example may be selected from the group consisting of an antibody, an Fab, F(ab')$_2$ or Fab' fragment of an antibody, an antibody variable region, a lectin, avidin, a receptor, an affinity peptide, an aptamer, and a DNA binding protein. The affinity molecules can have a specific affinity for ligands such as, e.g. virus particles, bacterial cells, proteins, peptides, carbohydrates, antigens, lipids, steroids, small chemicals, and so on, which, e.g., function as enzymes, antibodies, hormones, cytokines, structural components, signaling molecules, and ligands to a certain receptor, etc. and which are sometimes recognized as tumor markers, inflammation markers, and infectious disease markers. These include AFP, hCG, TSH, FSH, LH, interleukin, Fas ligand, CA19-9, CA125, PSA, HBsAg, anti-HIV antibody, T4, and/or like. Also they can include ligands conjugated to carrier proteins, ligands conjugated to nucleic acids, intracellular proteins, signaling molecules, and/or the like. The affinity molecule used in the invention includes, for example, those having a property capable of binding to the objective substance depending on a protein-protein interaction, a protein-chemical substance interaction, or a chemical substances-chemical substances interaction. Specifically, those binding based on an antigen-antibody interaction, a sugar chain-lectin interaction, an enzyme-inhibitor interaction, a protein-peptide chain interaction, a chromosome or nucleotide chain-nucleotide chain interaction, a nucleotide-ligand interaction or receptor-ligand interaction are included. When one of the substances in the above-mentioned pairs is the objective substance, the other is the affinity molecule. For example, when the objective substance is an antigen, the affinity molecule is an antibody, and when the objective substance is an antibody, the affinity molecule is an antigen (the same applied to the above other pairs). The typical examples of the affinity molecule are the same as the above-mentioned analytes.

Among them, it is preferable to use the following affinity molecule, e.g., an antibody, an Fab, F(ab')$_2$ or Fab' fragment, an antibody variable region, a lectin mentioned above, avidin, a receptor, an affinity peptide, an aptamer, and/or a DNA binding protein. In the present invention, the above-mentioned affinity molecule can be used singly or in proper combination. When two or more affinity molecules are used, each affinity molecule binds with the objective substance at a different site on the objective substance from every other affinity molecule. And when the affinity molecule is used in the competitive assay method by using the analyte labeled by the detectable marker or the analogue of the analyte labeled by the detectable marker, the affinity of the affinity molecule toward the analyte in the sample and the labeled analyte is preferably the same or the affinity of the affinity molecule toward the analyte in the sample and the labeled analogue is preferably the same.

In the above-mentioned methods of the present invention, the concentration of the affinity molecule may be variable depending on the detection limit of the objective substance. Generally, it is desirable to maintain the affinity molecule at a concentration higher than that at which the affinity molecule can bind completely to the analyte at a concentration corresponding to the defined detection limit in the reaction mixture. The concentration in the reaction mixture is preferably kept at 2-fold or more of the detection limit, more preferably at 5-fold or more. When two or more affinity molecules are used, the concentration of each affinity molecule is selected from the above-mentioned concentration range.

The affinity molecule used in the present invention is generally one which can be measured (e.g., detected) or labeled by a detectable marker by some conventional detection method. The use of a molecule having such a property will make it possible to measure an analyte in a sample. In the case where an analyte itself can be detected by some method (e.g., an enzyme or the like), or where an analyte can bind directly to a detectable marker without an affinity molecule, the analyte in the sample can be measured, even if the affinity molecule possesses no such detectable property described above. Examples of an analyte that can be detected by itself by some method are enzymes, dyes, fluorescent substances, luminescent substances, substances having absorption in the ultra-violet region (e.g., DNA), and the like. When two or more affinity molecules are used, it is not necessary for all affinity molecules to have such a detectable property.

Where the affinity molecule (or conjugate of an affinity molecule/carrier molecule) is labeled with a detectable marker, the detectable marker can include those used conventionally in the field of the present invention, for example, enzyme immunoassays (EIA), radioimmunoassays (RIA), fluorescence immunoassays (FIA), hybridization assays, and the like, may be used. Such a substance includes, for example, enzymes such as alkaline phosphatase (ALP), β-galactosidase (β-Gal), peroxidase (POD), microperoxidase, glucose oxidase (GOD), glucose-6-phosphate dehydrogenase (G6PDH), malic acid dehydrogenase, luciferase, etc.; pigments such as Coomassie Brilliant Blue R250, methyl orange, etc.; radioactive tracer such as $^{99m}$Tc, $^{131}$I, $^{125}$I, $^{14}$C, $^{3}$H, $^{32}$P, $^{35}$S, etc.; fluorescent dyes such as fluorescein, rhodamine, dansyl, fluorescamine, coumalin, naphthylamine, or their derivatives, cyanine type fluorescent dyes or oxazine type fluorescent dyes [e.g., Cy series dyes (Cy3, Cy5, and Cy5.5, etc.: Amersham Biosciences Corp.), Alexa Fluor series dyes (Alexa Fluor 647, 488, 594, etc.: Molecular Probes, Inc.), DY series dyes (DY-630, 633, 635, 640, 650, 655, 656, 780, 550, etc.: MoBiTec GmbH, Goettingen Germany), EVOblue™30 (MoBiTec GmbH, Goettingen Germany)]; rare earth fluorescent pigments [a combination of a rare earth metal, e.g., samarium (Sm), europium (Eu), terbium (Tb) or dysprosium (Dy), with a chelate compound, e.g., 4,4'-bis(1",1",1",2",2",3", 3"-heptafluoro-4",6"-hexadion-6"-yl)chlorosulfo-o-terphenyl (BHHCT), 4,7-bis (chlorosulfonyl)-1,10-phenanthroline-2,9-dicarboxylic acid (BCPDA), β-naphthyltrifluoroacetic acid (β-NTA), etc.]; nucleic acid-binding fluorescent pigment; a fluorescent protein; luminescent dyes such as luciferin, isoluminol, luminol, bis(2,4,6-trifluoro-phenyl)oxalate, etc., a luminescent protein or particle; UV absorbing substances such as phenol, naphthol, anthracene, or their derivatives; substances having a property of spin-labeling agent exemplified by compounds having an oxyl group such as 4-amino-2,2,6,6-tetramethyl-piperidin-1-oxyl, 3-amino-2,2,5,5-tetramethyl-pyrrolidin-1-oxyl, 2,6-di-t-butyl-α-(3,5-di-t-butyl-4-oxo-2,5-cyclohexa-dien-1-ylidene)-p-tolyloxy, a phosphorescent dye, a chemiluminescent compound, a redox mediator, an electrogenic compound, a colloidal gold particle, or a silver particle, etc.

The above-mentioned fluorescent pigment binding to a nucleic acid emits strong fluorescence depending on binding to the nucleic acid chain. Such a nucleic acid-binding fluorescent pigment includes, for example, so-called intercalator pigments which are incorporated between the bases of the nucleic acid chain [for example, acridine pigments such as acridine orange, ethidium compounds such as ethidium bromide, ethidium homodimer 1 (EthD-1), ethidium homodimer 2 (EthD-2), ethidium bromide monoazide (EMA), dihydroethidium, etc., iodide compounds such as propidium iodide, hexydium iodide, etc., 7-amino-actinomycin D (7-AAD), cyanine dimer pigments such as POPO-1, BOBO-1, YOYO-1, TOTO-1, JOJO-1, POPO-3, LOLO-1, BOBO-3, YOYO-3, TOTO-3, etc. (all are trade names of Molecular Probes); cyanine monomer pigments such as PO-PRO-1, BO-PRO-1, YO-PRO-1, TO-PRO-1, JO-PRO-1, PO-PRO-3, LO-PRO-1, BO-PRO-3, YO-PRO-3, TO-PRO-3, TO-PRO-5, etc. (all are trade names of Molecular Probes Inc., Eugene, Oreg.); SYTOX pigments such as SYBR Gold, SYBR Green I and SYBR Green II, SYTOX Green, SYTOX Blue, SYTOX Orange, etc. (all are trade names of Molecular Probes)]; those binding to a minor group of DNA double helix [for example, 4',6-diamino-2-phenylindole (DAPI: trade names of Molecular Probes), pentahydrate (bisbenzimide) (Hoechst 33258: trade names of Molecular Probes), trihydrochloride (Hoechst 33342: trade names of Molecular Probes), bisbenzimide pigment (Hoechst 34580: trade names of Molecular Probes), etc.]; those specifically binding to the sequence of adenine-thymine (A-T)[for example, acridine pigments such as 9-amino-6-chloro-2-methoxyacridine (ACMA), bis-(6-chloro-2-methoxy-9-acridinyl)spermine (acridine homo-dimer), etc.; for example, hydroxystilbamidine, etc.], and the like.

Labeling of an analyte or an affinity molecule by a detectable marker can be performed by any one of usual methods commonly used in the art, such as known labeling methods commonly employed in EIA, RIA, FIA, hybridization assays, or the like, which are known per se [e.g., Ikagaku Zikken Koza (Methods in Medical and Chemical Experiments) vol. 8, Edited by Y. Yamamura, 1st ed., Nakayama-Shoten, 1971; A Kawao, Illustrative Fluorescent Antibodies, 1st ed., Softscience Inc., 1983; Enzyme Immunoassay, Edited by E. Ishikawa, T. Kawai, and K. Miyai, 3rd ed., Igaku-Shoin, 1987; Moleculer Cloning: A Laboratory Manual, 2nd. ed., J. Sambrook, E. F. Fritsch, and T. Maniatis, Cold Spring Harbor Laboratory Press, Nucleic Acid Res. (1988) 16, 3671, Chu, B. C., et al., Nucleic Acid Res. (1986) 14, 6115, Jabloski, et al., Chemistry of Proteins and Cross-linking, Shan S. Wong, (1991) Published by CRC Press, EP 1088592 A2, EP 1061370 A2 and the like], and usual methods employing a reaction of avidin (or streptavidin) and biotin.

E. Contacting the Sample with an Affinity Molecule

In order to contact the sample containing the analyte with the affinity molecule, the contacting step is made to form a complex of the analyte and the affinity molecule. There is no limitation in terms of how such a complex may be produced. For example, a sample containing an analyte and an affinity molecule can be dissolved, dispersed or suspended, respectively, e.g., in water or buffers such as tris-buffer, phosphate buffer, Veronal buffer, borate buffer, Good's buffer, SSC buffer, TBE buffer, TAE buffer and the like to give liquid materials, and these liquid materials can be mixed and contacted with one another. Alternatively, the sample and affinity molecule may be dissolved, dispersed or suspended at once. In the case where a sample containing an analyte is a liquid, an affinity molecule can be directly mixed with the sample. If the sample containing an analyte is a liquid, as described above, it may not be dissolved, dispersed or suspended, e.g., in water or the buffers. In the above-mentioned method, a concentration of the buffer is selected from the range usually used in the field of the present invention.

In the method of the present invention, it is difficult to generally define the pH and the temperature for contacting the sample with the affinity molecule, in other words, for forming a complex of the analyte and the affinity molecule, since they depend on the properties of the analyte or the affinity molecule. However, as far as they do not disturb the formation of the complex, the condition may be chosen according to a conventional manner usually used in the field of the present invention, e.g., known EIA, RIA, FIA or hybridization assays. That is, the contact (e.g., formation) may be conducted usually at a pH between about 2 to 10, preferably at a pH between 5 to 9, and usually at a temperature of between 0 to 90° C., preferably between 5 to 40° C. The reaction may be conducted for a period of a few seconds to several hours depending to the respective properties of the analyte and the affinity molecule, since the reaction time required for formation of the complex is varied depending on their properties.

The contacting the sample containing the analyte with one or more conjugate can also be conducted in various ways. That is, (i) the sample and the conjugate are made to contact to form a complex of the analyte and the conjugate independently without using a microfluidic device, and then a solution containing the obtained complex is applied to the microfluidic device to concentrate the complex, or (ii) the sample and the conjugate are applied to the microfluidic device and the contacting the sample containing the analyte with one or more conjugate and the concentrating the obtained complex are performed consecutively in the microfluidic device.

It is preferable to perform the contacting step and the concentrating step consecutively and continuously, and it is more preferable to be performed by the method comprising contacting the sample containing the analyte with one or more conjugate of an affinity molecule and a charged carrier molecule to form a complex of the analyte and the conjugate in a channel fluidically connected to the concentration channel having at least one microscale dimension of between about 0.1 and 500 microns, and concentrating the complex by using a concentration technique in a microfluidic device comprising at least one concentration channel having at least one microscale dimension of between about 0.1 and 500 microns. In the methods mentioned above, the channel fluidically connected to the concentration channel may have the same characteristics (materials, shapes, etc.) as that of the separation channel described above.

F. Conjugate

In order to improve upon or raise the separation efficiency of the analyte/affinity molecule complex and the free affinity molecule, and analyze the analyte with sufficient accuracy, an affinity molecule bound to a charged carrier molecule, e.g., a conjugate of the affinity molecule and the charged carrier molecule, can be used in the above-mentioned method of the present invention. That is, a sample containing the analyte is contacted with an affinity molecule/charged carrier molecule conjugate to form a complex of the analyte and the conjugate, and the resulting complex is separated from any unbound conjugate in the presence of a charged polymer by using a separation channel in a microfluidic device comprising at least one separation channel. After that, it is possible to identify the presence of the analyte or to determine an amount of the analyte in the sample by detecting the complex.

When a conjugate of an affinity molecule (e.g., antibody) and a charged carrier molecule is used in the assay format, the charged carrier molecule (e.g., a charged polymer such as DNA or RNA) of the present invention can carry the affinity molecule, and any bound analyte, while providing high resolution and a detectable signal in a sizing assay. The charged carrier molecule in the conjugate provides, e.g., high resolution and sensitivity while the affinity molecule provides, e.g., specificity to the migration shift assays of the invention. The charged carrier molecule can have a high charge to mass ratio, and a minimum of conformational forms for high resolution on separation media. Using a charged carrier molecule can have many benefits in a migration shift assay.

In a non-competitive assay method, the charged carrier molecules of the present invention include a molecule which, by binding to the analyte through the affinity molecule to form a complex of the analyte, the affinity molecule and the charged carrier molecule, causes a change in a separation (e.g., migration) property of the analyte.

In a competitive assay method, the charged carrier molecules of the present invention are used by binding to the analyte or an analogue of the analyte, if necessary, through the affinity molecule. That is, an analyte or an analogue of the analyte bound to a charged carrier molecule can also be used to improve separation of a complex of the analyte and affinity molecule.

Improved separation by using the charged carrier molecules is beneficial in the case of separating, for example, the analyte, the analogue, the affinity molecule, the charged carrier molecule, the conjugate of the affinity molecule and the charged carrier molecule, a complex of the analyte (or the analogue) and the affinity molecule, the labeled analyte, the labeled analogue, the labeled affinity molecule, the labeled conjugate, a complex of the labeled analyte (or the labeled analogue) and affinity molecule, and/or a complex of the analyte (or the analogue) and the labeled affinity molecule. In other words, the charged carrier molecules of the present invention have a property capable of causing a change in a separation property of the analyte (or the analogue) and the affinity molecule (or a complex thereof) by binding to the analyte (or the analogue) to form a complex of the analyte (or the analogue), the affinity molecule and the charged carrier molecule, and separating the complex of the analyte (or the analogue), the affinity molecule and the charged carrier molecule from the above mentioned analyte (or the analogue) (e.g., one which does not contain both the analyte or the analogue and the charged carrier molecule) which is not involved in forming the complex of the analyte (or the analogue), the affinity molecule and the charged carrier molecule.

The charged carrier molecule may have a net positive charge or a net negative charge, and a charged carrier molecule having a net negative charge is preferable. The use of a charged carrier molecule having the same type (positive or negative) of net charge as the corresponding charged polymer is preferable.

The charged carrier molecules of the present invention having the above-mentioned character are chosen from e.g., inorganic metal oxides such as silica and alumina; metals such as gold, titanium, iron, and nickel; inorganic metal oxides and the like having functional groups introduced by silane coupling processes and the like; living things such as various microorganisms and eukaryotic cells; polysaccharides such as agarose, cellulose, insoluble dextran; synthetic macromolecular compounds such as polystyrene latex, styrene-butadiene copolymer, styrene-methacrylate copolymer, acrolein-ethylene glycol dimethacrylate copolymer, styrene-styrenesulfonate latex, polyacrylamide, polyglycidyl methacrylate, polyacrolein-coated particles, crosslinked polyacrylonitrile, acrylic or acrylic ester copolymer, acrylonitrile-butadiene, vinyl chloride-acrylic ester and polyvinyl acetate-acrylate; biological molecules such as erythrocyte, sugars, nucleotide chain (e.g., DNA, RNA), polypeptides or derivatives thereof (e.g., sulfonated polypeptides), proteins and lipids, and the like. A charged carrier molecule having a net negative charge is preferably a nucleotide chain (e.g., DNA, RNA) or a sulfonated polypeptide, more preferably DNA or RNA. A charged carrier molecule having a net positive charge is preferably a cationic polymer. In the present invention, an anionic molecule comprising a nucleotide chain (e.g., DNA, RNA) or a sulfonated polypeptide is most preferable. DNA is particularly suitable because of the stability of the molecule and the abundant synthesis and linkage chemistry experience in the art.

The nucleotide chain used in the present invention has nucleotide residues as basic units comprising purine bases or pyrimidine bases, pentose as a sugar portion, and phosphates. The respective nucleotides link at the 3' and 5' carbons of the sugar portion through the phosphates to form a chain polynucleotide, for example, RNA in which the sugar portion is ribose and/or DNA in which the sugar portion is deoxyribose. The nucleotide chain may be of single strand, double strand, or more. The nucleotide chain used in the invention may be prepared in a per se conventional manner, for example, chemical synthesis, a method for extraction and purification of the cells derived from microorganisms, insects, animals, plants, etc., a method using the above-mentioned cells into which has been introduced a suitable vector gene such as plasmid, phage, cosmid, etc., in which method the cells are incubated and the multiplied vector is extracted and purified, and a method utilizing a gene-multiplication technique such as PCR (Molecular Cloning, A Laboratory Manual, 2nd Edition, J. Sambrook, E. F. Fritsch, T. Maniatis, Cold Spring Harbor Laboratory Press, etc.). The resulting nucleotide chain is destroyed by chemical decomposition or with a nucleic acid-cleavage enzyme such as restriction enzymes and then optionally purified to form a nucleotide chain of the desired length. In the present invention, the above-mentioned charged carrier molecule may be used singly or in proper combination.

Any kinds of modified nucleotides which are known to enhance the stability of the nucleotide, for example, toward various nuclease activities, may be used to generate the charged carrier molecule. For example, a phosphorothioate analog of nucleotide, a nucleotide that contains a methylene group in the place of oxygen in the ribose ring, or a nucleotide which has a replacement of the 2'-sugar deoxy substituent with 2'-fluoro, 2'-O-methyl, 2-O-alkoxyl- and 2'-O-allyl modification can be used. Such modifications are listed, for example, in *Nucleic Acids Res.*, 1997, 25, 4429-4443, Susan M Freier, et al.

The charged carrier molecules can range in size, e.g., usually from about 0.6 kDa to 70000 kDa, preferably from about 3 kDa to 7000 kDa, more preferably from about 6 kDa to about 400 kDa. The size of the carrier molecule can be optimized depending, e.g., on the type of separation media, the resolution cut offs of the separation media, the size of the analyte, the size of the affinity molecule, etc., to provide useful sensitivity and resolution. Especially in the case of using the nucleotide chain as the charged carrier molecule, the length of the nucleotide chain may be usually between about 1 bp to 100000 bp, preferably between 5 bp to 10000 bp, more preferably between 10 bp to 1000 bp, most preferably between 10 bp to 500 bp, as far as the purpose of the invention can be attained. The nucleotide chain used in the invention may be modified properly with a suitable one within the scope of attaining the purpose of the invention.

In the present invention, the binding of the charged carrier molecule to the affinity molecule may be carried out in the same manner as labeling of the analyte or the affinity molecule by the detectable marker as mentioned above. For example, the binding of the charged carrier molecule to the affinity molecule may be carried out utilizing the respective functional groups of the affinity molecule and of the charged carrier molecule directly or through a linker [for example, sulfo-succinimidyl 4-(p-maleimidophenyl)butyrate (Sulfo-SMPB), sulfosuccinimidyl 4-(N-maleimidomethyl)cyclohexane-1-carboxylate (Sulfo-SMCC), N-(ε-maleimidocaproyloxy)succinimide (EMCS), N-hydroxysuccinimide ester (NHS), etc.]. The binding may be conducted in a conventional manner usually used in this field, for example, per se known labeling methods utilized in known EIA, RIA, FIA or hybridization assays [for example, Ikagaku Jikken Koza (Experimental Manual in Medical Chemistry), vol. 8, Edited by Yuichi Yamamura, First edition, Nakayama Shoten, 1971; Zusetu (Illustrative Description) Fluorescent Antibodies, Akira Kawao, First Edition, Soft Science, 1983; Enzyme Immunoassay, Eiji Ishikawa, Tadashi Kawai, Kiyoshi Miyai, 3rd Edition, Igaku-Shoin, 1987; Molecular Cloning, A Laboratory Manual, 2nd Edition, J. Sambrook, E. F. Fritsch, T. Maniatis, Cold Spring Harbor Laboratory Press, etc. EP 1088592 A2, EP 1061370 A2, and the like, or in a conventional method utilizing the reaction of avidin (or streptavidin) with biotin.

After preliminary introduction of a reactive functional group to the charged carrier molecule, the affinity molecule may be linked to the charged carrier molecule containing the reactive functional group in the above-mentioned binding method. Especially, in case of using a nucleotide chain as the charged carrier molecule, the introduction of a reactive functional group into the nucleotide chain may be conducted according to a per se known method including, for example, a method for introducing a reactive functional group using a compound having a reactive functional group in the 5' triphosphate group located at the terminal of the nucleic acid (e.g., a compound having an amino group such as N-trifluoroacetylaminoalkylamine, a compound having a thiol group such as cystamine, a compound having biotin such as N-biotinylaminoalkylamine, a compound having a maleimido group such as maleimidoalkylamine, etc.) in formation of a phosphoamidite bond in the presence of a condensing agent, e.g., 1-ethyl-3-(3-dimethyl-aminopropyl) carbodiimide (EDC), hydrochloride (WSC), etc. [Nucleic Acid Res. (1988) 16, 3671, Chu, B. C., et al.]; a method for introducing a reactive functional group using a compound having a reactive functional group in the 3' hydroxyl group located at the terminal of the nucleic acid (e.g., a compound having an amino group such as N-trifluoroacetylaminoalkylcarboxylic acid, a compound having biotin such as N-biotinylaminoalkyl-carboxylic acid, a compound having a maleimido group such as maleimidoalkylcarboxylic acid, etc.) in formation of an ester bond in the presence of a condensing agent, e.g., 1-ethyl-3-(3-dimethylaminopropyl) carbodiimide (EDC), hydrochloride (WSC), etc., or direct reaction with their active esters [Nucleic Acid Res. (1986) 14, 6115, Jabloski, et al.]; a method for introduction of an amino-reactive linker into a restriction enzyme-cleaved fragment at the terminal from which an amino-containing base (adenine, cytosine) is protruded as a single strand (sticky end, cohensive end) [Chemistry of Proteins and Crosslinking, Shan S. Wong, (1991) Published by CRC Press]; a method for incorporation of a nucleotide monomer having a reactive functional group in a restriction enzyme-cleaved fragment forming a single strand-protruded end with a blunting enzyme (T4 DNA polymerase, DNA blunting enzyme, etc.)(Molecular Cloning, A Laboratory Manual, 2nd Edition, J. Sambrook, E. F. Fritsch, T. Maniatis, Cold Spring Harbor Laboratory Press, etc.); a method for utilizing hybridization, wherein a reactive functional group is introduced into the 5' end of an oligonucleotide having a complimentary sequence for the single stranded portion of a restriction enzyme-cleaved fragment forming a single strand-protruded end to hybridize at the single strand-protruded end of the restriction enzyme-cleaved fragment (Molecular Cloning, A Laboratory Manual, 2nd Edition, J. Sambrook, E. F. Fritsch, T. Maniatis, Cold Spring Harbor Laboratory Press, etc.); a method utilizing PCR, wherein a PCR primer into which a reactive functional group has been introduced at the 5' end is used in PCR to yield as a PCR product a nucleotide chain into which a reactive functional group has been introduced at the 5' end (Molecular Cloning, A Laboratory Manual, 2nd Edition, J. Sambrook, E. F. Fritsch, T. Maniatis, Cold Spring Harbor Laboratory Press, etc.). Thus, a reactive functional group can be introduced into the terminal of nucleic acids. When a single strand nucleic acid is used, the nucleotide chain into which a reactive functional group has been introduced may also be prepared according to a method for hybridizing to the single strand nucleic acid an oligonucleotide having a sequence complimentary to the 5' end of the nucleotide chain and a reactive functional group introduced at 5' end (Molecular Cloning, A Laboratory Manual, 2nd Edition, J. Sambrook, E. F. Fritsch, T. Maniatis, Cold Spring Harbor Laboratory Press, etc.). The reactive functional group as mentioned above includes, for example, a hydroxy group, halogenated alkyl group, isothiocyanate group, avidin group, biotin group, carboxyl group, ketone group, maleimido group, active ester group, sulfonic acid halide group, carboxylic acid halide group, amino group, sulfonic acid group, piylidyldio group, aldehyde group, and the like.

When the number of the nucleotide chain to be bound to the affinity molecule is uneven, the number of the nucleotide chain existing in the formed complex becomes uneven to make separation of the complex non-specific. Therefore, it is preferable to unify the number of the nucleotide chain to be bound to the affinity molecule. In the same reason, it is appropriate for the number of the affinity molecule binding to one molecule of the nucleotide chain to be one molecule.

In the above-mentioned binding method, when the nucleotide chain has a functional group at both ends to which an affinity molecule can be bound, the nucleotide chain may preliminarily be cleaved enzymatically or chemically so that the reactive functional group is introduced at one end, and then allowed to bind to the affinity molecule. Alternatively, the nucleotide chain is allowed to bind to the affinity molecule so as to yield an intermediate to which the affinity molecule is bound at both ends, and the nucleotide chain binding to the intermediate is cleaved enzymatically or chemically to yield a product in which the affinity molecule is bound at one end of the nucleic acid.

Linkage chemistries can be used to attach the affinity molecule to the charged carrier molecule to form a conjugate of the invention. Linkage chemistries can be based on reactions with amino groups, thiols, carboxyl groups, imidazol groups, succinimide group, and the like. For example, a DNA carrier including nucleotides modified to have an amine group can be mixed in solution with the affinity molecule and a two-ended NHS linker, thereby cross linking the DNA to the affinity molecule. Other techniques for linking or associating or interacting an affinity molecule with a carrier molecule are disclosed in detail in Japanese Patent Application number WO 02/082083, "Method for Electrophoresis", which has been previously incorporated by reference in its entirety herein.

The conjugate of the affinity molecule and the charged carrier molecule to be used in the present invention is preferably a conjugate of at least one affinity molecule selected from the group consisting of an antibody, an Fab, F(ab')$_2$ or Fab' fragment, an antibody variable region, a lectin, avidin, a receptor, an affinity peptide, an aptamer and a DNA binding protein and at least one charged carrier molecule selected from group consisting of a nucleotide chain (e.g., DNA, RNA), cationic polymers and a sulfonated polypeptide. A conjugate of at least one affinity molecule selected from the group consisting of an antibody, an Fab, F(ab')$_2$ or Fab' fragment, an antibody variable region and an affinity peptide and at least one charged carrier molecule selected from the group consisting of a nucleotide chain (e.g., DNA, RNA) and a sulfonated polypeptide is more preferable, and further a conjugate of at least one affinity molecule selected from an antibody, an Fab or Fab' fragment and a nucleotide chain, particularly DNA as a charged carrier molecule is most preferable.

In the present invention, the above-mentioned conjugate can be used singly or in proper combination. When two or more conjugates are used, each affinity molecule in the conjugate binds with the objective substance at a different site on the objective substance from every other affinity molecule.

In the above-mentioned methods, it is difficult to generally define the concentration of the conjugate because it is variable depending on the detection limit of the objective substance. However, it is desirable to maintain the conjugate at a concentration higher than that at which the conjugate can bind completely to the analyte at a concentration corresponding to the defined detection limit in the reaction mixture. The concentration in the reaction mixture is preferably kept at 2-fold or more of the detection limit, more preferably at 5-fold or more. When two or more conjugates are used, the concentration of each conjugate is selected from the above-mentioned concentration range.

Such a conjugate is generally one which can be measured (e.g., detected) or labeled by a detectable marker by some method. That is, at least one of the affinity molecule and the charged carrier molecule in the conjugate is generally one which can be measured or labeled by a detectable marker by some method. The use of a conjugate having such a property will make it easy to measure an analyte in a sample. In the case where an analyte itself can be detected by some method (e.g., an enzyme or the like), or where an analyte can bind directly to a detectable marker without a conjugate, the analyte in the sample can be measured, even if the conjugate possesses no such detectable property described above. When two or more conjugates are used, it is not necessary for all conjugates to have such a property.

The detectable marker is as described above, and the labeling of the conjugate, e.g., the affinity molecule and/or the charged carrier molecule by the detectable marker may be carried out in the same manner as the labeling of the analyte or the affinity molecule by the detectable marker or the binding of the charged carrier molecule to the affinity molecule as mentioned above.

Especially, in case of the conjugate having the nucleotide chain as the charged carrier molecule, the marker may be bound directly to the nucleotide chain or through a linker [e.g., Sulfo-SMPB, Sulfo-SMCC, EMCS, NHS, etc.] or a nucleic acid (that is different from the nucleotide chain to be labeled, attached to the affinity molecule; hereinafter abbreviated to as "linker nucleotide chain"), peptide, protein, sugar, and the like (hereinafter abbreviated to as "linker substance"). When the nucleotide chain is bound to the marker through a linker substance, the binding of the nucleotide chain to the linker substance or the binding of the linker substance to the marker may be conducted in the same manner as in binding the nucleotide chain to the affinity molecule or in labeling the conjugate with the marker.

Alternately, linker chemistries can be used to covalently attach detectable markers to the polymer. For example, DNA as a charged carrier molecule can be synthesized using modified nucleotides which include linkers, such as an aliphatic chain with an N-hydroxysuccinimide ester (NHS) end group. A detectable marker, such as fluorescein amine, can become covalently attached to the polymer after a nucleophilic attack by the NHS on the marker amine group. Optionally, the modified nucleotide can include a linker reactive group, such as an amine, that can be attacked by a linker group attached to the marker. Other techniques for labeling or linking or associating or interacting a conjugate with a detectable marker are disclosed in detail in Japanese Patent Application number WO 02/082083, "Method for Electrophoresis", which has been previously incorporated by reference in its entirety herein.

In carrying out the labeling of the nucleotide chain with the marker through a linker substance, a linker substance preliminarily labeled with the marker may be bound to the nucleotide chain, or alternatively the linker substance may be bound to the nucleotide chain, followed by linkage with the marker, or the nucleotide chain, the linker substance and the marker are allowed to bind all at once. Moreover, in the present invention, the labeling of the nucleotide chain with the marker may be conducted before or at the same time as or after formation of the complex of the analyte/conjugate (nucleotide chain)/marker according to the marker to be used. There is no limitation for this modification. Particularly, it is preferred to bind the nucleotide chain to the linker substance preliminarily labeled with the marker.

For example, biotin is bound to a nucleotide chain and then to avidin (or streptavidin) preliminarily labeled with a marker. Thus, the nucleotide chain can easily be labeled under control of the amount of the marker. In another case, for example, biotin is first bound to a nucleotide chain and then to a linker substance (for example, linker nucleotide chain, etc.) labeled with a marker preliminarily bound to biotin through avidin (or streptavidin). Thus, the nucleotide chain can easily be labeled under control of the amount of the marker. Moreover, since one molecule of avidin (or streptavidin) can make 4 molecules of biotin bind, it is possible to make 3 molecules of the labeled linker bind to raise the sensitivity of measurement.

Use of a fluorescent pigment binding to a nucleic acid as a marker may be carried out as follows. According to a conventional manner (e.g., a method as described in the Handbook of Fluorescent Probe and Research Chemicals, 7th edition, Chapter 8; Molecular Probes Inc.), a marker is made to contact with a nucleotide chain [including the nucleotide chain in a charged carrier molecule (a nucleotide chain)/affinity molecule conjugate or a complex of an analyte and a charged carrier molecule/affinity molecule conjugate] in a buffer solution usually used in the field of hybridization assays or immunoassays, for example, water or tris-buffer, phosphate buffer, Veronal buffer, borate buffer, Good's buffer, SSC buffer, TBE buffer, TAE buffer, etc., at a suitable temperature for a suitable period of time. In the above-mentioned method, the contact of the nucleotide chain with the marker may be carried out by dissolving or dispersing or suspending the nucleotide chain, a sample containing the analyte, the charged carrier molecule (the nucleotide chain)/affinity molecule conjugate, the marker, the complex of the charged carrier molecule (the nucleotide chain)/affinity molecule conjugate and the marker, etc., directly in water or a buffer as mentioned above, or by dissolving or dispersing or suspending the respective components in water or a buffer as mentioned above to give liquid products, followed by mixing them so as to contact them with each other.

In the present invention, the step of contacting the sample containing the analyte with the conjugate of the charged carrier molecule and the affinity molecule may be carried out in the same manner as contacting the sample containing the analyte with the affinity molecule as mentioned above. The reaction conditions (e.g., pH, temperature, reaction time, etc.) are the same as for the above-mentioned condition of contacting the sample and the affinity molecule.

G. Use of Affinity Molecule and Conjugate

In order to improve upon or raise the separation efficiency of the analyte/affinity molecule complex and the free affinity molecule further and to provide higher resolution of analyte detection, both an affinity molecule and an affinity molecule bound to a charged carrier molecule, e.g., a conjugate of the affinity molecule and the charged carrier molecule, can be used in the above-mentioned method of the present invention. That is, a sample containing the analyte is contacted with an affinity molecule and an affinity molecule/charged carrier molecule conjugate to form a complex of the analyte, the affinity molecule and the conjugate, and the resulting complex is separated from any unbound affinity molecule and/or conjugate in the presence of a charged polymer by using a separation channel in a microfluidic device comprising at least one separation channel. After that, it is possible to identify the presence of the analyte or to determine an amount of the analyte in the sample by detecting the complex.

In the present invention, two or more affinity molecules and two or more conjugates can be used. In this case, each affinity molecule (including the affinity molecule in each conjugate) binds with the objective substance at a different site on the objective substance from every other affinity molecule.

In case of using both the affinity molecule and the conjugate, at least one of the affinity molecule and the conjugate is generally one which can be measured (e.g., detected) or labeled by a detectable marker by some conventional method. The use of an affinity molecule or a conjugate having such a property will make it is easy to measure an analyte in a sample. In the case where an analyte itself can be detected by some method (e.g., an enzyme or the like), or where an analyte can bind directly to a detectable marker without an affinity molecule or a conjugate, the analyte in the sample can be measured, even if the affinity molecule and the conjugate possess no such detectable property described above. When two or more affinity molecules or two or more conjugates are used, it is not necessary for all affinity molecules or all conjugates to have such a property. In the above-mentioned method, a detectable marker, a labeling of an affinity molecule or a conjugate by the detectable marker, etc. are as described above. There is no limitation as far as how to contact the sample containing the analyte with the affinity molecule and the conjugate to form a complex of the analyte, the affinity molecule and the conjugate. For example, a sample containing an analyte, an affinity molecule and a conjugate can be dissolved, dispersed or suspended, respectively, e.g., in water or buffers such as tris-buffer, phosphate buffer, Veronal buffer, borate buffer, Good's buffer, SSC buffer, TBE buffer, TAE buffer and the like to give liquid materials, and these liquid materials can be mixed and contacted with one another. Alternatively, the sample, affinity molecule and conjugate may be dissolved, dispersed or suspended together at once. In the case where a sample containing an analyte is liquid, an affinity molecule and/or a conjugate can be directly mixed with the sample. If the sample containing an analyte is liquid, as described above, it may not be dissolved, dispersed or suspended, e.g., in water or the buffers.

In the above-mentioned method, a concentration of the buffer is selected from the range usually used in this field. The concentration of the affinity molecule and the conjugate in the step of contacting the sample with the affinity molecule and the conjugate is as mentioned above. The reaction conditions (e.g., pH, temperature, reaction time, etc.) are the same as the above-mentioned condition of contacting the sample and the affinity molecule.

H. Separating Procedure

The resulting complex of the objective substance and the affinity substance (e.g., the analyte/affinity molecule complex, the analyte/conjugate complex or the analyte/affinity molecule/conjugate complex) is separated from the free affinity substance not involved in the formation of the complex (e.g., the affinity molecule and/or the conjugate). A separation method in which the complex and the free affinity substance are separable based on the difference in the migration rate of them can be applied. In this separation, for example, a conventional method used in this field, a so-called B/F separation procedure can be used. Typical examples are an electrical separation utilizing electricity such as electrophoresis (e.g., isoelectric focusing, SDS-polyacrylamide electrophoresis, agarose gel electrophoresis, acrylamide electrophoresis), dielectrophoresis, etc., column analysis (e.g., gel filtration column analysis, ion-exchange column analysis, affinity column analysis), mass spectrometric analysis, adsorption, micellar electrokinetic chromatography (MEKC) and the like. In particular, an electrical separation including electrophoresis or dielectrophoresis such as isoelectric focusing, SDS-polyacrylamide electrophoresis, agarose gel electrophoresis, acrylamide electrophoresis, etc., may preferably be used. More particularly, it is preferable to use capillary electrophoresis or dielectrophoresis since they can be conducted in an efficient cooling condition and under high voltage in high separation efficiency.

In addition, particularly when using microfluidic devices and systems to perform the separation, it is often the case that the analyte of interest may be present in the sample at very low concentration and in very small volumes. Often, the amount of analyte may fall at, near or below the detection threshold for the microfluidic analytical system. Accordingly, it may be preferable in certain situations to use one or more on-line sample concentration or sample stacking operations (such as described above and below) in microfluidic devices to increase the detection sensitivity for the analyte of interest. A particularly useful example of an on-line sample concentration technique that can be used in practicing the methods of the present invention is isotachophoresis (ITP), such as described in Everaerts, F. M., Geurts, M. Mikkers, F. E. P., Verheggen, T. P. E. M *J Chromatagr.* 1976, 119, 129-155; Mikkers, F. E. P., Everaerts, F. M., Peek, J. A. F. *J. Chromatogr.* 1979, 168, 293-315; and Mikkers, F. E. P., Everaerts, F. M., Peek, J. A. F. *J. Chromatogr.* 1979, 168, 317-332, the disclosures of which are incorporated in their entirety by reference herein. In ITP, samples are usually inserted between leading and terminating electrolytes with sufficiently higher and lower electrophoretic mobilities, respectively. However, the leading and terminating electrolytes can also be placed in other combinations as well, either before or after the sample plug. See, e.g., Hirokawa, T, Okamoto, H. Ikuta, N., and Gas, B., "Optimization of Operational Modes for Transient Isotachophoresis Preconcentration-CZE," Analytical Sciences 2001, Vol. 17 Supplement i185. A steady-state configuration is ultimately reached according to well known moving boundary principles and all sample zones migrate at the same velocity. The sample concentration in each migrating zone adjusts itself with respect to the concentration of the leading electrolytes. In the present invention, ITP was used as a sample concentration method in Example 2 described below to perform an AFP assay in which Poly (dI-dC) was used to remove serum interference. There are many other different sample concentration techniques used in capillary electrophoresis other than ITP which can be used in practicing the methods of the present invention, such as field amplified sample stacking (FASS) and solid phase extraction (SPE). For example, FASS on a microfluidic chip using simultaneous multiport pressure and electrokinetic fluid control is described in co-pending patent application Ser. No. 10/206,386 for "Microfluidic Methods, Devices and Systems for In Situ Material Concentration," the entire contents of which are incorporated by reference herein. In addition, a variety of other recently developed sample concentration methods may be used in practicing the methods of the current invention, such as the use of pH changes to the leading/terminating electrolytes to create sample stacking regions (see, e.g., Weiss, D. J., Saunders, K., Lunte, C. E. *Electrophoresis* 2001, 22, 59-65; Britz-McKibbin, P., Bebault, G. M., Chen, D. D. Y. *Anal Chem.* 2000, 72, 1729-1735, the entire contents of which are incorporated by reference herein), and/or by balancing the electrophoretic velocity of analytes against the bulk flow of solution in the presence of a temperature gradient (see, e.g., Ross, D., Locascio, L. E. *Anal Chem.* 2002, 71, 5137-5145, the entire contents of which are further incorporated by reference herein). In the present invention, all of the buffers, fillers, a variety of reagents such as processing solutions, etc., conventionally used in the separation methods as mentioned above may be utilized. The concentration of these materials may be chosen optionally according to the known separation methods. The condition for separation (e.g., pH, temperature, applied voltage, time, and so on) may properly be chosen according to known methods.

I. Microfluidic Device

In the present invention, a separation of the complex of the objective substance and the affinity substance (e.g., the analyte/affinity molecule complex, the analyte/conjugate complex or the analyte/affinity molecule/conjugate complex) from the free affinity substance not involved in the formation of the complex (e.g., the affinity molecule and/or the conjugate) can be conducted by using a microfluidic system generally including a microfluidic device and a detector based on the above-mentioned separation methods. The methods of the present invention are well suited to application in microfluidic devices. Samples can be introduced into microfluidic devices for quick, accurate migration shift assays using minimal volumes of reagents and samples. Mixtures of samples with an affinity substance (e.g., affinity molecule and/or conjugate) can be introduced in low salt buffers while buffers in the separation media have higher salt content to provide a "stacking" effect of accumulating assay mixture components at the front of the sample bolus for higher sensitivity and better resolution. Samples can be screened in a high throughput screening format, e.g., by sipping samples from sample library chips or multiwell plates (e.g., standard 96, 384 or other larger multiwell plates) to microfluidic devices (e.g., chips) for rapid screening, data acquisition and data interpretation. The microfluidic device can have, e.g., one or more separation channels containing the separation media and flowing into a detection channel region or separate detection channel where effluent is monitored by a detector. The microfluidic devices of the present invention can include, e.g., a detector to detect the separated components in the sample. Such detectors can include, e.g., gel scanners, fluorescence detectors, or fluorescence polarization detectors.

The microfluidic device to be used in the present invention typically has a body structure which includes and/or contains at least one fluidic component, e.g., a channel, chamber, well or the like, which has at least one cross sectional dimension that is between about 0.1 and about 500 µm, with these channels and/or chambers often having at least one cross-sectional dimension between about 0.1 µm and 200 µm, in some cases between about 0.1 µm and 100 µm, and often between about 0.1 µm and 20 µm. Such cross-sectional dimensions include, e.g., width, depth, height, diameter or the like. Typically, structures having these dimensions are also described as being "microscale." Microfluidic devices in accordance with the present invention typically include at least one, and preferably more than one channel and/or chamber disposed within a single body structure. Such channels/chambers may be separate and discrete, or alternatively, they may be fluidly connected. Such fluid connections may be provided by channels, channel intersections, valves and the like. Channel intersections may exist in a number of formats, including cross intersections, "T" intersections, or any number of other structures whereby two channels are in fluid communication.

The body structure of the microfluidic devices described herein typically comprises an aggregation of two or more separate components which when appropriately mated or joined together, form the microfluidic device of the present invention, e.g., containing the channels and/or chambers described herein. Typically, the microfluidic devices described herein are fabricated as an aggregate of substrate layers. In particular, such preferred devices comprise a top portion, a bottom portion, and an interior portion, wherein the interior portion substantially defines the channels and chambers of the device. A variety of substrate materials may be employed as the bottom portion. Typically, because the devices are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), and the like. Such polymeric substrates are readily manufactured using available microfabrication techniques, as described above, or from microfabricated masters, using well known molding techniques, such as injection molding, embossing or stamping or the like. Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. Pat. No. 5,885,470, which is incorporated herein by reference in its entirety for all purposes.

The microfluidic system of the present invention preferably includes a detector. A detector monitoring elution from the separation channel can detect elution of the affinity substance/objective substance complex (e.g., affinity molecule/analyte complex, conjugate/analyte complex or affinity molecule/conjugate/analyte complex) before the free affinity substance (e.g., free affinity molecule and/or free conjugate) reaches the detector. Microfluidic devices, such as the Agilent DNA 500 LabChip®, can provide quick analysis of multiple samples with high sensitivity and resolution.

A detector can be positioned to detect free affinity substance and/or affinity substance/analyte complex as they elute from the separation media in the separation channel. The affinity substance (e.g., conjugate) can be detected without modification or detectable markers can be associated with the affinity substance (e.g., conjugate) for enhanced detection sensitivity. The affinity substance (e.g., conjugate) can include certain charged carrier molecules such as polymers which are detectable, e.g., by their distinctive light absorbance characteristics. For example, DNA as a charged carrier molecule can have a strong absorbance at about 260 nm for detection by a spectrophotometer as it elutes from the separation media.

Detectors can be positioned, e.g., at the effluent end of a separation channel to monitor the elution of detectable peaks. Optionally, a detector can scan across a separation media, such as a polyacrylamide gel, to detect the relative positions of separated complex and free affinity substance (e.g., free affinity molecule and/or free conjugate). The detector can be any type appropriate to the detectable marker, such as an absorbance detector, fluorescence detector, fluorescence polarization detector, spectrophotometer, phosphoimager, voltage meter, scintillation counter, refractometer, and/or the like. Such detectors can provide a digital or analog output signal that can be interpreted to identify and/or quantify an analyte.

Interpretation of detector output with time can be used, e.g., to determine the presence of an analyte and/or to quantitate the amount of the analyte present in the sample. Peak parameters, such as retention time, migration rate, peak height, peak location, and peak ratios, can be interpreted to identify the presence of analyte and/or quantify the amount of analyte in a sample. Standard analytical techniques, such as the use of reference samples, standard samples, and regression analysis, can be employed to interpret the results of analyses.

Figure 2:
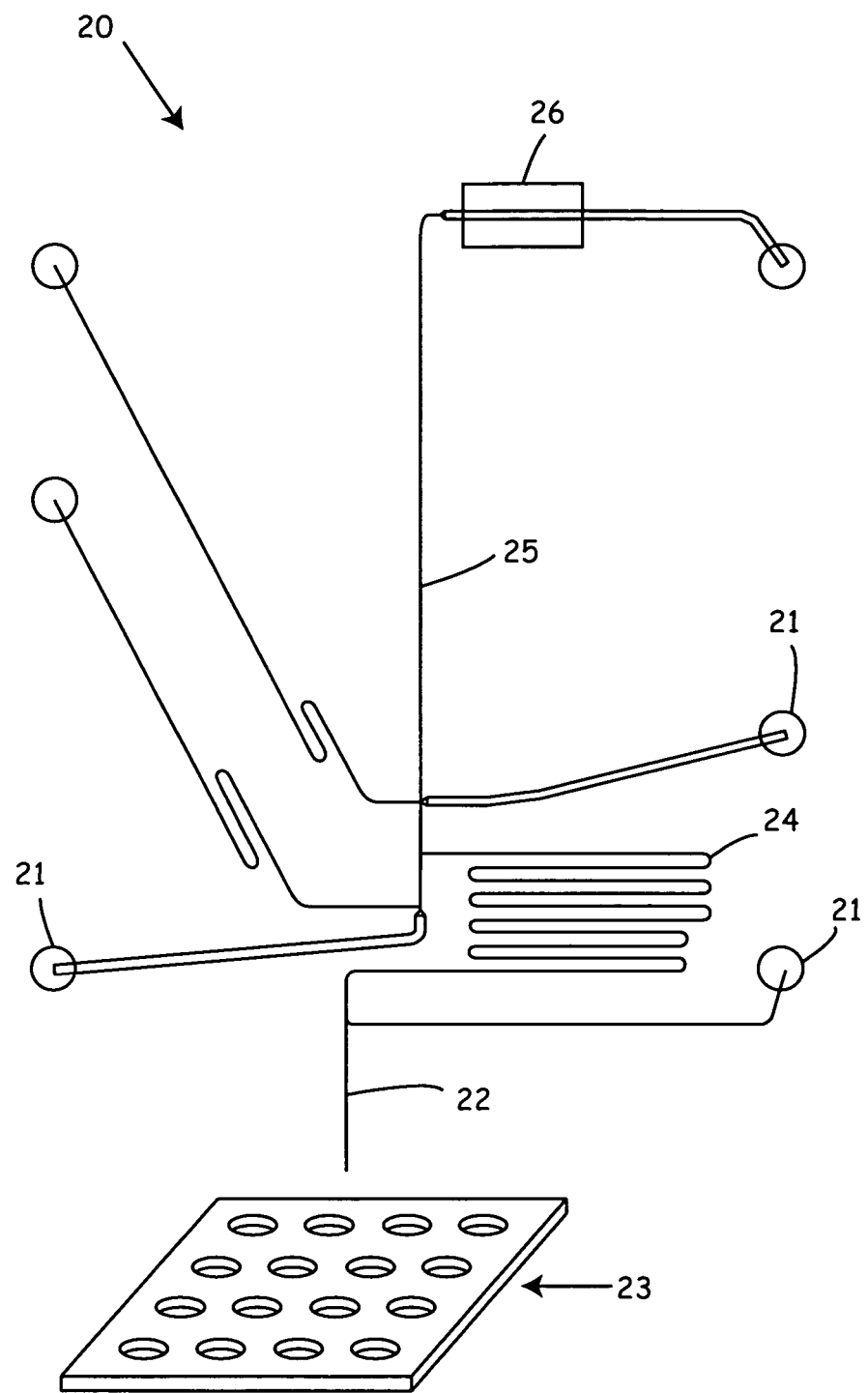
FIG. 2 is a schematic diagram of a microfluidic device for running a migration shift assay as used in the Examples.

The microfluidic system and device (e.g., microfluidic chip) of the present invention, such as the Agilent Bioanalyzer 2100 using the DNA 500 LabChip, can provide fast, high resolution separations using small sample loads. As shown in FIG. 2, microfluidic device 20 can have, e.g., sample wells and/or reagent wells 21 connected through flow controlled micro channels. The device of the present invention can comprise, for example, a microfluidic chip with wells for the blocker polymer and affinity substance (e.g., affinity molecule and/or conjugate), and sipper capillary tube 22 to aliquot samples from multi-well plate 23. The chip can include, e.g., merging microchannels for mixing assay components, incubation channels 24 to allow time for reactions, and separation channels 25 filled with separation media. Flow control systems can direct the contact of a charged polymer from a well and sample from the sipper through merging microchannels followed by mixing with affinity substance (e.g., affinity molecule and/or conjugate) from the affinity substance well. After an adequate period flowing in an incubation channel, the processed sample can be applied to a separation media of, for example, poly-N, N-dimethylacrylamide (pDMA) buffer where free affinity substance (e.g., free affinity molecule and/or free conjugate) is separated from affinity substance/analyte complex (e.g., affinity molecule/analyte complex, conjugate/analyte complex or affinity molecule/analyte/conjugate complex). The free affinity substance can exit the separation channel first to be detected before any affinity substance/analyte complex. Detector 26, such as a fluorescence detector, monitors buffers exiting the separation channel, to detect the fluorescent labeled affinity substance with high sensitivity, and sends an output signal to a logic circuit. Information from the separation can be interpreted to identify the presence of the analyte (e.g., affinity substance/analyte complex) and/or the quantity of analyte.

A variety of material transport methods are optionally used in accordance with such microfluidic devices. For example, in one preferred aspect material movement through the channels of a device is caused by the application of pressure differentials across the channels through which material flow is desired. This may be accomplished by applying a positive pressure to one end of a channel or a negative pressure to the other end. In complex channel networks, controlled flow rates in all of the various interconnected channels may be controlled by the inclusion of valves, and the like within the device structure, e.g., to stop and start flow through a given channel. Alternatively, channel resistances may be adjusted to dictate the rate, timing and/or volume of material movement through different channels, even under a single applied pressure differential, e.g., a vacuum applied at a single channel port. Examples of such channel networks are illustrated in e.g., U.S. patent application Ser. No. 09/238,467, filed Jan. 28, 1999, and Ser. No. 09/233,700, filed Jan. 19, 1999 and Ser. No. 09/277,367, filed Mar. 26, 1999, all of which are hereby incorporated herein by reference in their entirety for all purposes.

Alternately, for microfluidic applications of the present invention, controlled electrokinetic transport systems may be used. This type of electrokinetic transport is described in detail in U.S. Pat. No. 5,858,195, to Ramsey, which is incorporated herein by reference for all purposes. Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel, will cause the proton sheath to move in the direction of the voltage drop, i.e., toward the negative electrode.

"Controlled electrokinetic material transport and direction," as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirable of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage). However, this type of material flow through the intersection would result in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves which include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the 'off' mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed in this manner. Although described for the purposes of illustration with respect to a four way, cross intersection, these controlled electrokinetic material transport systems can be readily adapted for more complex interconnected channel networks, e.g., arrays of interconnected parallel channels.

Where affinity substance (e.g., affinity molecule and/or conjugate) migration through separation media is driven by a voltage potential, such as in electrophoresis, large loads can be applied in low salt buffers to provide improved sensitivity while retaining adequate resolution. If the sample contains only a low concentration of analyte or if the mixture is highly diluted in handling, it can be desirable to load a large sample onto the separation media for better sensitivity in migration shift analysis. However, a large sample can enter the separation media as a broad bolus that elutes as broad, poorly resolved peaks. This problem can be reduced by applying the sample in a low salt buffer while running the electrophoresis in a higher salt running buffer. The low salt sample is relatively deficient in charged carriers for the electrophoretic current so the charged sample components move quickly to stack at the front of the sample bolus. The charged sample components accumulate in a sharp band at the front of the sample bolus when they reach the higher salt running buffer with the abundant charge carriers. In this way, a large volume dilute sample can be applied to an electrophoretic separation media for stronger peak detection without substantial loss of resolution.

The detector of the system can include any device appropriate to the signal of interest. Where the affinity substance has a useful light absorbance spectrum, the detector can be a spectrophotometer. Where the affinity substance has an associated detectable marker, the detector can be a suitable type for the marker. For example, a fluorometer for a fluorescent marker, a scintillation counter for a radioactive marker, a photodiode tube for a chemiluminescent marker, and the like. If the separation is carried out by polyacrylamide gel electrophoresis (PAGE), the detector can include, e.g., a scanner which detects the extent of free affinity substance and/or affinity substance/analyte complex band migration across the gel. If the separation is carried out by chromatography or capillary electrophoresis, the detector can be, e.g., an appropriate detector focused on the effluent stream from the separation media to detect free affinity substance and/or affinity substance/analyte complex as they elute over time. Such detectors can provide analog or digital output signals that can be interpreted by a logic circuit of the invention.

Logic circuits of the device can receive, e.g., quantitative signals from the detectors that vary of the amount of affinity substance detected, e.g., at a gel location or in a chromatographic effluent over time. The logic circuit can be as simple as a chart recorder that plots signal amplitude on a moving chart paper, or can be a sophisticated digital computer/software system. Commonly available software, such as Agilent Technologies 2100 Bioanalyzer-Biosizing [DNA 7500], can provide, e.g., peak identifications, peak heights, peak area integrations, background subtraction, regression analysis, to identify and quantitate analytes.

J. Separation Media

In the present invention, it is preferable to use a separation media such as a polymer having a molecular sieving effect in a separation channel of the above-mentioned microfluidic device and to conduct the separation through the separation media. There is no particular limitation for the separation media (e.g., filler) packed in the separation channel as far as it has been conventionally used in the field of the present invention.

Specifically, separation of the free affinity substance and the analyte/affinity substance complex is preferably performed by capillary gel electrophoresis in, e.g., a separation media disposed in a separation channel of a microfluidic device. In capillary gel electrophoresis, the separation media is, e.g., a restrictive matrix of linear or cross-linked polymers which can impede the flow of large molecules while allowing free flow of smaller molecules.

Such separation media can include, for example, polyethers such as polyethylene oxide (PEO), polyethylene glycol (PEG), polypropylene oxide, etc.; polyalkylenimines such as polyethylenimine, etc.; polyacrylic acid-type polymers such as polyacrylic acid, polyacrylate ester, methyl polyacrylate, etc.; polyamide type polymers such as polyacrylamide, poly-methacrylamide, poly-n,n-dimethylacrylamide (pDMA) etc.; polymethacrylic acid-type polymers such as polymethacrylic acid, poly-methacrylate ester, methyl polymethacrylate, etc.; polyvinyl-type polymers such as polyvinyl acetate, polyvinylpyrrolidone (PVP), polyvinyloxazolidone, etc.; water-soluble hydroxyl polymers such as pullulan, yersinan, xanthan, dextran, guar gum, agarose gel, etc.; water-soluble cellulose such as methylcellulose, hydroxyethylcellulose (HEC), hydroxypropylcellulose, etc.; water-soluble co-polymers such as co-polymer of sucrose and epichlorohydrin [e.g., Ficoll (a trade name, Pharmacia)]; and their derivatives, and co-polymers containing multiple kinds of monomer units constituting their polymers. The separation media may be used alone or in combination of two or more members. Among them, a polyacrylamide gel, polyethylene glycol (PEG), polyethyleneoxide (PEO), a co-polymer of sucrose and epichlorohydrin (Ficoll), polyvinylpyrrolidone (PVP), hydroxyethylcellulose (HEC), poly-N,N-dimethylacrylamide (pDMA), agarose gel are preferable. Poly-N,N-dimethylacrylamide (pDMA) is most preferable.

Such media can be loaded into separation channels of a microfluidic device to provide, e.g., rapid, high throughput separations. In the present invention, it is not necessary to use the above-mentioned separation media, but the separation can also be conducted by using only water or a buffer.

The molecular weight of the separation media mentioned above is usually between about 500 Da to 6,000 kDa, preferably 1 to 1,000 kDa, more preferably 100 to 1,000 kDa. The concentration of the separation media used as mentioned above is chosen optionally within the range usually employed in field of the present invention, that is, usually between about 0.01 to 40% (w/v), preferably 0.01 to 20% (w/v), more preferably 0.1 to 10% (w/v). Usually, inside the separation channel of the microfluidic device, the above-mentioned separation media is packed together with a buffer.

There is no particular limitation on the type of buffer which can be used in practicing the methods of the present invention. For example, the buffer to be used can include many of those used in the field of hybridization assays, immunoassays, and the like, such as for example, tris-buffer, phosphate buffer, Veronal buffer, borate buffer, Good's buffer, SSC buffer, TBE buffer, TAE buffer, etc. These buffers may be usually used in a concentration of between about 0.1 mM to 10M, preferably 1 mM to 5M, more preferably 5 mM to 1M. The pH of the buffer may be in any range where the substance separation is not adversely affected and is usually between about 2 to 13, preferably 4 to 11, more preferably 5 to 9. Such parameters can be optimized to achieve field amplification stacking if desired. When the above-mentioned separation media is added to a buffer, the viscosity of the buffer is usually between about 2 to 1,000 centipoises, preferably 5 to 200 centipoises, more preferably 10 to 100 centipoises.

Separation can also be, e.g., by size exclusion chromatography (SEC). SEC resin can have pores large enough to receive the affinity substance (e.g., affinity molecule and/or conjugate) but not large enough to receive the affinity substance/analyte complex (e.g., affinity molecule/analyte complex, conjugate/analyte complex or affinity molecule/analyte/conjugate complex). When the mixture is pumped through a column of SEC resin, the affinity substance/analyte complex flows only in the volume outside the resin while the free affinity substance flows more slowly through the outside volume plus the inner resin volume.

K. Detection

The analyte/affinity substance complex (e.g., the analyte/affinity molecule complex, the analyte/conjugate complex or the analyte/affinity molecule/conjugate complex) or free affinity substance (e.g., free affinity molecule and/or free conjugate) which is not involved in forming the complex separated by the above-mentioned separation method can be measured or detected by a method corresponding to the properties of the detectable property of the molecules involved (e.g., the detectable marker associated therewith). Thus, the amount of the analyte in a sample can be determined or the presence of the analyte in the sample can be identified. That is, the analyte/affinity molecule complex is separated from the free affinity molecule which is not involved in the formation of the complex, the analyte/conjugate complex is separated from the free conjugate which is not involved in the formation of the complex, or the analyte/affinity molecule/conjugate complex is separated from the free affinity molecule and/or conjugate which is not involved in the formation of the complex, according to the above-mentioned separation. The resulting complex, or free affinity molecule and/or free conjugate may be measured or detected by a method corresponding to the properties of these (e.g., the detectable marker). Thus, the amount of the analyte in a sample can be determined or the presence of the analyte in the sample can be identified in high sensitivity and in a short period of time.

Several specific embodiments of the present invention are shown in FIGS. 3A to 3F. A variety of immunochemical assay techniques known in the art can be used in practicing the present invention to detect an analyte of interest in the sample, such as antibody sandwich assays and enzyme-linked immunoassays (see, e.g., Bolton et al., Handbook of Experimental Immunology, Weir, D. M., Ed., Blackwell Scientific Publications, Oxford, 1986, vol. 1, Chapter 26, for a general discussion on immunoassays), and other similar assay formats known to those of ordinary skill in the art. For example, as described above, and shown for example in FIG. 3A, the assay format may be used to separate a complex 30 comprising an analyte 32 and a corresponding conjugate 31 comprising an affinity molecule 34 such as an antibody or antigen linked (e.g., conjugated) to a labeled charged carrier molecule 36, e.g., a fluorescently labeled DNA molecule having one ore more fluorescent tags attached thereto, from any free (unbound) antibody/charged carrier molecule conjugate 31 (for convenience and clarity, the separation step is represented by the symbol "l" in the figures). Alternatively, a sandwich immunoassay format can be performed as shown in FIGS. 3B-F wherein a tagged (e.g., labeled) binding moiety/analyte complex, such as a fluorescently labeled antibody/analyte complex, is utilized to detectably bind to another binding moiety (e.g., a labeled or non-labeled antibody or DNA-antibody conjugate).

Figure 3A:
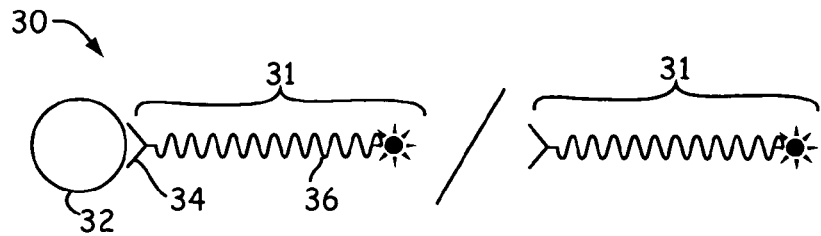
FIGS. 3A-K are schematic illustrations of various immunoassay formats that can be used to detect an analyte of interest in a sample using the methods of the present invention.
Figure 3B:
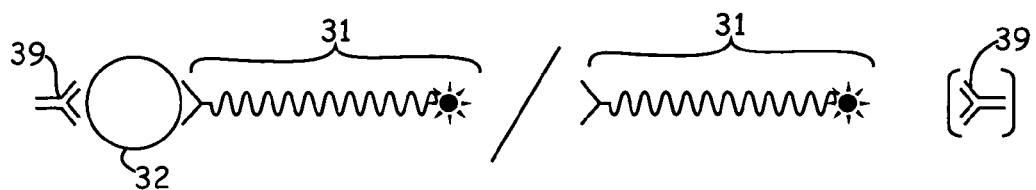
Figure 3C:
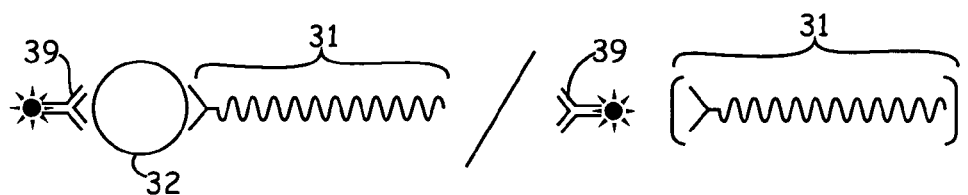
Figure 3D:
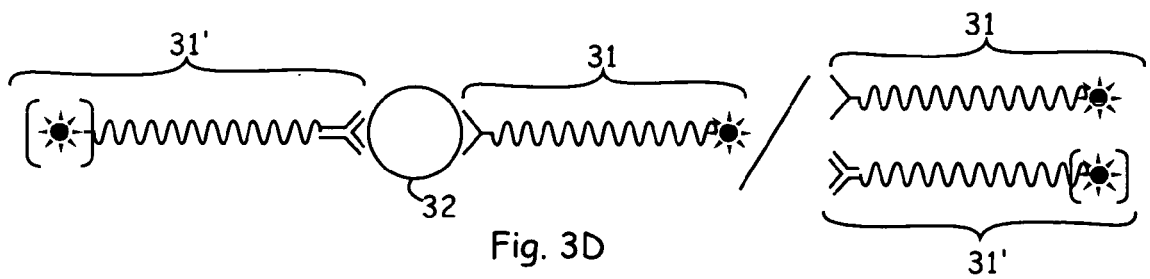
Figure 3E:
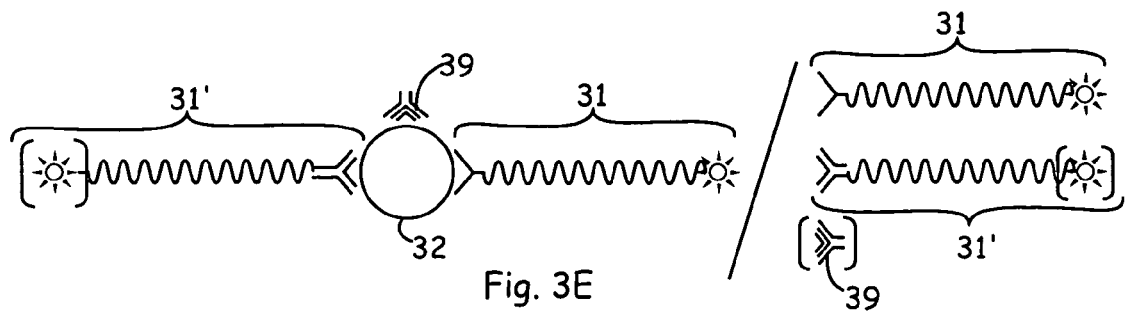
Figure 3F:
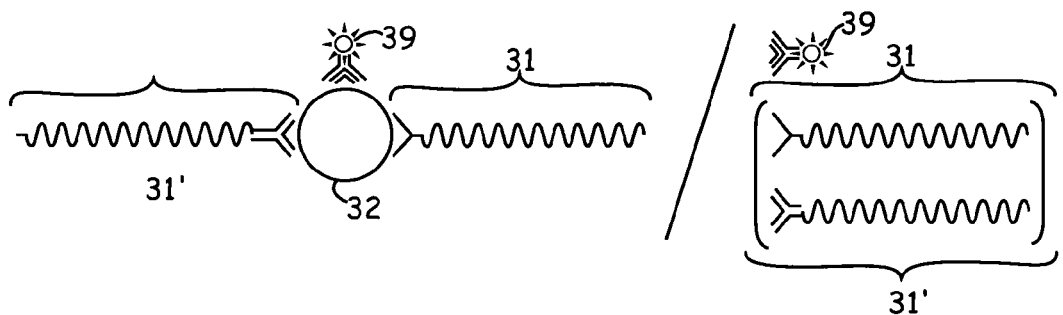
Figure 3G:
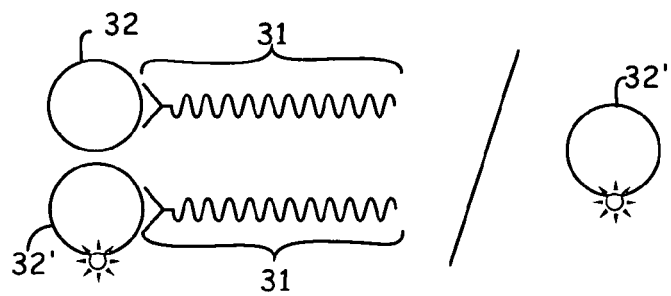
Figure 3H:
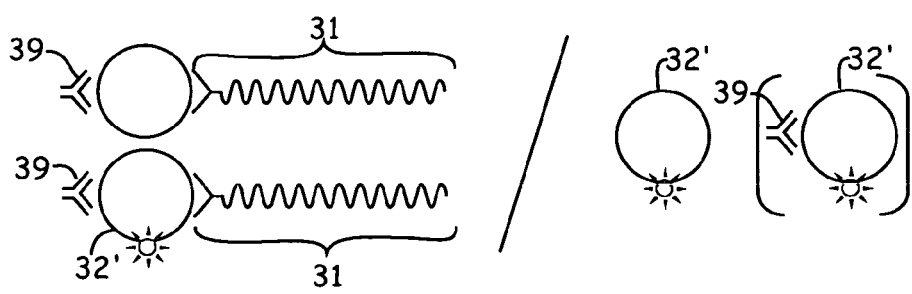
Figure 3I:
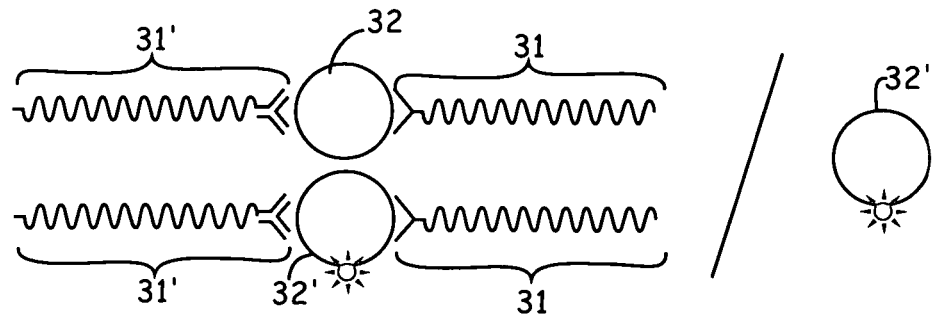
Figure 3J:
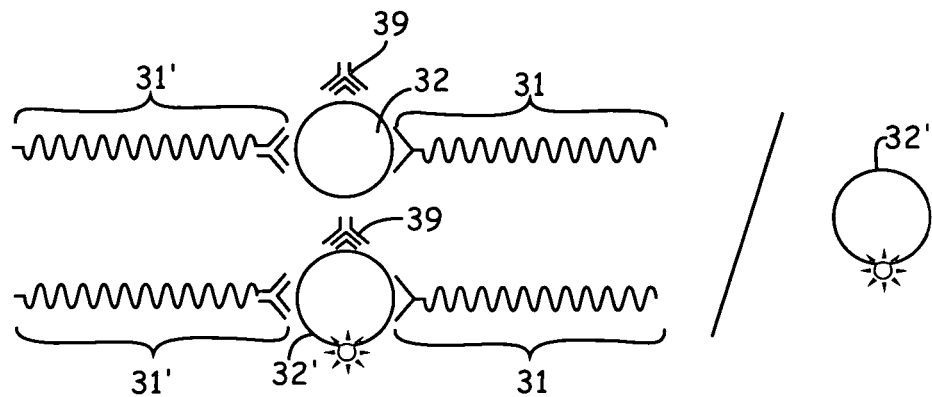
Figure 3K:
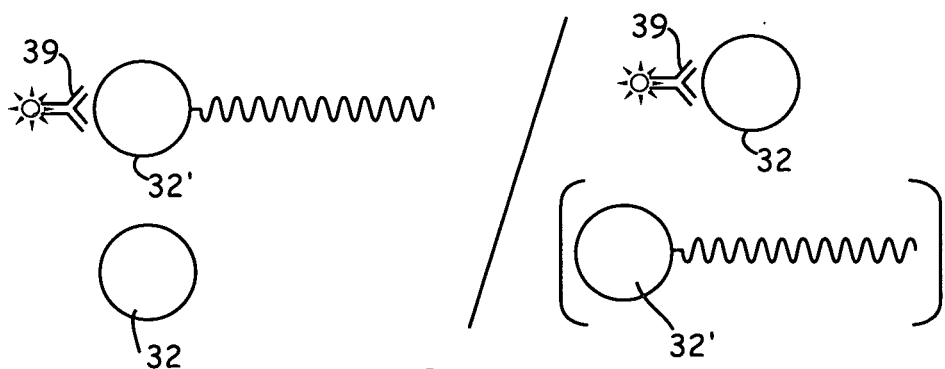

A first example of a sandwich immunoassay is illustrated schematically in FIG. 3B, which illustrates binding of the antigen/labeled antibody 31 complex to another affinity molecule, e.g., antibody 39. The sample containing the analyte of interest 32 is preferably pre-incubated with the labeled conjugate 31 to form the binding moiety/analyte complex. FIG. 3C shows a sandwich immunoassay format in which the second antibody 39 includes a fluorescent label and the DNA-antibody conjugate 31 is unlabeled. FIGS. 3D-F show a sandwich immunoassay format in which two (or more) DNA-antibody conjugates 31, 31' are used (FIG. 3D), and in which a third labeled or unlabeled affinity molecule 39 is also used (FIGS. 3E-F). When two or more affinity molecules are used as shown in FIGS. 3B-F, for example, each affinity molecule typically binds to the analyte at a different site on the analyte from every other affinity molecule.

In the above-mentioned FIGS. 3A to 3F, one, two, or more than two of each of the conjugate 31 and 31', the labeled conjugate 31, the affinity molecule 39 and the labeled affinity molecule 39 may be used in practicing the methods of the present invention. Specific, non-limiting examples of assays employing the sandwich assay format are as follows:
(a) A method for determining or identifying an analyte in a sample is disclosed, which comprises: (i) contacting the sample containing the analyte with one or more affinity molecules, at least one of which is labeled by a detectable marker, to form a complex containing the analyte and the affinity molecule labeled by the detectable marker; (ii) separating the complex from any free affinity molecule labeled by the detectable marker which is not involved in forming the complex in a separation channel of a microfluidic device in the presence of a charged polymer; (iii) measuring an amount of the separated complex or detecting a presence of the separated complex; and (iv) determining an amount of the analyte in the sample on the basis of the measured amount or identifying a presence of the analyte in the sample on the basis of the detected presence; wherein the affinity molecule has a property capable of binding to the analyte, and wherein when two or more affinity molecules are used, each affinity molecule has a property capable of binding with the analyte at a different site on the analyte from every other affinity molecule:

(b) A method for determining or identifying an analyte in a sample is disclosed, which comprises: (i) contacting the sample containing the analyte with one or more conjugates of an affinity molecule and a charged carrier molecule, wherein at least one of the one or more conjugates is labeled by a detectable marker, to form a complex containing the analyte and the conjugate labeled by the detectable marker; (ii) separating the complex from the conjugate labeled by the detectable marker which is not involved in the complex in a separation channel of a microfluidic device in the presence of a charged polymer; (iii) measuring an amount of the separated complex or detecting a presence of the separated complex; and (iv) determining an amount of the analyte in the sample on the basis of the measured amount or identifying a presence of the analyte in the sample on the basis of the detected presence; wherein the affinity molecule in the conjugate has a property capable of binding to the analyte, and when two or more conjugates are used, each affinity molecule in the conjugate has a property capable of binding with the analyte at a different site on the analyte from every other affinity molecule, and the charged carrier molecule has a property capable of causing a change in a separation (e.g., migration) property of the analyte by binding to the analyte through the affinity molecule to form a complex of the analyte, the affinity molecule and the charged carrier molecule. In other words, the charged carrier molecule causes a change in a separation (e.g., migration) property of the analyte and enables a complex containing the analyte and the conjugate labeled by the detectable marker to separate from the conjugate labeled by the detectable marker which is not involved in the complex, by binding to the analyte through the affinity molecule to form the complex containing the analyte and the conjugate labeled by the detectable marker.

(c) A method for determining or identifying an analyte in a sample is disclosed, which comprises: (i) contacting the sample containing the analyte with one or more affinity molecules and one or more conjugates of an affinity molecule and a charged carrier molecule, wherein either at least one of the affinity molecule or at least one of the conjugate is labeled by a detectable marker, to form a complex containing the analyte, the affinity molecule and the conjugate; (ii) separating the complex from any free affinity molecule labeled by the detectable marker or the conjugate labeled by the detectable marker which is not involved in forming the complex in a separation channel of a microfluidic device in the presence of a charged polymer; (iii) measuring an amount of the separated complex or detecting a presence of the separated complex; and (iv) determining an amount of the analyte in the sample on the basis of the measured amount or identifying a presence of the analyte in the sample on the basis of the detected presence; wherein the affinity molecule and the affinity molecule in the conjugate have a property capable of binding to the analyte, and each affinity molecule has a property capable of binding with the analyte at a different site on the analyte from every other affinity molecule, and the charged carrier molecule has a property capable of causing a change in a separation (e.g., migration) property of the analyte by binding to the analyte through the affinity molecule to form a complex of the analyte, the affinity molecule and the charged carrier molecule. In other words, the charged carrier molecule causes a change in a separation (e.g., migration) property of the analyte and enables a complex containing the analyte, the affinity molecule and the conjugate to separate from the free affinity molecule labeled by the detectable marker or the free conjugate labeled by the detectable marker which is not involved in the complex, by binding to the analyte through the affinity molecule to form the complex containing the analyte, the affinity molecule and the conjugate.

Alternatively, the analyte in a sample can be measured by so-called competitive assays in which labeled analyte or analyte bound with the charged carrier molecule (or the labeled analogue of the analyte or analyte analogue bound to the charged carrier molecule) is employed for competitive reactions between the labeled analyte or analyte bound with the charged carrier molecule (or the labeled analogue of the analyte or analyte analogue bound to the charged carrier molecule) and the analyte in the sample.

In competitive assays, the affinity molecule has a property capable of binding to the analyte in the sample and the labeled analyte (or the labeled analogue). When two or more affinity molecules are used, each affinity molecule has a property capable of binding with the analyte in the sample and the labeled analyte at a different site on the analyte in the sample and a different site on the labeled analyte from every other affinity molecule, or each affinity molecule has a property capable of binding with the analyte in the sample and the labeled analogue at a different site on the analyte in the sample and a different site on the labeled analogue from every other affinity molecule. Additionally, when the analyte exists in both a form bound with a protein or other binding substance (e.g., the bound form) and a form unbound with a protein or other binding substance (e.g., the unbound form) in a sample, wherein the bound form and the unbound form are in equilibrium, the competitive assay using the analogue of the analyte can be used to analyze the unbound form of analyte.

Other embodiments of the present invention which use the competitive assay format are typically shown in FIGS. 3G to 3K. In the embodiments shown for example in FIGS. 3G-J, a competitive assay can be used in which a labeled analyte or a labeled analogue of the analyte (e.g., analyte 32') competes with an analyte of interest 32 in the sample for binding to one or more non-labeled affinity molecule(s) such as an antibody or a DNA-antibody conjugate (e.g., DNA-antibody conjugate(s) 31 and/or 31'). Multiple affinity molecules may be used when it is desirable or necessary to provide higher resolution of the detectable signal in the sizing assay, as shown for example in FIGS. 3H and 3I. In another embodiment as shown for example in FIG. 3K, a competitive assay can be used in which an analyte or an analyte analogue (e.g., analyte 32') bound with a charged carrier molecule (e.g., nucleotide chain) competes with an analyte of interest 32 in the sample for binding to one or more labeled affinity molecule(s) such as an antibody (e.g., labeled antibody 39). In the above-mentioned FIGS. 3G to 3K, one, two or more than two of the conjugate 31 and 31', the affinity molecule 39 and the labeled affinity molecule 39 may be used in practicing the methods of the present invention.

In the above-mentioned method of the present invention, when the unbound form of analyte is determined by using the analogue of the analyte, it is preferable that the analogue of the analyte dose not react substantially with proteins or other binding substances which bind with the analyte to form the bound form. The labeled affinity molecule in FIG. 3K binds with at least the analyte of the unbound form and the analogue. It is preferable that the labeled affinity molecule binds with the analyte of the unbound form and the analogue but does not bind with the analyte of the bound form.

Specific examples of assays performed by using the competitive assay format are as follows: (a) A method for determining an analyte in a sample is disclosed, which comprises: (i) contacting the sample containing the analyte with the analyte (or the analogue) labeled by a detectable marker and one or more affinity molecule to form a first complex of the analyte in the sample and the affinity molecule and a second complex of the labeled analyte (or the labeled analogue) and the affinity molecule; (ii) separating the second complex from any free labeled analyte (or free labeled analogue) which is not involved in forming the second complex in a separation channel of a microfluidic device in the presence of a charged polymer; (iii) measuring an amount of the separated second complex or an amount of the separated free labeled analyte (or the separated free labeled analogue); and (iv) determining an amount of the analyte in the sample on the basis of the measured amount; wherein the affinity molecule has a property capable of binding to the analyte in the sample and the labeled analyte or a property capable of binding to the analyte in the sample and the labeled analogue, and wherein when two or more affinity molecules are used, each affinity molecule has a property capable of binding with the analyte in the sample and the labeled analyte at a different site on the analyte in the sample and a different site on the labeled analyte from every other affinity molecule or each affinity molecule has a property capable of binding with the analyte in the sample and the labeled analogue at a different site on the analyte in the sample and a different site on the labeled analogue from every other affinity molecule. The affinity of the affinity molecule toward the analyte in the sample and the labeled analyte is preferably the same or the affinity of the affinity molecule toward the analyte in the sample and the labeled analogue is preferably the same. In the above-mentioned method of the present invention, when the unbound form of analyte is analyzed by using the analogue of the analyte, the analogue of the analyte is needed to be substantially non-reactive with proteins or other binding substances which bind with the analyte to form the bound form.

(b) A method for determining an analyte in a sample is disclosed, which comprises: (i) contacting the sample containing the analyte with the analyte (or the analogue) labeled by a detectable marker and one or more conjugate of an affinity molecule and a charged carrier molecule to form a first complex of the analyte in the sample and the conjugate and a second complex of the labeled analyte (or the labeled analogue) and the conjugate; (ii) separating the second complex from any free labeled analyte (or free labeled analogue) which is not involved in forming the second complex in a separation channel of a microfluidic device in the presence of a charged polymer; (iii) measuring an amount of the separated second complex or an amount of the separated free labeled analyte (or the separated free labeled analogue); and (iv) determining an amount of the analyte in the sample on the basis of the measured amount; wherein the affinity molecule in the conjugate has a property capable of binding to the analyte in the sample and the labeled analyte or the analyte in the sample and the labeled analogue, and when two or more conjugates are used, each affinity molecule in the conjugate has a property capable of binding with the analyte in the sample and the labeled analyte at a different site on the analyte in the sample and a different site on the labeled analyte from every other affinity molecule or each affinity molecule in the conjugate has a property capable of binding with the analyte in the sample and the labeled analogue at a different site on the analyte in the sample and a different site on the labeled analogue from every other affinity molecule, and the charged carrier molecule has a property capable of causing a change in a separation (e.g., migration) property of the labeled analyte (or the labeled analogue) by binding to the labeled analyte (or the labeled analogue) through the affinity molecule to form a complex of the labeled analyte (or the labeled analogue), the affinity molecule and the charged carrier molecule. In other words, the charged carrier molecule causes a change in a separation (e.g., migration) property of the labeled analyte (or the labeled analogue) and enables a second complex of the labeled analyte (or the labeled analogue) and the conjugate to separate from the free labeled analyte (or free labeled analogue) which is not involved in the complex, by binding to the labeled analyte (or the labeled analogue) through the affinity molecule to form the second complex of the labeled analyte (or the labeled analogue) and the conjugate. The affinity of the affinity molecule toward the analyte in the sample and the labeled analyte is preferably the same or the affinity of the affinity molecule toward the analyte in the sample and the labeled analogue is preferably the same. In the above-mentioned method of the present invention, when the unbound form of analyte is analyzed by using the analogue of the analyte, the analogue of the analyte is needed to be substantially non-reactive with proteins or other binding substances which bind with the analyte to form the bound form.

(c) A method for determining an analyte in a sample is disclosed, which comprises: (i) contacting the sample containing the analyte with the analyte (or the analogue) labeled by a detectable marker, one or more affinity molecule and one or more conjugate of an affinity molecule and a charged carrier molecule to form a first complex of the analyte in the sample, the affinity molecule and the conjugate and a second complex of the labeled analyte (or the labeled analogue), the affinity molecule and the conjugate; (ii) separating the second complex from any free labeled analyte (or free labeled analogue) which is not involved in forming the second complex in a separation channel of a microfluidic device in the presence of a charged polymer; (iii) measuring an amount of the separated second complex or an amount of the separated free labeled analyte (or the separated free labeled analogue); and (iv) determining an amount of the analyte in the sample on the basis of the measured amount; wherein the affinity molecule and the affinity molecule in the conjugate have a property capable of binding to the analyte in the sample and the labeled analyte or the analyte in the sample and the labeled analogue, and each affinity molecule has a property capable of binding with the analyte in the sample and the labeled analyte at a different site on the analyte in the sample and a different site on the labeled analyte from every other affinity molecule or each affinity molecule has a property capable of binding with the analyte in the sample and the labeled analogue at a different site on each of the analyte in the sample and a different site on the labeled analogue from every other affinity molecule, and the charged carrier molecule has a property capable of causing a change in a separation (e.g., migration) property of the labeled analyte (or the labeled analogue) by binding to the labeled analyte (or the labeled analogue) through the affinity molecule to form a complex of the labeled analyte (or the labeled analogue), the affinity molecule and the charged carrier molecule. In other words, the charged carrier molecule causes a change in a separation (e.g., migration) property of the labeled analyte (or the labeled analogue) and enables a second complex of the labeled analyte (or the labeled analogue), the affinity molecule and the conjugate to separate from the free labeled analyte (or free labeled analogue) which is not involved in the complex, by binding to the labeled analyte (or the labeled analogue) through the affinity molecule to form the second complex of the labeled analyte (or the labeled analogue), the affinity molecule and the conjugate. The affinity of the affinity molecule toward the analyte in the sample and the labeled analyte is preferably the same or the affinity of the affinity molecule toward the analyte in the sample and the labeled analogue is preferably the same. In the above-mentioned method of the present invention, when the unbound form of analyte is analyzed by using the analogue of the analyte, the analogue of the analyte is needed to be substantially non-reactive with proteins or other binding substances which bind with the analyte to form the bound form.

(d) A method for determining an analyte in a sample is disclosed, which comprises: (i) contacting the sample containing the analyte with the analyte bound to a charged carrier molecule (or the analogue bound to a charged carrier molecule), one or more affinity molecule labeled by a detectable marker to form a first complex of the analyte bound to the charged carrier molecule (or the analogue bound to a charged carrier molecule) and the labeled affinity molecule and a second complex of the analyte in the sample and the labeled affinity molecule; (ii) separating the first complex from any second complex in a separation channel of a microfluidic device in the presence of a charged polymer; (iii) measuring an amount of the separated first complex or an amount of the second complex; and (iv) determining an amount of the analyte in the sample on the basis of the measured amount; wherein the affinity molecule has a property capable of binding to the analyte in the sample and the analyte bound to the charged carrier molecule or the analyte in the sample and the analogue bound to the charged carrier molecule, and wherein when two or more affinity molecules are used, each affinity molecule has a property capable of binding with the analyte in the sample and the analyte bound to the charged carrier molecule at a different site on the analyte in the sample and a different site on the analyte bound to the charged carrier molecule from every other affinity molecule or each affinity molecule has a property capable of binding with the analyte in the sample and the analogue bound to the charged carrier molecule at a different site on the analyte in the sample and a different site on the analogue bound to the charged carrier molecule from every other affinity molecule, and the charged carrier molecule has a property capable of causing a change in a separation (e.g., migration) property of the first complex by binding to the analyte (or the analogue) to form a complex of the analyte (or the analogue), the affinity molecule and the charged carrier molecule. In other words, the charged carrier molecule causes a change in a separation (e.g., migration) property of the labeled analyte (or the labeled analogue) and enables a complex of the analyte (or the analogue) which is not bound to the charged carrier molecule and the labeled affinity molecule to separate from the second complex of the analyte and the labeled affinity molecule, by binding to the labeled analyte (or the labeled analogue) to form the first complex of the analyte bound to the charged carrier molecule (or the analogue bound to a charged carrier molecule)

and the labeled affinity molecule. In the above-mentioned method of the present invention, the binding of the charged carrier molecule to the analyte or the analogue of the analyte may be carried out in the same manner as the binding of the charged carrier molecule to the affinity molecule as mentioned above. In the above-mentioned method of the present invention, when the unbound form of analyte is analyzed by using the analogue of the analyte, the analogue of the analyte is needed to be substantially non-reactive with proteins or other binding substances which bind with the analyte to form the bound form. The labeled affinity molecule binds with at least the analyte of the unbound form and the analogue. It is preferable that the labeled affinity molecule binds with the analyte of the unbound form and the analogue but does not bind with the analyte of the bound form. When the labeled affinity molecule binds with the analyte of the bound form, the analyte of the unbound form and the analogue, in the measuring step (iii) mentioned above, an amount of the separated first complex or a total amount of the second complex, the free labeled affinity molecule and a complex of the analyte of the bound form and the labeled affinity molecule is measured.

The above-mentioned analogue of the analyte to be used in the present invention has a property capable of binding with the affinity molecule in the similar manner as the analyte binds with the affinity molecule. That is, the analogue has functional group(s) (e.g., binding site(s)) in its structure which are functionally the same as the functional group(s) of the analyte which interact with the affinity molecule and the conjugate of the affinity molecule and the charged carrier molecule. Introducing a detectable marker and/or a charged carrier molecule in the analogue molecule does not disturb the function of such group(s) in the analogue structure in terms of interacting with the affinity molecule. The analogue in the present invention includes one which is modified, changed, denatured or has removed a part of the structure of the objective substance. Such analogues include, for example, a recombination protein which introduced a variation into a part of a protein of the objective substance, peptides which modified or changed a part of a sequence of peptides of the objective substance, nucleic acids which modified or changed a part of a sequence of nucleic acids of the objective substance and the like.

In the above mentioned case to analyze the unbound form of analyte, the analyte of interest (e.g., the objective substance) is one which exists in both a form bound with a protein or other binding substance (e.g., the bound form) and a form unbound with a protein or other binding substance (e.g., the unbound form) in a sample and wherein the bound form and the unbound form are in equilibrium. Such analytes include, for example, T4, cortisol, progesterone, estradiol, testosterone, PSA, protein C, elastase, cathepsin G, thrombin, $C_1$-esterase, plasmin, tissue-type plasminogen activator and the like. There is no particular limitation for the protein or other binding substances in the bound form as far as it has an affinity to the objective substance and a property capable of binding with the objective substance. These protein or other binding substances include, for example, globurin, prealbumin or albumin in case of T4 as the analyte of interest (the objective substance), globurin or albumin in case of cortisol, progesterone, estradiol or testosterone, $\alpha_1$-antichymotrypsin or $\alpha_2$-macrogloburin in case of PSA, protein C inhibitor in case of protein C, $\alpha_1$-trypsin inhibitor in case of elastase, $\alpha_1$-antichymotrypsin in case of cathepsin G, antithrombin III in case of thrombin, $C_1$ inhibitor in case of $C_1$-esterase, $\alpha_2$-plasmin inhibitor in case of plasmin, plasminogen activator inhibitor 1 in case of tissue-type plasminogen activator and the like.

In the above-mentioned methods, in determining the amount of the analyte in a sample based on the measured amount of the detectable marker of the separated complex or the detectable marker which is not involved in forming the complex, for example, another sample containing the analyte at a known concentration is used in the same measurement as mentioned above to prepare a calibration curve showing a relationship between the amount of the analyte thus obtained and that of the detectable marker of the separated complex or the detectable marker which is not involved in forming the complex. To this working curve is adapted the measured value of the detectable marker obtained by measurement of a sample containing the analyte to determine the amount of the intended analyte.

In addition, it is possible to calculate the relative amount of the analyte contained in a sample by adding a detectable substance as an internal standard at a known concentration to a sample, followed by comparison of the amount of the substance added as an internal standard with that of the detectable marker of the separated complex or the detectable marker which is not involved in forming the complex. In such a way, it becomes possible to correct the error between the use of multiple devices.

In the method of the present invention, measurement of the detectable marker of the separated complex or the detectable marker which is not involved in forming the complex may be achieved according to a conventional manner responding to the type of the detectable marker used. For example, when the property of the marker depends on enzymatic activity, the measurement may be conducted in a conventional way of EIA or hybridization as described in, for example, "Enzyme Immunoassay" Protein, Nucleic Acid and Enzyme, Supplementary Volume 31, Edited by Tsunehiro Kitagawa, Toshio Nambara, Akio Tuji, and Eiji Ishikawa, pages 51-63, Kyoritsu Shuppan Co., Ltd., Published on Sep. 10, 1987. When the analyte is a radioactive material, it may be detected according to a conventional way of RIA or hybridization using a suitable detector such as a dipping-type GM counter, liquid scintillation counter, well-type scintillation counter, etc., responding to the kind and strength of the radiation emitted by the radioactive material [see: Ikagaku Jikken Koza (Experimental Manual in Medical Chemistry), vol. 8, Edited by Yuichi Yamamura, First edition, Nakayama Shoten, 1971; Seikagaku Jikkenn Koza (Experimental Manual in Biochemistry), 2, Experimental Procedure for Tracer, Last Volume, Akihiro Takemura, Tasuku Honjo, pages 501-525, Tokyo Kagaku Dojin, Published on Feb. 25, 1977]. When the property of the marker depends on fluorescence, the measurement may be conducted in a conventional way of FIA or hybridization using a detector such as a fluorophotometer or confocal laser microscope as described in Zusetu (Illustrative Description) Fluorescent Antibodies, Akira Kawao, First Edition, Soft Science, 1983; Seikagaku Jikkenn Koza (Experimental Manual in Biochemistry), 2, Chemistry of Nucleic Acid III, Mineo Saneyoshi, pages 299-318, Tokyo Kagaku Dojin, Published on Dec. 15, 1977. When the property of the marker depends on luminescence, the measurement may be conducted in a conventional way using a detector such as a photon counter according to a method as described in, for example, "Enzyme Immunoassay" Protein, Nucleic Acid and Enzyme, Supplementary Volume 31, Edited by Tsunehiro Kitagawa, Toshio Nambara, Akio Tuji, and Eiji Ishikawa, pages 252-263, Kyoritsu Shuppan Co., Ltd., Published on Sep. 10, 1987. Further, when the property is of absorbance in an ultraviolet region, detection may be conducted in a conventional way using a detector such as a spectrophotometer. When the property is of coloring, the detection may be conducted in a conventional way using a detector such as a spectrophotometer or microscope. In addition, when the analyte has a property of spin, the detection may be conducted in a conventional way using a detector such as an electron spin resonance apparatus according to a method as described in, for example, in "Enzyme Immunoassay" Protein, Nucleic Acid and Enzyme, Supplementary Volume 31, Edited by Tsunehiro Kitagawa, Toshio Nambara, Akio Tuji, and Eiji Ishikawa, pages 264-271, Kyoritsu Shuppan Co., Ltd., Published on Sep. 10, 1987. The detection may also be by fluorescence polarization.

The method for determining or identifying in the present invention may be conducted according to the above-mentioned per se known methods using reagents properly chosen in a per se conventional manner except for the additional step of performing the separation in the presence of the charged polymer, preferably performing both the separation and contact of the sample (the objective substance) and the affinity substance for forming a complex.

The presence of analyte in the sample can be identified, e.g., by detecting either a migration shift of labeled affinity molecule, a migration shift of the labeled conjugate of the affinity molecule, a migration shift of labeled analyte or its labeled analogue and/or its complex with the corresponding affinity molecule, or a migration shift of labeled analyte or its labeled analogue and/or its complex with its corresponding conjugate of the affinity molecule, or their combination. Also a migration shift of the complex of the analyte conjugated with a charged carrier molecule and the corresponding affinity molecule, or a migration shift of the complex of the analogue of the analyte conjugated with a charged carrier molecule and the corresponding labeled affinity molecule can be used to identify the presence of the analyte. Analysis of negative control samples, without analyte, can be run in the assay to determine such labeled molecule and/or its complex peak elution time or migration rate through the separation media. Positive control samples, containing a detectable amount of reference analyte, can be run in the assay to determine the labeled molecule and/or its complex peak elution time or migration rate through the separation media. When unknown samples are run in the same assay, the presence of analyte can be identified by detection of a peak with the same retention time or migration rate as the labeled molecule and/or its complex peak. To ensure that the identified peak is not just background noise in the assay, standard method validation techniques can be used to determine a threshold value of peak height or peak area giving statistical confidence that an actual signal has been detected over background.

Internal markers can be added to each sample to provide a frame of reference for identification of peaks or to adjust elution times for inter-assay variability allowing precise comparisons between assay runs. For example, detectable high molecular weight and low molecular weight markers can be added to samples to bracket the conjugate peaks in a frame of reference. If the elution times vary from run to run, conjugate peaks can still be identified by their relative positions between the internal markers, as is known by those skilled in the art.

The quantity of analyte present in a sample can be determined by comparison of the identified conjugate/analyte complex peak height or peak area to a standard curve. The standard curve can be, e.g., an equation representing the peak height or area values for one or more standard samples having known amounts of analyte. Peak height or area values from an unknown sample can be input to the formula to determine the amount of analyte in the sample. The peak height or area values can be adjusted by subtraction of a negative control background to increase the accuracy of the determination.

The analyte can be quantified by relating peak height ratios or peak area ratios for free conjugate and complex peaks to a formula or chart of values. The formula or chart of concentrations versus analyte concentrations can be calculated or empirically derived for the assay, as is known in the art. Addition of internal markers can improve the quantification data by comparing with results obtained from different run of assays with known amount of the analyte.

In carrying out the method of the invention, when a nucleotide chain is used and there is a possibility of the existence of a nuclease or nucleases such as DNase, RNase, etc., it is appropriate to add a nuclease inhibitor such as ethylene glycol bis(2-aminoethyl ether)tetraacetate (EGTA), ethylenediamine tetraacetate (EDTA), heparin, and the like to a solution containing a nucleotide chain.

Briefly, when the nucleotide chain is made to contact another substance (e.g., sample, affinity molecule or conjugate) or when the analyte/affinity substance complex is separated from the free affinity substance not involved in the formation of the complex, it is appropriate to add an inhibitor as mentioned above to a solution containing the nucleotide chain or a solution which is made to contact with the nucleotide chain in order to carry out the contact in the presence of the inhibitor.

The reagents and other materials used for conducting the present invention may be formulated into a composition or kit for separating a free conjugate of a charged carrier molecule and an affinity molecule, and a complex of an analyte in the sample and the conjugate so that the above-mentioned method of the present invention can successively be carried out. Specifically, the composition or kit for separating a free conjugate of a charged carrier molecule and an affinity molecule, and a complex of an analyte in the sample and the conjugate of the present invention comprises a separation media and a charged polymer. In a preferred embodiment of the above-mentioned composition or kit, the conjugate is labeled by a detectable marker. The charged carrier molecule in the conjugate is more preferably labeled by the detectable marker. The above-mentioned composition or kit of the present invention can further comprise the affinity molecule. In this case, at least one of the affinity molecule and the conjugate (e.g., the affinity molecule and/or the charged carrier molecule in the conjugate) is preferably labeled by the detectable marker. The preferred embodiment of examples of the respective components are as mentioned above. The above-mentioned composition or kit may be used in combination with a microfluidic device, which may be sold as part of the kit.

III. Concentration Method

In the present invention, concentration methods are performed for the purpose of concentrating an objective substance (e.g., an analyte of interest) in the sample by using a microfluidic device and applying a concentrated objective substance (e.g., an analyte of interest) of high concentration to the migration shift assay. A variety of concentration methods can be used in the microfluidic device to concentrate an objective substance in the sample, such as so-called on-line sample concentration techniques. The on-line sample concentration or sample stacking operations can be classified into two types: (i) electrophoretic concentration techniques which utilize a difference in electrophoretic mobilities of sample constituents in a capillary (e.g., FASS, FASI, ITP, IF, etc.) and (ii) chemical adsorption concentration techniques which utilize adsorbents (e.g., SPE, etc.) (R. L. Chien, Electrophoresis, 24, 486-497, 2003; the disclosure of which is incorporated in its entirety by reference herein).

For example, the following concentration methods can be used: (i) FASS (Field Amplification Sample Stacking) which utilizes the difference of the electrical conductivity of a concentration domain and a separation domain (e.g., patent application Ser. No. 10/206,386 for "Microfluidic Methods, Devices and Systems for In Situ Material Concentration", Weiss, D. J., Saunders, K., Lunte, C. E. *Electrophoresis* 2001, 22, 59-65; Britz-McKibbin, P., Bebault, G. M., Chen, D. D. Y. *Anal Chem.* 2000, 72, 1729-1735, Ross, D., Locascio, L. E. *Anal Chem.* 2002, 71, 5137-5145, the entire contents of which are incorporated by reference herein.), (ii) FASI (Field Amplification Sample Injection) whereby a minute plug of water is inserted between the concentration domain and the separation domain in the FASS (e.g., "Field amplified sample injection in high-performance capillary electrophoresis", Chien, R. L et al. *J. Chromatogr.* 1991, 559, 141-148, the entire contents of which are incorporated by reference herein), (iii) ITP (Isotachophoresis) which utilizes the difference of the mobilities of ions in the domain sandwiched between a leading solution and a trailing solution (e.g., Everaerts, F. M., Geurts, M. Mikkers, F. E. P., Verheggen, T. P. E. M *J Chromatagr.* 1976, 119, 129-155; Mikkers, F. E. P., Everaerts, F. M., Peek, J. A. F. *J. Chromatogr.* 1979, 168, 293-315; and Mikkers, F. E. P., Everaerts, F. M., Peek, J. A. F. *J. Chromatogr.* 1979, 168, 317-332, Hirokawa, T, Okamoto, H. Ikuta, N., and Gas, B., "Optimization of Operational Modes for Transient Isotachophoresis Preconcentration-CZE," Analytical Sciences 2001, Vol. 17 Supplement i185, the disclosures of which are incorporated in their entirety by reference herein), (iv) IF (Isoelectric Focusing) which utilizes the difference of the isoelectric point between the substances (e.g., "High performance isoelectric focusing using capillary electrophoresis instrumentation", Wehr T, et al. *Am. Biotechnol. Lab.* 1990, 8, 22, "Fast sand high-resolution analysis of human serum transferring by high-performance isoelectric focusing in capillaries", Kilar F. et al., *Electrophoresis* 1989, 10, 23-29, the entire contents of which are incorporated by reference herein.), (v) SPE (Solid Phase Extraction) which utilizes a specific interaction between a solid phase (e.g., a solid phase with bound adsorbent such as a receptor) and an objective substance to adsorb the objective substance to the solid phase (e.g., "Microchip-based purification of DNA from Biological Samples", Breadmore M. et al. *Anal. Chem.* 2003, 75, 1880-1886, the entire contents of which are incorporated by reference herein.).

IV. Concentration Methods of the Invention

The present invention provides methods comprising concentrating the objective substance which has not been concentrated efficiently by the above described known concentration methods with high concentration and detecting the objective substance in high sensitivity by reducing the interference in the objective operation (e.g., in the separation and the detection step) by any unnecessary constituents other than the analyte in the sample which are concentrated simultaneously with the objective substance (e.g., "noise constituents" which interfere in the detection of the objective substance). Further, the present invention also provides methods for optimizing the reaction conditions to easily concentrate the objective substance for the sensitive measurement of the objective substance.

It is a characteristic of the present invention that in the above-mentioned concentration methods a complex of the objective substance and the conjugate or a complex of the objective substance, conjugate and affinity molecule formed by contacting (e.g., reacting) the objective substance in the sample with an affinity molecule bound to a charged carrier molecule (e.g., a conjugate of the affinity molecule and the charged carrier molecule) is concentrated. That is, the concentration method of the present invention is accomplished for solving the below mentioned problems: a) When the objective substance in the sample has a very large molecular weight and/or a small electrical charge, the electrophoretic mobility of the objective substance becomes slow (e.g., is reduced). As a result, it is difficult to highly concentrate such an objective substance in a short time, e.g., concentrating such a substance efficiently becomes difficult. b) When unnecessary constituents (e.g., noise constituents) in the sample other than the objective substance migrate to the same region as the objective substance, the unnecessary constituents are concentrated simultaneously with the objective substance. As a result, when the concentrated sample including the objective substance is used as the sample for separation and detection, background and noise levels are elevated and reduction of the assay sensitivity results (e.g., the assay sensitivity is reduced). c) When the objective substance coexists with noise constituents in the sample such as fis the case with a clinical serum sample, it is very difficult to optimize reaction conditions so that the objective substance is concentrated while the unnecessary noise constituents are not concentrated simultaneously with the objective substance or are concentrated in a different region from the objective substance (e.g., in this case, optimization of the concentration step is very important for the sensitive detection. However, it is very time consuming and laborious to find such an optimum condition).

The methods of the present invention thus use a charged carrier molecule (e.g., a conjugate of the affinity molecule and the charged carrier molecule) which can efficiently concentrate an objective substance having a very large molecular weight and/or a relatively small charge into high concentration and can concentrate the objective substance at a migration region where the concentration of the unnecessary constituents (e.g., noise constituents) is lower or approximately zero, or at a migration region where the unnecessary noise constituents do not exist (e.g., a migration region where the concentration of noise constituents is lower or by controlling the migration mobility of the objective substance by choosing a suitable charged carrier molecule and optimizing the reaction conditions for concentrating the objective substance).

For example, when the objective substance is present in serum, the noise constituents (e.g., proteins which co-exist in the sample, etc.) are migrated and concentrate at the same region as the objective substance. The complex formed by reacting the objective substance and the affinity molecule/ charged carrier molecule conjugate, wherein the charged carrier molecule such as DNA is of suitable length (e.g., 50 to 3000 bp), is migrated and concentrated at a different region from the noise constituents in the serum (e.g., a region where the concentration of the noise constituents is lower or about zero).

In the present invention, the term "unnecessary constituents" (e.g., "noise constituents") generally refers to substances other than the objective substance which co-exist in the sample or a solution containing the objective substance, and which are migrated and concentrated at the same region as the objective substance and which interfere in the separation or the detection of the objective substance when the electrophoresis is done by conventional electrophoresis methods.

The unnecessary constituents (e.g., noise constituents) include, for example, proteins, nucleic acids, hemoglobin, metals, sugarbiological pigments, lipids, electrolytes and the like. "Unnecessary constituents" also generally refer to materials used in the labeling reaction of the affinity molecule or the analyte (or its analogue) and which remain in the labeled material preparations even after purification steps. It also generally refers to labeled affinity molecules which do not react with the analyte and which remain as an unbound form, or labeled analytes which do not react with the affinity molecule and which remain as an unbound form in the reaction mixture. The method of the present invention can be carried out, for example, in the following way(s). That is, a sample containing the analyte is contacted with a conjugate of an affinity molecule and a charged carrier molecule to form a complex of the analyte and the conjugate of an affinity molecule and a charged carrier molecule, and the resulting complex is migrated to the region of low or zero noise constituent concentration (e.g., a region with few noise constituents) and is concentrated by using a concentration (e.g., stacking) channel in a microfluidic device comprising at least one concentration channel having at least one microscale dimension of between about 0.1 and 500 microns. After that, by applying this complex to the migration shift assay, it is possible to identify the presence of the analyte or to determine an amount of the analyte in the sample by detecting the complex with high sensitivity.

A. Conjugate

By choosing a suitable charged carrier molecule in the conjugate of the invention, it is possible to control the migration property (e.g., mobility) of the objective substance. The conjugate may be labeled by a detectable marker as described above. The detectable marker, preferable examples of same, the labeling method used, etc. are the same as described above. In the methods mentioned above, in order to concentrate the analyte/conjugate complex or the analyte/conjugate/affinity molecule complex, a concentration (e.g., stacking) channel in a microfluidic device is used. In order to concentrate such molecules and their complexes in a microfluidic channel by means of the concentration methods exemplified above, such molecules to be concentrated are preferably diluted in a suitable buffer with suitable pH and ionic strength. For example, when a FASS concentration method is chosen, such molecules to be concentrated are diluted in low conductivity buffer, and then they are contacted and subjected to the concentration step. For example, a serum sample including an analyte of interest and a conjugate of an affinity molecule which recognizes the analyte specifically and the charged molecule are diluted 10 times by 7.5 mM HEPES buffer (pH7.5) including 7.5 mM NaCl.

B. Sample and Objective Substance

The sample and the objective substance are the same as described above. Especially, the concentration method of the present invention is useful for an analyte which is migrated and concentrated at the same region as the noise constituents and for an analyte which generates a complex together with an affinity molecule and/or its conjugate and which migrates and is concentrated at the same region as the noise constituents using conventional methods. In order to concentrate such analyte and its complex in a microfluidic channel efficiently, by means of the concentration methods exemplified above, such an analyte to be concentrated is preferably diluted in a suitable buffer with suitable pH and ionic strength. For example, when a FASS concentration method is chosen, the analyte to be concentrated is diluted in low conductivity buffer and then contacted and subjected to the concentration step. For example, serum including an analyte of interest is diluted 10 times with 7.5 mM HEPES buffer (pH7.5) including 7.5 mM NaCl.

C. Contacting the Sample with a Conjugate

The contacting step is performed for contacting the sample containing the analyte with the conjugate of the affinity molecule and the charged carrier molecule to form a complex of the analyte and the conjugate of the affinity molecule and the charged carrier molecule. There is no limitation in terms of how such a complex may be formed. For example, a sample containing an analyte and a conjugate of the affinity molecule and the charged carrier molecule can be dissolved, dispersed or suspended, respectively, e.g., in water or buffers such as Tris-buffer, phosphate buffer, Veronal buffer, borate buffer, Good's buffer, SSC buffer, TBE buffer, TAE buffer and the like to give liquid materials, and these liquid materials can be mixed and contacted with one another. Alternatively, the sample and conjugate of the affinity molecule and the charged carrier molecule may be dissolved, dispersed or suspended together at once. In the case where a sample containing an analyte is a liquid, a conjugate of the affinity molecule and the charged carrier molecule can be directly mixed with the sample. If the sample containing an analyte is a liquid, as described above, it may not be dissolved, dispersed or suspended, e.g., in water or the buffers. In the above-mentioned method, a concentration of the buffer is selected from the range usually used in the field of the present invention. The pH of the buffer is also selected from the range usually used in the field of the present invention. For example, when a mixture of a sample and a conjugate of an affinity molecule and a charged carrier molecule are concentrated by a FASS method, the contacting step is preferably carried out in a buffer of lower conductivity. Further, when the concentration method is conducted by a FASS method, it is preferable to use a buffer having low electrical conductivity such as a lower concentration of Hepes, Taps and Tris buffer with lower salt concentration, and the like.

It is generally difficult to optimize the pH and the temperature for contacting the sample with the affinity molecule, in other words, for forming a complex of the analyte and the affinity molecule, since they depend on the properties of the analyte and the affinity molecule, and the reaction conditions also affect the concentration efficiency. However, in the method of the present invention, as far as they do not disturb the formation of the complex, the reaction conditions may be chosen according to a conventional manner usually used in the field of the present invention, e.g., known EIA, RIA, FIA or hybridization assays. That is, the contacting step may be conducted usually at a pH between about 2 to 10, preferably at a pH between 5 to 9, and usually at a temperature of between 0 to 90° C., preferably between 5 to 40° C. The reaction may be conducted for a period of a few seconds to several hours depending on the respective properties of the analyte and the conjugate of the affinity molecule and the charged carrier molecule, since the reaction time required for formation of the complex is varied depending on their properties.

D. Affinity Molecule

In the present invention, one or more additional affinity molecule(s) (e.g., an affinity molecule which has not been bound to the charged carrier molecule) can be used. One of the purposes for using one or more additional affinity molecules is to make the separation and detection of the objective substance easier. The characteristics of the additional affinity molecule(s), examples of such molecules, the concentration to be used, etc. are the same as described above. The additional affinity molecule(s) may be labeled by a detectable marker as described above. The detectable marker, preferable examples of same, the labeling method used, etc. are the same as described above.

E. Use of Conjugate and Affinity Molecule

When a conjugate and an affinity molecule are used, the sample containing the analyte is contacted with an affinity molecule and an affinity molecule/charged carrier molecule conjugate to form a complex of the analyte, the affinity molecule and the conjugate, and the resulting complex is concentrated by using a concentration (e.g., stacking) channel in a microfluidic device comprising at least one concentration (e.g., stacking) channel.

In the present invention, two or more affinity molecules and two or more conjugates can be used. In such case, each affinity molecule (including the affinity molecule in each conjugate) binds with the objective substance at a different site on the objective substance from every other affinity molecule. In case of using both the affinity molecule and the conjugate, at least one of the affinity molecule and the conjugate is generally one which can be measured (e.g., detected) or labeled by a detectable marker by some conventional method. The use of an affinity molecule or a conjugate having such a property will make it easier to measure an analyte in a sample. In the case where an analyte itself can be detected by some method (e.g., an enzyme or the like), or where an analyte can bind directly to a detectable marker without an affinity molecule or a conjugate, the analyte in the sample can be measured, even if the affinity molecule and the conjugate possess no such detectable property described above. When two or more affinity molecules or two or more conjugates are used, it is not necessary for all affinity molecules or all conjugates to have such a detectable property. In the above-mentioned method, the detectable marker, the method used to label an affinity molecule or a conjugate by the detectable marker, etc. are as described above.

In order to contact the sample containing the analyte with the affinity molecule and the conjugate to form a complex of the analyte, the affinity molecule and the conjugate, there is no limitation as far as how such a complex can be produced. For example, a sample containing an analyte, an affinity molecule and a conjugate can be dissolved, dispersed or suspended, respectively, e.g., in water or buffers such as tris-buffer, phosphate buffer, Veronal buffer, borate buffer, Good's buffer, SSC buffer, TBE buffer, TAE buffer and the like to give liquid materials, and these liquid materials can be mixed and contacted with one another. Alternatively, the sample, affinity molecule and conjugate may be dissolved, dispersed or suspended together at once. In the case where a sample containing an analyte is a liquid, an affinity molecule and/or a conjugate can be directly mixed with the sample. If the sample containing an analyte is a liquid, as described above, it may not be dissolved, dispersed or suspended, e.g., in water or the buffers.

In the above-mentioned method, a concentration of the buffer is selected from the range usually used in this field. The concentration of the affinity molecule and the conjugate in the step of contacting the sample with the affinity molecule and the conjugate is as mentioned above. The reaction conditions (e.g., pH, temperature, reaction time, etc.) are the same as the above-mentioned condition of the contacting the sample and the affinity molecule.

F. Charged Polymer

In the concentration method of the present invention, the above-described charged polymer may be also used. Because a charged polymer which can bind to interfering constituents can prevent, e.g., false positive migration shifts due to non-specific binding of constituents to the conjugate or the conjugate and the affinity molecule, or failed assays due to formation of an insoluble complex with the conjugate or the conjugate and the affinity molecule/constituent complexes, it is preferable to use a charged polymer in the concentration method of the present invention. The charged polymer, its characteristics, examples of same, the concentration to be used, etc. are the same as described above. When the charged polymer is used, the analyte/conjugate complex or analyte/conjugate/affinity molecule complex may be concentrated in the presence of the charged polymer.

For example, the charged polymer is preferably present in a concentration (e.g., stacking) channel of a microfluidic device comprising at least one concentration channel. Specifically, it is preferable to add the charged polymer to the concentration (e.g., stacking) media packed in the concentration channel. The presence of the charged polymer in the concentration media can reduce carry-over of interfering sample constituents between sample runs. Alternatively or additionally, the charged polymer may be present in the solution (e.g., water, a buffer such as tris-buffer, phosphate buffer, Veronal buffer, borate buffer, Good's buffer, SSC buffer, TBE buffer, TAE buffer, etc., used in hybridization assays, immunoassays, and the like) containing the analyte and the analyte/conjugate complex or analyte/conjugate/affinity molecule complex, and the obtained solution containing the charged polymer, the analyte and the analyte/conjugate complex or analyte/conjugate/affinity molecule complex is then applied to the concentration channel. Further, the charged polymer may be present in a solution to be used for applying a solution containing the analyte and the analyte/conjugate complex or analyte/conjugate/affinity molecule complex to the microfluidic device, e.g., an eluent and a running buffer to be used in the concentration (e.g., water, a buffer such as tris-buffer, phosphate buffer, Veronal buffer, borate buffer, Good's buffer, SSC buffer, TBE buffer, TAE buffer, etc., used in hybridization assays, immunoassays, and the like). In the methods mentioned above, the method for making the charged polymer present in the solution containing the analyte and the analyte/conjugate complex or analyte/conjugate/affinity molecule complex is the same as described above.

Further, in the concentration method of the present invention, for reasons as described above, the charged polymer is preferably present in at least the concentration step (e.g., in the concentration media), but it additionally and/or alternatively may be present in the contacting step of the sample containing the analyte with the conjugate or the conjugate and the affinity molecule for forming the complex. In a preferred embodiment of the invention, the charged polymer is present in both the concentration step (e.g., in the concentration media) of the analyte/conjugate complex or the analyte/conjugate/affinity molecule complex and the contacting step of the sample containing the analyte and the conjugate or the conjugate and the affinity molecule for forming the complex to increase the recovery of objective substance existing in the sample.

In the methods mentioned above, the method for making the charged polymer present in the contacting step of the sample and the conjugate or the contacting step of the sample, the conjugate and the affinity molecule is the same as described above. The concentration of the charged polymer to be used, etc. is the same as described above.

G. Concentration Procedure

The resulting complex of the analyte (or the analogue) and the conjugate, complex of the analyte (or the analogue), the conjugate and the affinity molecule or complex of the analyte (or the analogue), the charged carrier molecule and the affinity molecule is concentrated. Typical examples are an on-line sample concentration or sample stacking operations such as an electrophoretic concentration utilizing a difference in an electrophoretic mobility in a capillary (e.g., FASS, FASI, ITP, IF, etc.), a chemical adsorption concentration utilizing an adsorbent (e.g., SPE, etc.) and the like. In particular, an electrophoretic concentration may preferably be used. (R. L. Chien, Electrophoresis, 24, 486-497, 20031 the disclosure of which is incorporated in its entirety by reference herein).

Among the electrophoretic concentration methods, the methods (e.g., ITP, FASS, FASI, etc.) based on so-called electrokinetic focusing are preferable. Such methods are, for example, based on the following principles. By choosing and using a suitable buffer so that the electrophoretic mobility of the objective substance to be concentrated in the buffer zone for the migration in the concentration channel becomes slower than that in a solution zone before being applied to the concentration channel containing the objective substance, when the objective substance moves to the boundary between the solution zone containing the objective substance and the buffer zone for the migration in the concentration channel, the migration speed of the objective substance is slowed down at the boundary and the objective substance is concentrated (e.g., R. L. Chien, Electrophoresis, 24, 486-497, 2003, R. L. Chien, D. S. Burgi, Anal. Chem., 64, 489A, 1992, D. S. Burgi, R. L. Chien, Anal. Chem., 63, 2042, 1991, R. L. Chien, D. S. Burgi, J. Chromatogr., 559, 141, 1991, the disclosures of which are incorporated in their entirety by reference herein). For performing the concentration method of the present invention by using the above-mentioned method, the concentration of the resulting complex of the analyte (or the analogue) and the conjugate, complex of the analyte (or the analogue), the conjugate and the affinity molecule or complex of the analyte (or the analogue), the charged carrier molecule and the affinity molecule is conducted by using a buffer for the migration in the concentration channel, wherein the buffer has a property that the electrophoretic mobility of the complex [e.g., analyte (or analogue)/conjugate complex, analyte (or analogue)/conjugate/affinity molecule complex or analyte (or analogue)/charged carrier molecule/affinity molecule complex] in the buffer for the migration in the concentration channel is slower than that in a solution which contains the complex being applied to the concentration step. As a result, when the complex moves to the boundary between the solution containing the complex and the buffer for the migration in the concentration channel, the migration speed of the complex is slowed down at the boundary and the complex is concentrated. Among them, more particularly, it is preferable to use FASS, ITP, for example, based on the following principle. ITP is a method based on the principle that by placing the objective substance between two ions, a leading ion of an electrophoretic mobility faster than the objective substance and a trailing ion of an electrophoretic mobility slower than the objective substance, the objective substance is concentrated. And FASS is a method based on the principle that electrophoretic mobility of the objective substance is reduced when the substance in the concentration domain reaches the boundary of a separation domain and a concentration domain and then the substance is concentrated, wherein the separation domain has higher conductivity than the concentration domain (e.g., patent application Ser. No. 10/206,386 for "Microfluidic Methods, Devices and Systems for In Situ Material Concentration", Weiss, D. J., Saunders, K., Lunte, C. E. *Electrophoresis* 2001, 22, 59-65; Britz-McKibbin, P., Bebault, G. M., Chen, D. D. Y. *Anal Chem.* 2000, 72, 1729-1735, Ross, D., Locascio, L. E. *Anal Chem.* 2002, 71, 5137-5145). Among the concentration methods mentioned above, it is preferable to use the concentration method in which the complex is concentrated based on the charge of the charged carrier molecule in the conjugate bound with the analyte.

In the present invention, all of the buffers, fillers, a variety of reagents such as processing solutions, etc., conventionally used in the concentration methods as mentioned above may be utilized. The concentration of these materials may be chosen optionally according to known concentration methods. The condition for concentration (e.g., pH, temperature, applied voltage, time, and so on) may properly be chosen according to known methods.

Analytes of interest can be stacked (e.g., concentrated) into a volume less than the original analyte sample by isotachophoresis (ITP) in a microfluidic device. For example, a sample bolus can be loaded between two different buffer systems in a channel and exposed to an electric current to create a steady state of solute zones migrating in order of decreasing mobility. In the steady state, the zones can adopt the same concentration and migrate along the channel at the same velocity as the leading electrolyte. Alternatively, a sample bolus can be loaded adjacent to an electrolyte and stacked in a dynamic (e.g., transient) condition at the interface for injection, e.g., without having reached a steady state equilibrium between ITP electrolytes. Stacking can be practiced, e.g., in a concentration (e.g., stacking) channel of a microfluidic device wherein a sample is loaded between channel regions of a trailing electrolyte and a leading electrolyte.

Figure 8A:
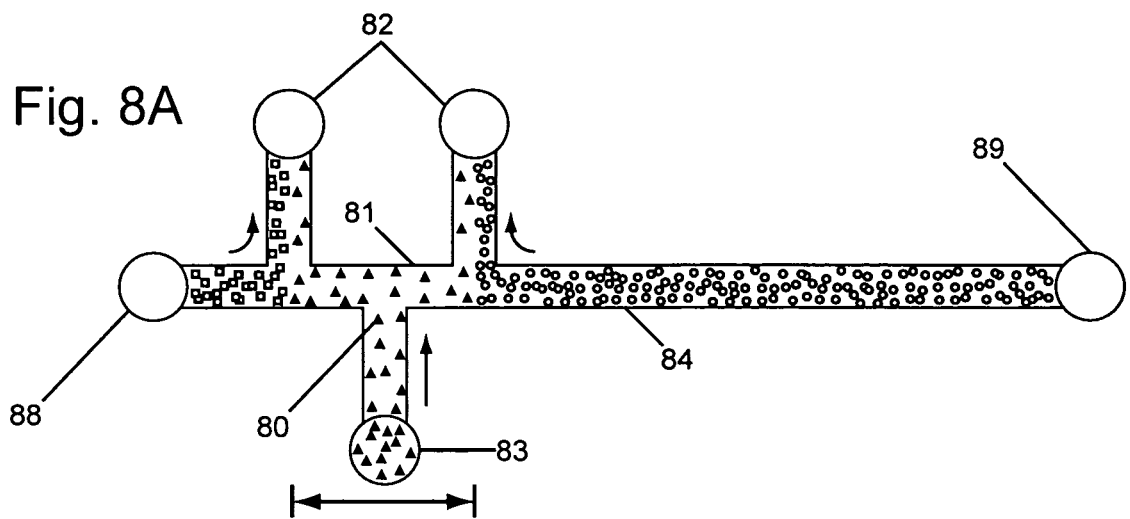
FIG. 8 is a schematic diagram of an isotachophoresis microfluidic system.
Figure 8B:
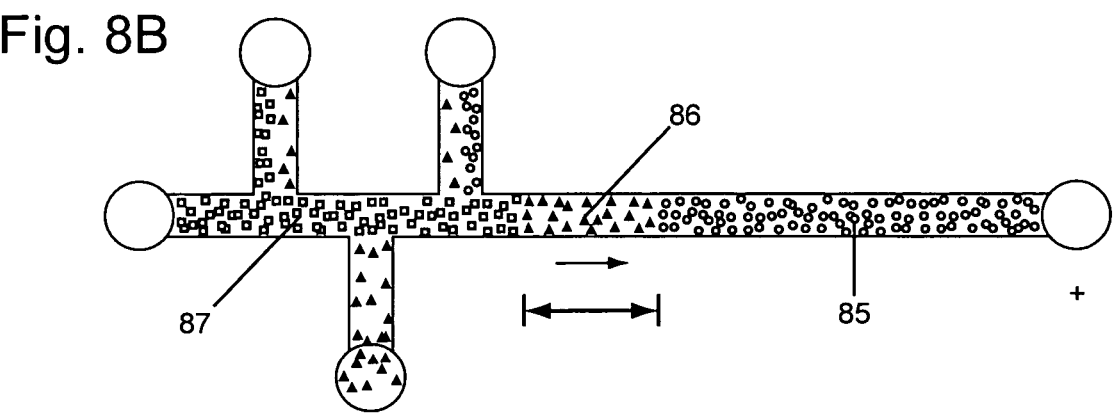
Figure 8C:
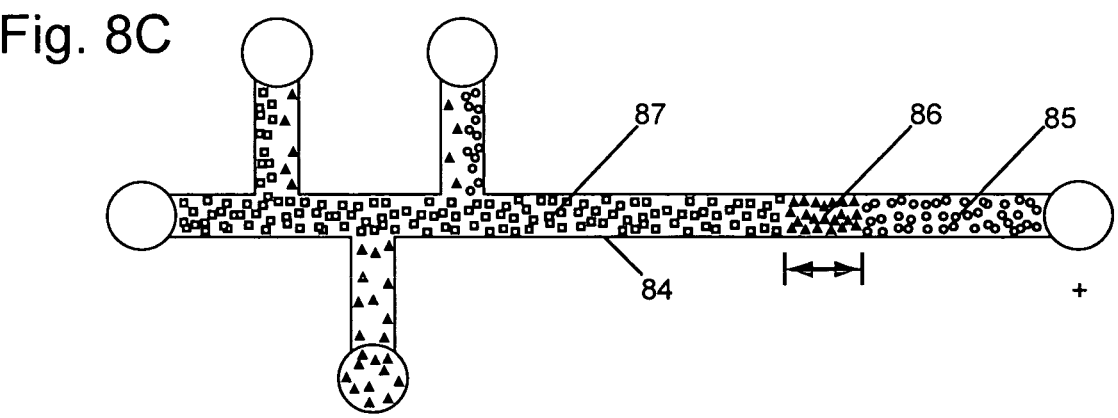

As shown in FIG. 8A, analyte sample 80 can be loaded to loading channel segment 81 by a differential pressure between vacuum well 82 and sample well 83. When an electric field is applied across stacking (e.g., concentration) channel segment 84, current is carried by high mobility (e.g., high charge to mass ratio) leading electrolytes 85, intermediate mobility analytes 86, and low mobility trailing electrolyte 87, as shown in FIG. 8B. As ITP proceeds, a steady state can be established in which the volume of analyte 86 is reduced to the point where the concentration of charged analyte 86 is equivalent to the concentration of leading electrolyte 85. In the steady state, the stacked analyte solution migrates along stacking channel segment 84 at the same rate as the leading 85 and trailing 87 electrolytes, as shown in FIG. 8C, with the electrolytes and charged analytes carrying the same amount of electric current per unit volume in the stacking channel segment. Factors such as charge density and transient differential migration rates of the analytes and electrolytes, tend to focus the analytes and electrolytes into zones during ITP. Stacking channel segments of the invention can be any size including microscale channels having a dimension, such as width or depth, ranging from about 500 µm to about 0.1 µm, or from about 100 µm to about 1 µm, or about 10 µm.

Figure 9A:
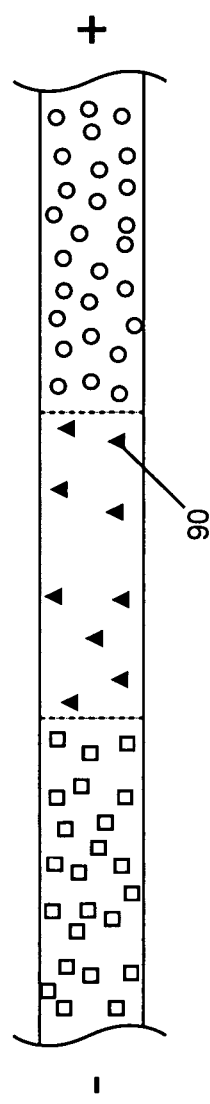
FIG. 9 is a schematic diagram of transient ITP concentrating an analyte at an interface with a leading electrolyte.
Figure 9B:
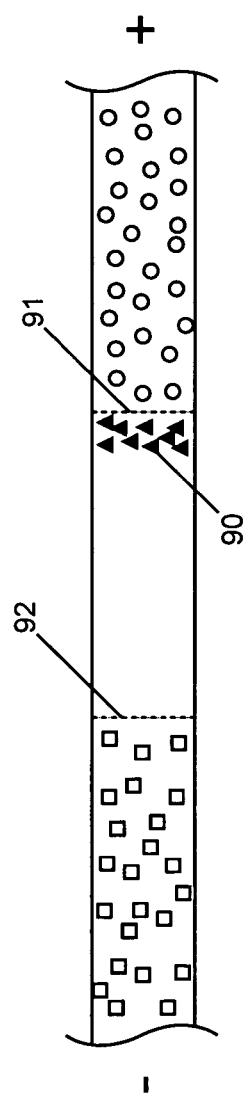
Figure 10A:
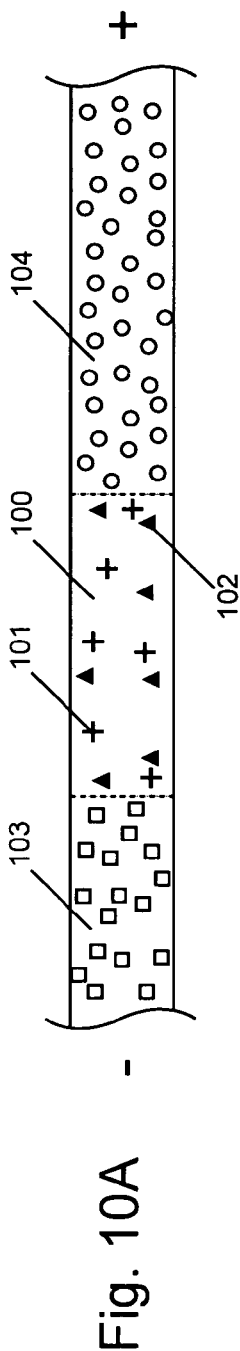
FIG. 10 is a schematic diagram of transient ITP separation of analytes of interest and steady state ITP juxtaposition of the analytes.
Figure 10B:
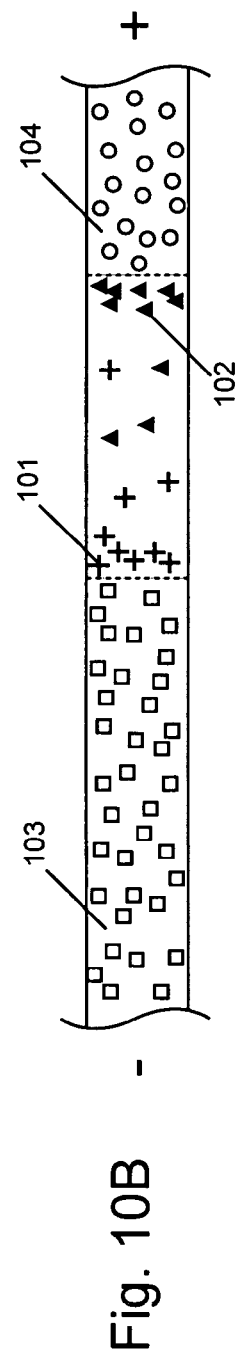
Figure 10C:
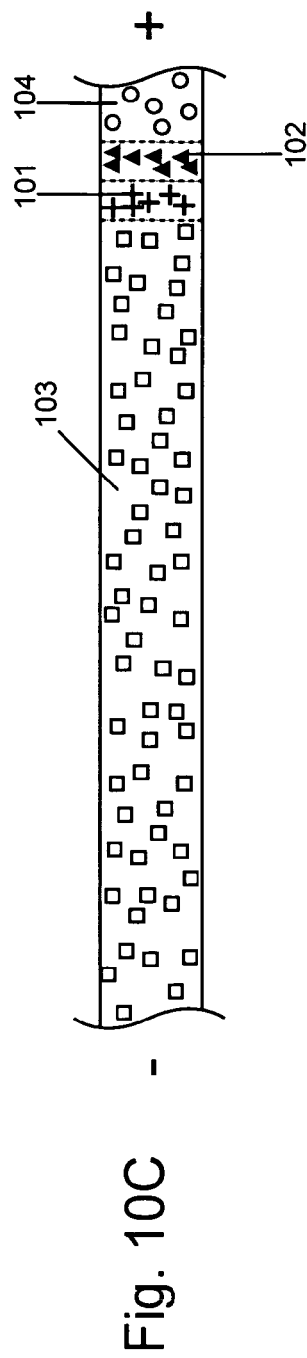

Stacking can also be practiced in a transient state. For example, as shown in FIG. 9A, initially dilute and dispersed analyte molecules 90 can accumulate, e.g., at leading electrolyte interface 91 as shown in FIG. 9B. This concentration of analyte at an interface can occur before establishment of steady state uniform analyte and electrolyte carrier concentrations. Optionally, an analyte can accumulate in a transient state, e.g., during initial application of an electric field in ITP, at trailing electrolyte interface 92. In other embodiments of transient ITP, analytes can become concentrated in zones other than interfaces of ITP electrolytes. Multiple analytes of interest can accumulate in a steady state or transient state, e.g., at one or both of the electrolyte interfaces. For example, as shown in FIGS. 10A to 10C, sample solution 100 with first analyte of interest 101 and second analyte of interest 102 can be loaded between trailing electrolyte solution 103 and leading electrolyte solution 104. In the case where the first analyte has a slower mobility than the second analyte, but a faster mobility than the trailing electrolyte, the first analyte can accumulate at the interface with the trailing electrolyte in the presence of an electric field. Meanwhile, in the transient state, as shown in FIG. 10B, the second analyte, with somewhat higher mobility than the first analyte, can accumulate at the other end of the sample bolus along the interface with the faster mobility leading electrolyte. Such a situation can provide the opportunity for separate sequential or parallel application of the first and second analytes to one or more separation channel segments, as can be appreciated by those skilled in the art. Once a steady state has been established during ITP, as shown in FIG. 10C, charged first and second analytes can become compressed into narrow adjacent bands, e.g., for application together for resolution in a separation channel segment.

In methods of the invention, the mobilities of trailing electrolytes and leading electrolytes can be adjusted to provide selective pre-concentration of an analyte of interest while separating sample constituents not of interest from the analyte. For example, as shown in FIG. 11A, sample solution 110 containing analyte of interest 111, slow mobility sample constituent not of interest 112, and fast mobility sample constituent not of interest 113, can be loaded between trailing electrolyte 114 and leading electrolyte 115. When an electric field is applied to the channel, slow mobility sample constituents not of interest 112 can fall behind the trailing electrolytes while fast mobility sample constituents not of interest 113 can race ahead of the leading electrolytes, as shown in FIG. 11B. Continued ITP to a steady state can, e.g., further separate sample constituents not of interest from the analyte, as shown in FIG. 11C. Removal of sample constituents not of interest from analytes of interest can provide an improved injection material for separation in a separation channel segment. After samples have been pretreated by ITP to remove sample constituents not of interest, analyses of analytes of interest applied to a separation channel segment can have, e.g., reduced background noise, higher resolution due to lower injection volumes, more accurate quantitation due to better baselines and fewer overlapping peaks, etc.

Trailing electrolytes and leading electrolytes can be tailored, according to methods known in the art, by adjusting electrolyte mobilities to provide highly specific retention and stacking (e.g., concentrating) of analytes of interest, while sample constituents not of interest are removed. In one embodiment, the pH of electrolytes is selected to bracket the pK of an analyte of interest so that sample constituents not of interest having pKs outside the bracket will be removed in the ITP. The pK of the analytes of interest can be determined, e.g., empirically or based on the known molecular structure of the analytes. In other embodiments, the analyte of interest can be, e.g., closely bracketed between selected trailing and leading electrolyte compositions known to have slower and faster mobilities than the analyte. Many ions and buffers can be used in electrolytes to bracket analytes, such as, e.g., chloride, TAPS, MOPS, and HEPES. Optionally, the mobility of electrolytes and/or analytes can be modulated by adjusting the viscosity or size exclusion characteristics of the sample solution, trailing electrolyte solution, and/or leading electrolyte solution. In another option for adjusting the mobility of ITP solutions, mobility of analyte solutions and/or electrolyte solutions can be moderated, particularly during transient ITP migrations, by adjusting the concentration, ionic strength, or conductivity of the solutions. The temperature of solutions can be selected in still other options to adjust the mobility of analytes, electrolytes, or ITP solutions.

A variety of immunochemical assay techniques known in the art can be used in practicing the present invention to concentrate for detecting an analyte of interest in the sample, such as antibody sandwich assays and enzyme-linked immunoassays (see, e.g., Bolton et al., Handbook of Experimental Immunology, Weir, D. M., Ed., Blackwell Scientific Publications, Oxford, 1986, vol. 1, Chapter 26, for a general discussion on immunoassays), and other similar assay formats known to those of ordinary skill in the art. For example, in the assay format described above and shown in FIGS. 3A to 3K, the present invention may be used to concentrate a complex comprising an analyte or an analogue of the analyte and a conjugate.

Specific examples of the sandwich assay format shown in the above-mentioned FIGS. 3A to 3F are as follows: (a) A method for concentrating an analyte in a sample is disclosed, which comprises: (i) contacting the sample containing the analyte with one or more conjugates of an affinity molecule and a charged carrier molecule, wherein at least one of the one or more conjugates is labeled by a detectable marker, to form a complex containing the analyte and the conjugate labeled by the detectable marker; (ii) concentrating the complex in a concentration channel of a microfluidic device; wherein the affinity molecule in the conjugate has a property capable of binding to the analyte, and when two or more conjugates are used, each affinity molecule in the conjugate has a property capable of binding with the analyte at a different site on the analyte from every other affinity molecule, and the charged carrier molecule has a property capable of causing a change in a migration property of the analyte by binding to the analyte through the affinity molecule to form a complex of the analyte, the affinity molecule and the charged carrier molecule.

(b) A method for concentrating an analyte in a sample is disclosed, which comprises: (i) contacting the sample containing the analyte with one or more affinity molecules and one or more conjugates of an affinity molecule and a charged carrier molecule, wherein either at least one of the affinity molecule or at least one of the conjugate is labeled by a detectable marker, to form a complex containing the analyte, the affinity molecule and the conjugate; (ii) concentrating the complex in a concentration channel of a microfluidic; wherein the affinity molecule and the affinity molecule in the conjugate have a property capable of binding to the analyte, and each affinity molecule has a property capable of binding with the analyte at a different site on the analyte from every other affinity molecule, and the charged carrier molecule has a property capable of causing a change in a migration property of the analyte by binding to the analyte through the affinity molecule to form a complex of the analyte, the affinity molecule and the charged carrier molecule.

Specific examples of the competitive assay format shown in the above-mentioned FIGS. 3G to 3K are as follows: (a)

A method for concentrating an analyte in a sample is disclosed, which comprises: (i) contacting the sample containing the analyte with the analyte (or the analogue) labeled by a detectable marker and one or more conjugate of an affinity molecule and a charged carrier molecule to form a first complex of the analyte and the conjugate and a second complex of the labeled analyte (or the labeled analogue) and the conjugate; (ii) concentrating the second complex; wherein the affinity molecule in the conjugate has a property capable of binding to the analyte in the sample and the labeled analyte or the analyte in the sample and the labeled analogue, and when two or more conjugates are used, each affinity molecule in the conjugate has a property capable of binding with the analyte in the sample and the labeled analyte at a different site on the analyte in the sample and a different site on the labeled analyte from every other affinity molecule or each affinity molecule in the conjugate has a property capable of binding with the analyte in the sample and the labeled analogue at a different site on the analyte in the sample and a different site on the labeled analogue from every other affinity molecule, and wherein the charged carrier molecule has a property capable of causing a change in a migration property of the labeled analyte or the labeled analogue by binding to the labeled analyte or the labeled analogue through the affinity molecule to form a complex of the labeled analyte or the labeled analogue, the affinity molecule and the charged carrier molecule.

(b) A method for concentrating an analyte in a sample is disclosed, which comprises: (i) contacting the sample containing the analyte with the analyte (or the analogue) labeled by a detectable marker, one or more affinity molecule and one or more conjugate of an affinity molecule and a charged carrier molecule to form a first complex of the analyte, the affinity molecule and the conjugate and a second complex of the labeled analyte (or the labeled analogue), the affinity molecule and the conjugate; (ii) concentrating the second complex; wherein the affinity molecule and the affinity molecule in the conjugate have a property capable of binding to the analyte in the sample and the labeled analyte or the analyte in the sample and the labeled analogue, and each affinity molecule has a property capable of binding with the analyte in the sample and the labeled analyte at a different site on the analyte in the sample and a different site on the labeled analyte from every other affinity molecule or each affinity molecule has a property capable of binding with the analyte in the sample and the labeled analogue at a different site on each of the analyte in the sample and a different site on the labeled analogue from every other affinity molecule, and wherein the charged carrier molecule has a property capable of causing a change in a migration property of the labeled analyte or the labeled analogue by binding to the labeled analyte or the labeled analogue through the affinity molecule to form a complex of the labeled analyte or the labeled analogue, the affinity molecule and the charged carrier molecule.

(c) A method for concentrating an analyte in a sample is disclosed, which comprises: (i) contacting the sample containing the analyte with the analyte bound to a charged carrier molecule (or the analogue bound to a charged carrier molecule), one or more affinity molecule labeled by a detectable marker to form a first complex of the analyte bound to the charged carrier molecule (or the analogue bound to a charged carrier molecule) and the labeled affinity molecule and a second complex of the analyte and the labeled affinity molecule; (ii) concentrating the first complex; wherein the affinity molecule has a property capable of binding to the analyte in the sample and the analyte bound to the charged carrier molecule or the analyte in the sample and the analogue bound to the charged carrier molecule, and wherein when two or more affinity molecules are used, each affinity molecule has a property capable of binding with the analyte in the sample and the analyte bound to the charged carrier molecule at a different site on the analyte in the sample and a different site on the analyte bound to the charged carrier molecule from every other affinity molecule or each affinity molecule has a property capable of binding with the analyte in the sample and the analogue bound to the charged carrier molecule at a different site on the analyte in the sample and a different site on the analogue bound to the charged carrier molecule from every other affinity molecule, and wherein the charged carrier molecule has a property capable of causing a change in a migration property of the first complex by binding to the analyte or the analogue to form a complex of the analyte, the affinity molecule and the charged carrier molecule.

H. Microfluidic Device

In the present invention, a concentration of analyte/conjugate complex or analyte/conjugate/affinity molecule complex can be conducted by using a microfluidic system generally including a microfluidic device based on the above-mentioned concentration methods. The microfluidic device to be used in the concentration method of the present invention has at least one or more concentration (e.g., ITP stacking) channels which may contain a concentration media. It is preferable to use a microfluidic device in the concentration method of the present invention having at least one or more concentration channels which may contain a concentration media and a channel fluidically connected to the concentration channel. The concentration channel and the channel fluidically connected to the concentration channel have the same characteristics as that of the separation channel described above. When the separation and measurement of the objective substance is performed consecutively after carrying out the concentration method of the present invention, it is preferable to use the microfluidic device further including one or more separation channel, sample loading channel, sample mixing channel, detector, etc. as described above.

I. Concentration Media

The concentration media may be the same as the separation media described above. The concentration media is suitably selected according to the concentration method to be used. The concentration of the concentration media to be used is suitably selected from the range mentioned above according to the concentration method to be used. It is not necessary to use such concentration media, depending on the concentration method to be used.

J. Separation and Detection

The resulting concentrated analyte in the sample (e.g., the complex comprising the analyte or the analogue of the analyte and the conjugate) is applied to the migration shift assay described above. By applying the analyte concentrated by the concentration method of the present invention to the migration shift assay, it is possible to measure (e.g., identify or detect) the analyte with high sensitivity. The analyte concentrated by the concentration method of the present invention can be used with any migration shift assay described above. That is, the resulting concentrated complex comprising the objective substance and the conjugate of the charged carrier molecule and the affinity substance (e.g., the analyte/conjugate complex or the analyte/affinity molecule/conjugate complex) is separated from the free affinity substance not involved in the formation of the complex (e.g., the affinity molecule and/or the conjugate) based on the difference in the migration rate between the complex and the free affinity substance. And then, the analyte/affinity substance complex (or the analyte/conjugate complex or the analyte/affinity molecule/conjugate complex) or the free affinity substance (e.g., free affinity molecule and/or free conjugate) which is not involved in forming the complex separated by the above-mentioned separation method can be measured or detected by a method corresponding to the properties of the detectable property of the molecules involved (e.g., the detectable marker associated therewith). Thus, the amount of the analyte in a sample can be determined or the presence of the analyte in the sample can be identified. That is, the analyte/conjugate complex is separated from the free conjugate which is not involved in the formation of the complex, or the analyte/affinity molecule/conjugate complex is separated from the free affinity molecule and/or conjugate which is not involved in the formation of the complex, according to the above-mentioned separation. The resulting complex, or free affinity molecule and/or free conjugate may be measured or detected by a method corresponding to the properties of these (e.g., the detectable marker). The separation procedure, separation media, detection, etc. is the same as the described above.

If the analyte concentrated by the concentration method of the present invention is applied to the separation and detection method of the present invention described above, highly sensitive and accurate measurement of the objective substance can be achieved. When the analyte concentrated by the concentration method of the present invention is applied to the migration shift assay, the principle of the migration shift assay to be applied may be the same as the principle of the concentration method for concentrating the analyte or may differ from the principle of the concentration method for concentrating the analyte. In order to separate and measure the objective substance with high accuracy, it is preferable that the principle of the migration shift assay differs from the principle of the concentration method for concentrating the analyte. For example, when ITP is used for concentrating the analyte, the migration shift assay for separating and measuring is suitably selected from methods other than ITP such as FASS, FASI, IF and the like.

A specific, non-limiting example of the method mentioned above is as follows: a method of detecting or identifying an analyte of interest in a sample is disclosed, which comprises: (i) contacting the sample containing the analyte with one or more a conjugate of an affinity molecule and a charged carrier molecule to form a complex of the analyte and the conjugate; (ii) concentrating the complex by using a concentration channel in a microfluidic device comprising at least one concentration channel having at least one microscale dimension of between about 0.1 and 500 microns; (iii) separating the complex and any unbound conjugate, if necessary in the presence of a charged polymer, by using a separation channel in a microfluidic device comprising at least one separation channel having at least one microscale dimension of between about 0.1 and 500 microns; and (iv) detecting the complex to identify the presence of the analyte or to determine an amount of the analyte in the sample; wherein the charged polymer reduces interference with detecting; and wherein the charged carrier molecule causes a change in a migration property of the analyte by binding to the analyte through the affinity molecule to form a complex of the analyte, the affinity molecule and the charged carrier molecule.

The following non-limiting Examples illustrate the various uses and methods of the present invention to reduce interference in migration shift assays.

EXAMPLE

Example 1

The following non-limiting Example illustrates the use of heparin sulfate as the charged polymer for blocking serum interference in an alpha-feto protein immunoassay.

Reagents:

Gel: 2.5% pDMA/3% glycerol/0.05% Tween20/0.1% BSA/150 mMHEPES/NaCl/2.5 mg/ml LCA (pH: 7.5).

Buffer for serum samples (hereinafter abbreviated as sample buffer): 7.5 mM HEPES/0.025% Tween-20/0.1% BSA+20 nM anti-AFP monoclonal antibody WA-2 IgG (pH: 7.5). The monoclonal antibody was prepared in house.H. Katoh et al., Anal. Chem. (1998) 70, 2110-2114).

Buffer for antibody (hereinafter abbreviated as antibody buffer): 7.5 mM HEPES/NaCl/0.025% Tween-20/0.01% BSA (pH: 7.5).

Labeled anti-AFP antibody/DNA conjugate: 3 nM of 4Alexa Fluor 647 anti-AFP monoclonal antibody WA-1-140 bp DNA conjugate; Alexa Fluor 647 dye was purchased from Molecular Probes, Inc. (Eugene, Oreg.), and the DNA charged carrier molecule was prepared by PCR reaction. The anti-AFP monoclonal antibody WA-1 recognizes a different epitope of AFP from WA-2. The conjugate was prepared according to the methods described in Japanese Patent Application number WO 02/082083 which has previously been incorporated by reference herein. The monoclonal antibody was prepared in house (H. Katoh et al, Anal. Chem. (1998) 70, 2110-2114). The 140 bp DNA was prepared as follows: PCR reaction was carried out by employing a synthesized sequence of 5'-GGTTAGCAACTTACTACCG-GATTTTG-3' as a forward primer, a synthesized sequence of 5'-CCTAGCAAACTCGGAAGATTTTTTCAGA-3' as a reverse primer and lambda DNA (from New England Bio Labs, Inc., Beverly, Mass.) as a template. The annealing temperature was 60 degrees C. After amplification, the amplified DNA fragment was purified and was confirmed to be a length of 140 bp by using an Agilent Bioanalyzer 2100 DNA kit (Agilent Technologies, Inc., Palo Alto, Calif.).

Charged polymer: Heparin sulfate (Sigma-Aldrich)

Migration Shift Assays:

Serum sample was diluted 1:10 with the sample buffer containing no heparin sulfate (FIG. 4) and 0.05% heparin sulfate (FIGS. 5A-B and 6A-B, respectively), and mixed on chip (using a microfluidic chip 20 similar to that shown in FIG. 2) with labeled anti-AFP antibody-DNA conjugate. The conjugate complex was formed during 1 min incubation on the chip (e.g., in incubation channel 24 of chip 20 of FIG. 2). Following incubation (e.g., in incubation channel 24 of microfluidic chip 20 of FIG. 2), the resultant mixture was electrophoretically stacked, and injected into the separation channel (e.g., separation channel 25 of chip 20 of FIG. 2) filled with pDMA polymer containing no heparin sulfate (FIG. 4), 0.1% heparin sulfate (FIG. 5), and 1% heparin sulfate (FIG. 6), respectively. Voltage was applied to separation channel 25 of chip 20 of FIG. 2 to separate the free conjugate and the complex with different mobilities. Heparin sulfate in the sample buffer and the gel acted to prevent nonspecific binding of serum components to the DNA portion of the conjugate, and also acted for blocking serum interference in the gel during the separation. For example, FIG. 4 shows a migration shift chart of an alpha-feto protein assay in a separation media between conjugate peak 40 (e.g., DNA-antibody-alexa dye conjugate) (e.g., without serum) and 40' (e.g., with 10% serum) and conjugate/AFP complex peak 42 (without serum) and 42' (with 10% serum) with no charged polymer (e.g., heparin sulfate) in the sample or separation media (e.g., gel).

Figure 4:
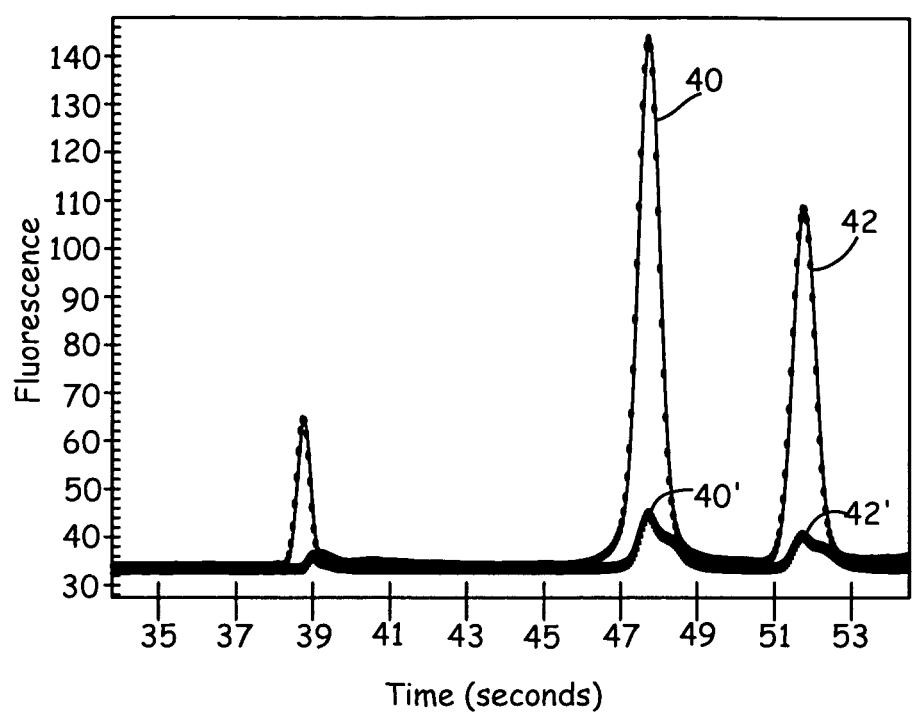
FIG. 4 shows a migration shift chart of an alpha-feto protein assay with no charged polymer (e.g., heparin sulfate) in the sample or separation media (e.g., gel) obtained in Example 1.
Figure 5A:
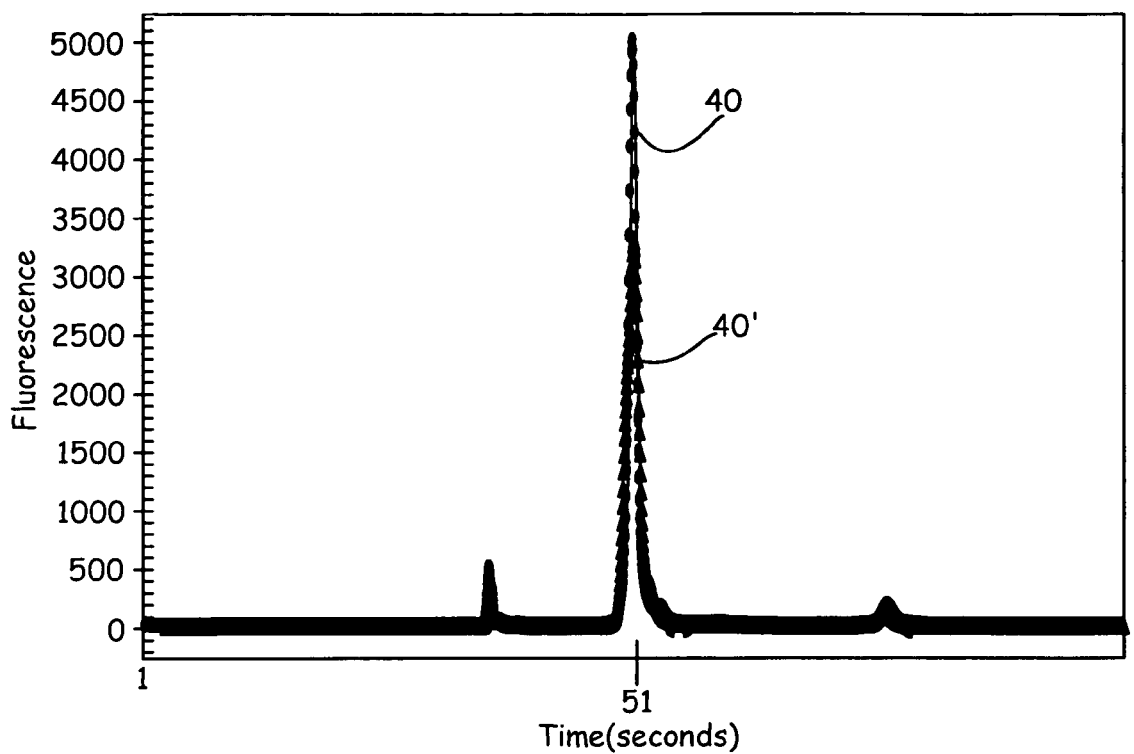
FIG. 5A shows a migration shift chart of an alpha-feto protein assay with 0.05% heparin in the sample and 0.1% heparin in the separation media.
Figure 5B:
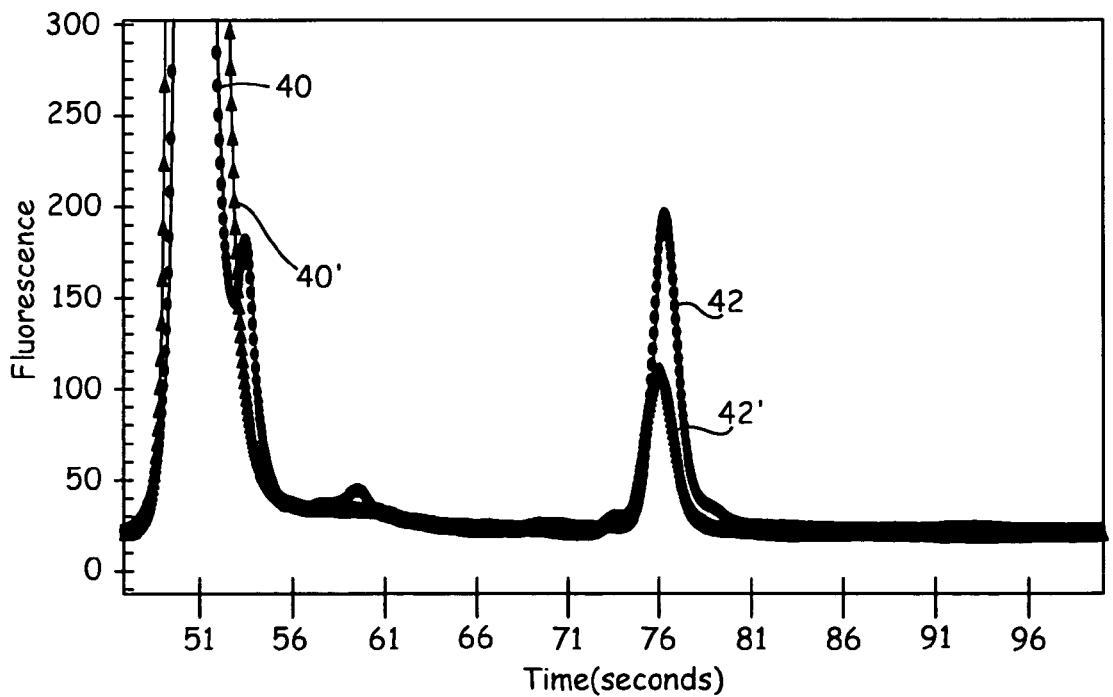
FIG. 5B is an exploded view of a portion of the chart of FIG. 5A obtained in Example 1.
Figure 6A:
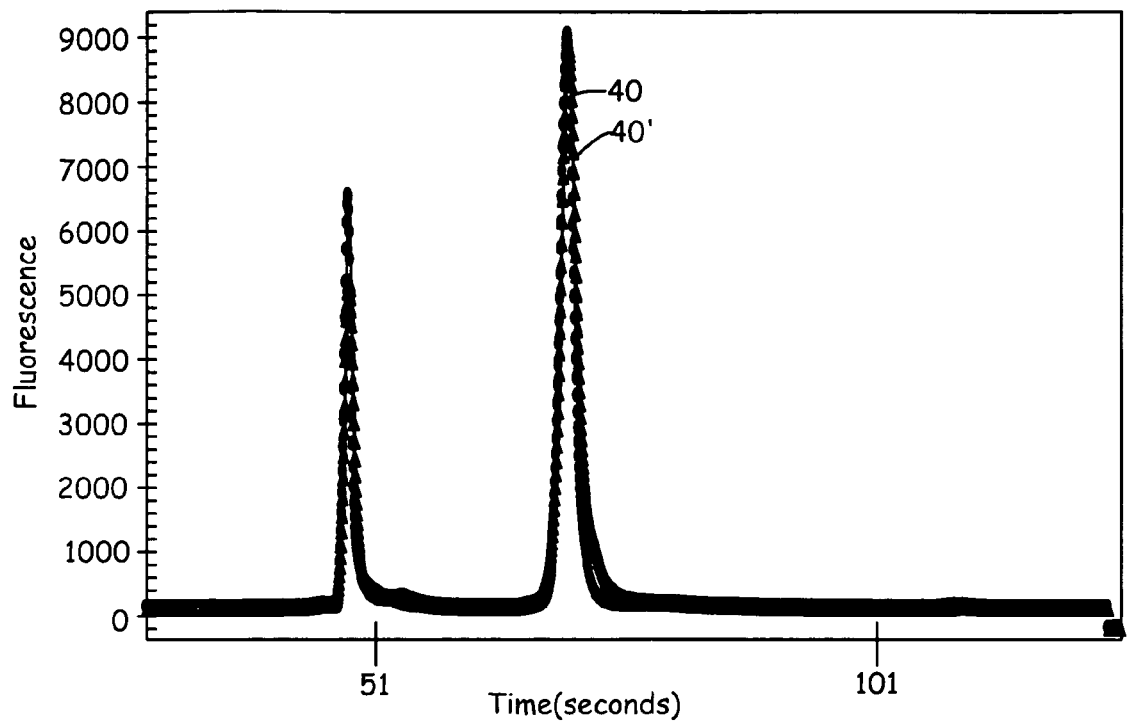
FIG. 6A shows a migration shift chart of an alpha-feto protein assay with 0.05% heparin in the sample and 1% heparin in the separation media.
Figure 6B:
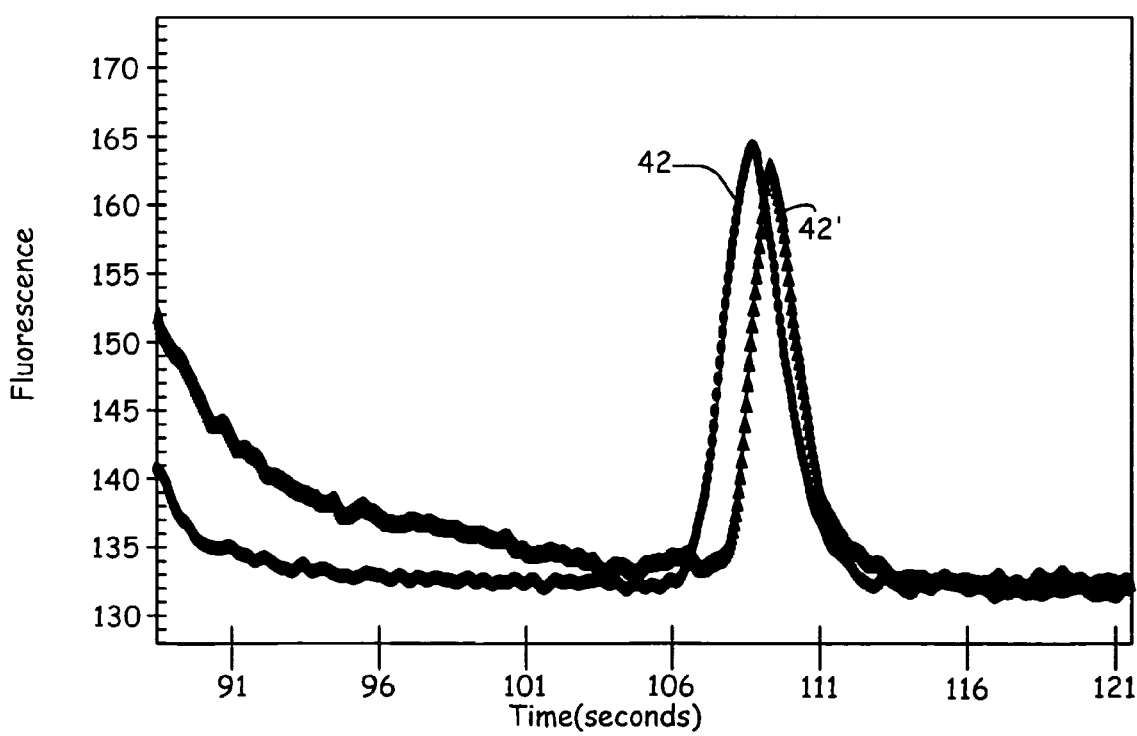
FIG. 6B is an exploded view of a portion of the chart of FIG. 6A obtained in Example 1.

When serum was added to the sample, interfering constituents change the retention time, height, and area of complex peak 40 and 42, as shown by reference numerals 40' and 42' in FIG. 4. Addition of charged polymer (e.g., heparin sulfate) to the assay can reduce the interfering changes, as shown in FIGS. 5A-B and 6A-B. FIGS. 5A-B show a migration shift chart of an alpha-feto protein assay with 0.05% heparin sulfate in the sample and 0.1% heparin sulfate in the separation media, showing the effect of heparin sulfate in reducing interference with detecting by binding to sample constituents which bind non-specifically to the DNA polymer (e.g., showing about 60% recovery of AFP from the serum sample). FIGS. 6A-B show a migration shift chart of an alpha-feto protein assay with 0.05% heparin sulfate in the sample and 1% heparin sulfate in the separation media, showing approximately 100% recovery of AFP from the serum sample as shown by the approximately overlying conjugate peaks 40 and 40' and AFP/conjugate complex peaks 42 and 42', respectively. Thus, the addition of heparin sulfate as a charged polymer to the separation media and sample buffer has a profound effect in reducing interference with analyte detection by binding to sample constituents which bind non-specifically to the carrier molecule.

Example 2

The following non-limiting Example illustrates the use of ITP in an AFP assay with serum, and an example of an electrophoregram showing the results with 5% serum with and without 0.01% Poly dI-dC. In this Example, poly(dI-dC) was used instead of heparin sulfate as a charged polymer to remove serum interference. The concentration of poly(dI-dC) was approximately 0.01% (w/v).

Leading buffer: 15 mM Tris/50 mM NaCl/0.9% pDMA/ 0.05% Tween-20/0.01% BSA

Trailing buffer: 15 mM Tris/25 mM HEPES/0.9% pDMA/ 0.05% Tween-20/0.01% BSA

Sample in a leading buffer with 10% serum and 100 nM anti-AFP monoclonal antibody WA-2 IgG, 100 ug/ml poly (dIdC). The monoclonal antibody was prepared in house (H. Katoh et al., Anal. Chem. (1998) 70, 2110-2114).

Binding reaction was performed off chip, by mixing a sample with Ab solution 1:1.

Labeled anti-AFP antibody/DNA conjugate: 500 pM of 2Alexa Fluor 647 anti-AFP monoclonal antibody WA-1-140 bp DNA conjugate; Alexa Fluor 647 dye was purchased from Molecular Probes, Inc. (Eugene, Oreg.), and the DNA charged carrier molecule was prepared by PCR reaction. The anti-AFP monoclonal antibody WA-1 recognizes a different epitope of AFP from WA-2. The conjugate was prepared according to the methods described in Japanese Patent Application number WO 02/082083 which has previously been incorporated by reference herein. The monoclonal antibody was prepared in house (H. Katoh et al, Anal. Chem. (1998) 70, 2110-2114). The 140 bp DNA was prepared as follows: PCR reaction was carried out by employing a synthesized sequence of 5'-GGTTAGCAACTTACTACCG-GATTTTG-3' as a forward primer, a synthesized sequence of 5'-CCTAGCAAACTCGGAAGATTTTTTCAGA-3' as a reverse primer and lambda DNA (from New England Bio Labs, Inc., Beverly, Mass.) as a template. The annealing temperature was 60 degrees C. After amplification, the amplified DNA fragment was purified and was confirmed to be a length of 140 bp by using an Agilent Bioanalyzer 2100 DNA kit (Agilent Technologies, Inc., Palo Alto, Calif.).

Charged polymer: Poly (dI-dC) (Sigma-Aldrich).

Figure 7A:
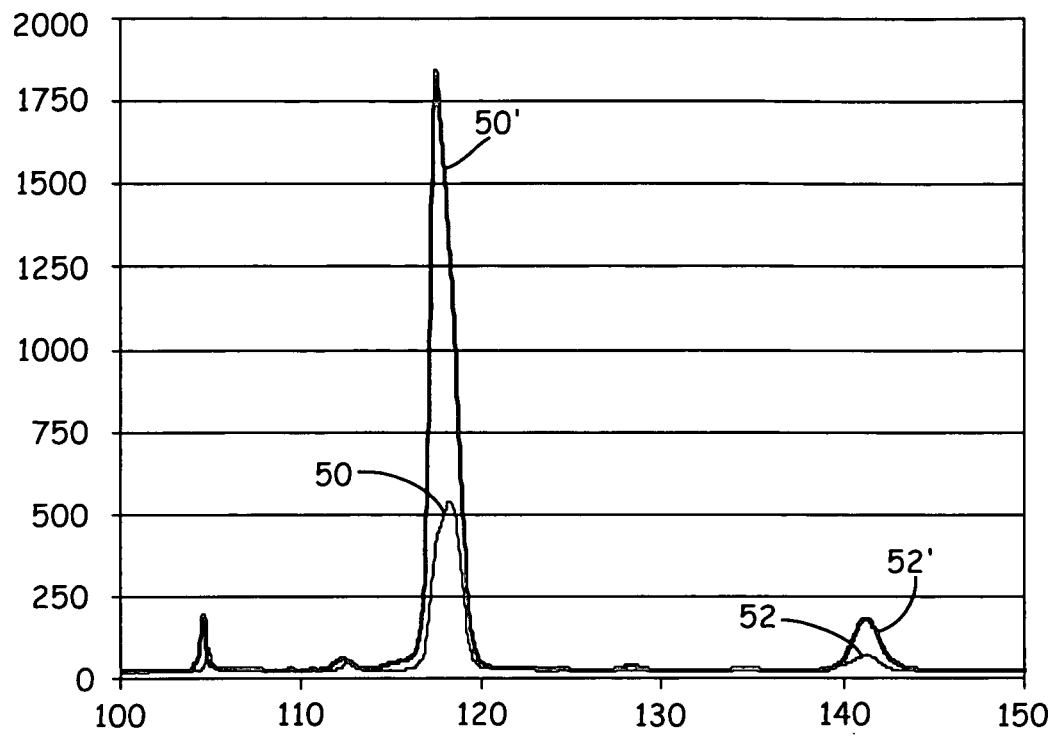
FIG. 7A shows a migration shift chart of an alpha-feto protein assay with 5% serum and with and without 0.01% Poly dI-dC.
Figure 7B:
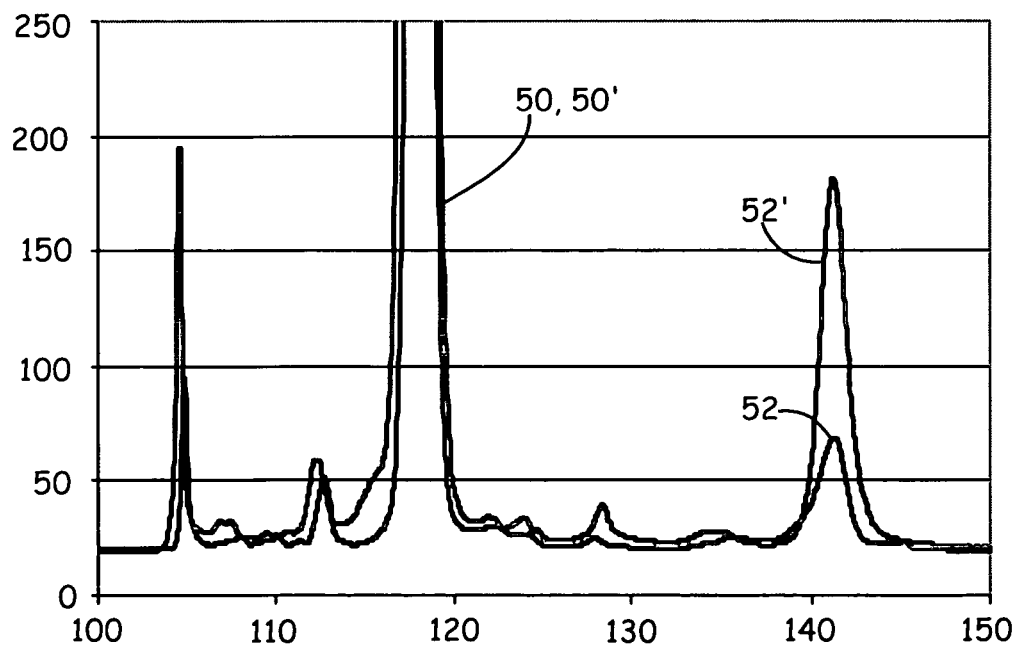
FIG. 7B is an exploded view of a portion of the chart of FIG. 7A obtained in Example 2.

FIGS. 7A-B show migration shift charts of relative fluorescence (Y-axis) versus time (X-axis) of an alpha-feto protein assay performed in a separation media in a separation channel of a microfluidic device similar to that used in Example 1 above between conjugate peak 50 (e.g., DNA-antibody-alexa dye conjugate) (with 5% serum and no Poly dI-dC) and 50' (with 5% serum and approximately 0.01% Poly dI-dC) and conjugate/AFP complex peak 52 (with 5% serum and no Poly dI-dC) and 52' (with 5% serum and approximately 0.01% Poly dI-dC). As shown in FIGS. 7A-B, addition of charged polymer (e.g., Poly dI-dC) to the assay can reduce interference with detecting by binding to sample constituents which bind non-specifically to the DNA polymer (e.g., showing about 60% recovery of AFP from the serum sample). The use of the ITP technique can increase the sensitivity of the assay (e.g., as shown by the relative peak height in the figures) by approximately 100 times or more over a conventional capillary electrophoresis assay that does not employ a sample concentration or stacking technique.

Example 3

The following non-limiting Example illustrates the use of DNA as the charged carrier molecule for concentrating a CA19-9 sample.

Leading buffer: 15 mM Tris/50 mM NaCl/0.2% pDMA/ 0.05% Tween-20/0.01% BSA

Trailing buffer: 15 mM Tris/25 mM HEPES/0.2% pDMA/ 0.05% Tween-20/0.01% BSA

Labeled anti-CA19-9 antibody: anti-CA19-9 monoclonal antibody (IgG) (Biodesign international) was labeled with Alexa by mixing the antibody and Alexa647 succinimide (Molecular probes, Inc., Eugene, Oreg., USA) in 0.2M Sodium bicarbonate buffer (pH8.3) for 2 hours, and then unbound Alexa dye was removed from the mixture by applying the reaction mixture to Gel filtration and DEAE-ion exchange chromatography.

Anti-CA19-9 antibody/DNA conjugate: conjugate of anti-CA19-9 monoclonal antibody (IgG) (Biodesign international) and 250 bp DNA was prepared according to the methods described in Japanese Patent Application number WO 02/082083. The 250 bp DNA was prepared as follows: PCR reaction was carried out by employing a synthesized sequence of sequence 5'-ATCTATGACTGTACGCCACT-GTCCCTAG-3' as a forward primer which has a NH$_2$ group at the 5' end, a synthesized sequence of 5'-CCTAG-CAAACTCGGAAGATTTTTTCAGA-3' as a reverse primer and lambda DNA (from New England Bio Labs, Inc., Beverly, Mass.) as a template. The annealing temperature was 60 degrees C. After amplification, the amplified DNA fragment was purified and was confirmed to be a length of 250 bp by using an Agilent Bioanalyzer 2100 DNA kit (Agilent Technologies, Inc., Palo Alto, Calif.).

Sample: the labeled anti-CA19-9 antibody (no. CA19-9), the mixture containing the complex of the labeled anti-CA19-9 antibody and the CA19-9, and the mixture containing the complex of the Anti-CA19-9 antibody/DNA conjugate, the CA19-9 and the labeled anti-CA19-9 antibody, which were obtained by the method described below, were used as a sample.

Labeled anti-CA19-9 antibody (no. CA19-9): 2 nM of purified Alexa-labeled anti-CA19-9.

The mixture containing the complex of the labeled anti-CA19-9 antibody and the CA19-9: 2 nM of purified Alexa-labeled anti-CA19-9 was mixed with 1000 U/mL of CA19-9 (Biodesign international) and the mixture was held at room temperature for 30 min to generate antigen-antibody complex. The mixture containing the complex of the Anti-CA19-9 antibody/DNA conjugate, the CA19-9 antigen and the labeled anti-CA19-9 antibody: the prepared anti-CA19-9 antibody/DNA conjugate was mixed with various concentrations (0, 10 or 100 U/mL) of CA19-9 and 2 nM of Alexa-labeled anti-CA19-9 antibody, and the mixture was incubated at room temperature for 30 min.

Figure 12A:
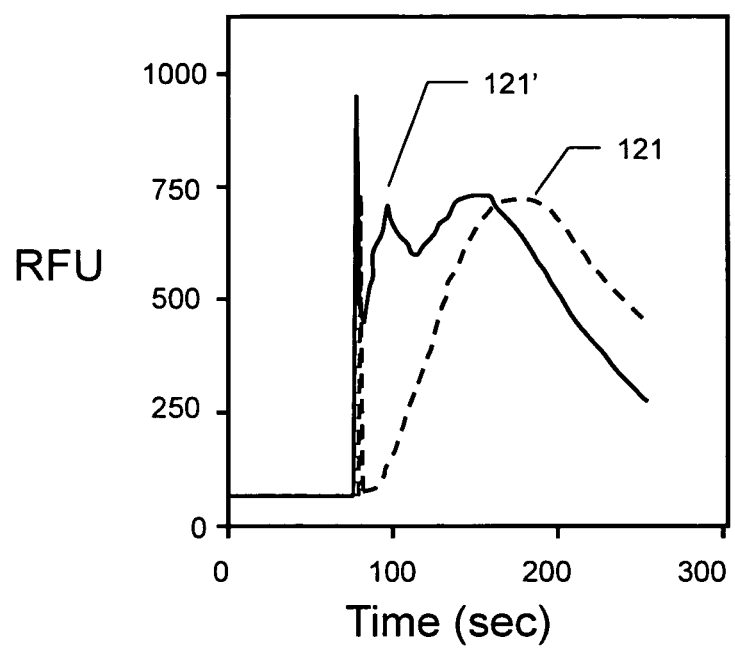
FIG. 12A shows a migration shift chart of CA19-9 concentration using a sample of labeled anti-CA19-9 antibody (no. CA19-9) or a sample of a mixture of the labeled anti-CA19-9 antibody and CA19-9 obtained in Example 3.
Figure 12B:
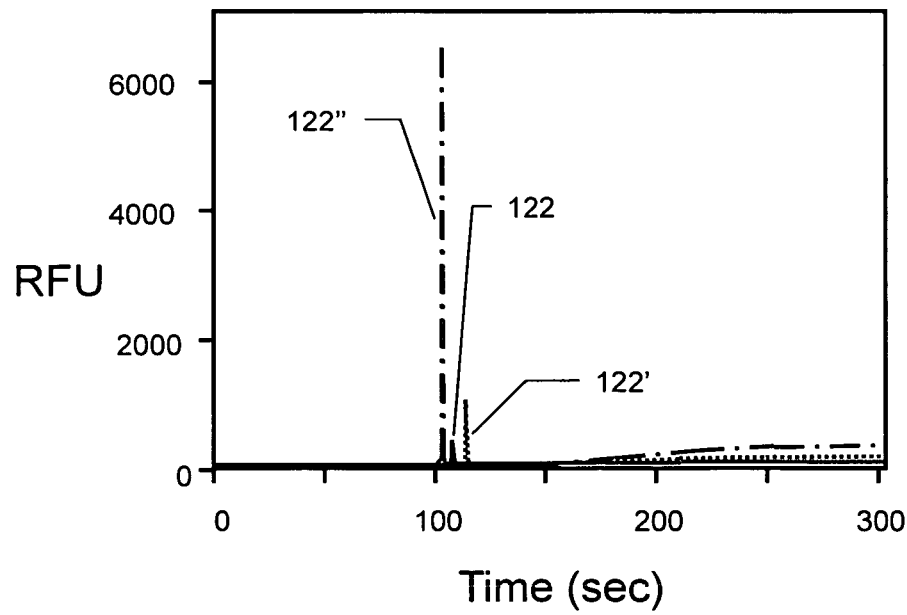
FIG. 12B shows a migration shift chart of CA19-9 concentration using a mixture of labeled anti-CA19-9 antibody, DNA-labeled anti-CA19-9 antibody and various concentrations of A CA19-9 (0, 10 or 100 U/mL) obtained in Example 3.

Concentration Procedure: The sample was then applied to a loading channel which is fluidically connected to a concentration channel which was downstream of the loading channel and was filled with leading buffer and a trailing buffer channel which was upstream of the concentration channel and filled with trailing buffer. After the loading channel was filled with the sample, an electrical field was applied and concentration was conducted according to ITP principles. FIGS. 12A-B show migration shift charts of relative fluorescence (Y-axis) versus time (X-axis) of a CA19-9 concentration performed in a concentration channel of a microfluidic device.

FIG. 12A shows the results from experiments with the labeled anti-CA19-9 antibody (no CA19-9) (labeled antibody peak 121: e.g., labeled anti-CA19-9 antibody) and with a mixture of the labeled anti-CA19-9 antibody and CA19-9 (labeled antibody/antigen complex peak 121': e.g., complex of the labeled anti-CA19-9 antibody and the CA19-9 antigen).

FIG. 12B shows the results from a mixture of the labeled anti-CA19-9 antibody, the DNA-labeled anti-CA19-9 antibody and CA19-9 (conjugate/antigen/labeled antibody peak 122: e.g., conjugate of anti-CA19-9 antibody and DNA/CA19-9 antigen/labeled anti-CA19-9 antibody obtained by using 0 U/mL of CA19-9); conjugate/antigen/labeled antibody peak 122': e.g., conjugate of anti-CA19-9 antibody and DNA/CA19-9 antigen/labeled anti-CA19-9 antibody obtained by using 10 U/mL of CA19-9; and conjugate/antigen/labeled antibody peak 122": e.g., conjugate of anti-CA19-9 antibody and DNA/CA19-9 antigen/labeled anti-CA19-9 antibody obtained by using 100 U/mL of CA19-9).

As shown in FIG. 12A, the complex of the objective substance (e.g., CA19-9) and the affinity molecule (e.g., the labeled anti-CA19-9 antibody) migrated a little faster than the free (unbound) affinity molecule but was not concentrated. On the other hand, as shown in FIG. 12B, the complex of the objective substance (e.g., CA19-9 antigen), the affinity molecule (e.g. Alexa-labeled anti-CA19-9 antibody), and the conjugate of the affinity molecule and the charged carrier molecule (e.g., the anti-CA19-9 antibody/DNA conjugate) was concentrated very effectively, resulting in a very sharp peak of the complex. Further, the peak was well correlated to CA19-9 antigen concentrations. That is, the use of the charged carrier molecule (e.g., DNA) in the concentration step can concentrate the objective substance into very high concentration.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting an analyte of interest in a sample, comprising:
   (i) contacting
      (a) a first polyanion;
      (b) the sample containing the analyte, wherein the sample is a serum, a plasma, a whole blood, a sputum specimen, a stool specimen, a cerebral spinal fluid, a urine sample, a uro-genital swab, a synovial fluid, or a lymph fluid sample; and
      (c) one or more affinity molecule/charged carrier molecule conjugates to form a complex of the analyte and the one or more conjugates,
   wherein each affinity molecule has an affinity against the analyte, each charged carrier molecule has a net negative charge, and the charged carrier molecule causes a change in a separation property of the analyte by binding to the analyte through the affinity molecule to form a complex of the analyte and the affinity molecule/charged carrier molecule conjugate;
   (ii) using a concentration medium containing a second polyanion, concentrating the complex in a concentration channel in a microfluidic device, the concentration channel having at least one microscale dimension of between about 0.1 and about 500 microns;
   (iii) using a separation medium containing a third polyanion, electrophoretically separating the complex from any unbound conjugate in a separation channel in a microfluidic device, the separation channel having at least one microscale dimension of between about 0.1 and about 500 microns; and
   (iv) detecting the complex to identify the presence of the analyte or to determine an amount of the analyte in the sample,
   wherein the first, second, and third polyanions reduce binding of the sample's constituents to the affinity molecule, the charged carrier molecule, or the complex and reduce interference with separating the complex.

2. The method of claim 1, wherein the first, second, and third polyanions are independently selected from one or more of polysaccharides, polynucleotides, polypeptides, synthetic macromolecular compounds, or ceramics; or a mixture thereof.

3. The method of claim 1, wherein the first, second, and third polyanions are independently selected from one or more of poly-dIdC, heparin sulfate, dextran sulfate, polytungstic acid, polyanethole sulfonic acid, polyvinyl sulfate, polyacrylate, chondroitin sulfate, plasmid DNA, calf thymus DNA, salmon sperm DNA, DNA coupled to cellulose, glass particles, colloidal glass, or glass milk, or a mixture thereof.

4. The method of claim 1, wherein the first, second and/or third polyanion comprises heparin sulfate.

5. The method of claim 1, wherein at least one of the one or more affinity molecules is labeled with a detectable marker.

6. The method of claim 1, wherein the contacting step further comprises contacting the sample with one or more non-conjugated affinity molecules, wherein each non-conjugated affinity molecule has an affinity against the analyte, to form a complex of the analyte, the at least one conjugate, and the at least one non-conjugated affinity molecule.

7. The method of claim 1, wherein the conjugated affinity molecules bind to the analyte by an interaction selected from a protein-protein interaction, a protein-chemical interaction, or a chemical-chemical interaction.

8. The method of claim 6, wherein the conjugated and the non-conjugated affinity molecules bind to the analyte by an interaction selected from an antigen-antibody interaction, a sugar chain-lectin interaction, an enzyme-inhibitor interaction, a protein-peptide chain interaction, a chromosome or nucleotide chain-nucleotide chain interaction, a nucleotide-ligand interaction, or a receptor-ligand interaction.

9. The method of claim 6, wherein the conjugated and the non-conjugated affinity molecule are selected from one or more of an antibody, an Fab, F(ab')$_2$ or Fab' fragment of an antibody, an antibody variable region, a lectin, avidin, a receptor, an affinity peptide, an aptamer, or a DNA binding protein.

10. The method of claim 1, wherein the charged carrier molecule is an anionic molecule.

11. The method of claim 10, wherein the charged carrier molecule is an anionic molecule selected from a nucleotide chain or a sulfonated polypeptide.

12. The method of claim 1, wherein the charged carrier molecule comprises DNA, RNA, an anionic polymer, or a sulfonated polypeptide.

13. The method of claim 12, wherein the charged carrier molecule comprises DNA comprising one or more synthetic sequences.

14. The method of claim 13, wherein the one or more synthetic sequences comprise one or more nucleotide analogs comprising a linker group or a linker reactive group.

15. The method of claim 14, wherein the linker group or linker reactive group is selected from an amino group, a thiol, a carboxyl group, an imidazol group, or a succinimide group.

16. The method of claim 15, further comprising covalently bonding a detectable marker to the linker group or linker reactive group.

17. The method of claim 1, wherein at least one of the one or more charged carrier molecules is labeled with a detectable marker.

18. The method of claim 6, wherein at least one conjugate or at least one non-conjugated affinity molecule is labeled with a detectable marker.

19. The method of claim 6, wherein at least one conjugate is labeled by a detectable marker.

20. The method of claim 6, wherein the charged carrier molecule in at least one conjugate is labeled by a detectable marker.

21. The method of claim 6, wherein the affinity molecule in at least one conjugate is labeled by a detectable marker.

22. The method of claim 5, 16, 17, 18, 19, 20 or 21, wherein the detectable marker is selected from one or more of a fluorescent dye, a luminescent dye, a phosphorescent dye, a fluorescent protein, a luminescent protein or particle, a radioactive tracer, a chemiluminescent compound, a redox mediator, an electrogenic compound, an enzyme, a colloidal gold particle, or a silver particle.

23. The method of claim 1, wherein the separation media comprises one or more of a size exclusion resin, a polyacrylamide gel, polyethylene glycol (PEG), polyethyleneoxide (PEO), a co-polymer of sucrose and epichlorohydrin, polyvinylpyrrolidone (PVP), hydroxyethylcellulose (HEC), poly-N,N-dimethylacrylamide (PDMA), or an agarose gel.

24. The method of claim 1, wherein the third polyanion is present in the separation media at a concentration of between about 0.01 to 5% (w/v).

25. The method of claim 1, wherein the third polyanion is present in the separation media at a concentration of between about 0.05 to 2% (w/v).

26. The method of claim 1, wherein the separation channel has at least one cross-sectional microscale dimension of between about 0.1 and 200 microns.

27. The method of claim 1, wherein:
at least one of the one or more conjugates is labeled by a detectable marker;
step (iii) comprises electrophoretically separating the complex from the at least one conjugate labeled by the detectable marker that is not involved in forming the complex; and
step (iv) comprises:
  (a) measuring an amount of the separated complex or detecting a presence of the separated complex; and
  (b) determining an amount of the analyte in the sample on the basis of the measured amount or identifying a presence of the analyte in the sample on the basis of the detected presence.

28. The method of claim 6, wherein:
either at least one of the non-conjugated affinity molecules or at least one of the conjugates is labeled by a detectable marker;
step (iii) comprises electrophoretically separating the complex from any free non-conjugated affinity molecule labeled by the detectable marker or any free conjugate labeled by the detectable marker; and
step (iv) comprises:
  (a) measuring an amount of the separated complex or detecting a presence of the separated complex; and
  (b) determining an amount of the analyte in the sample on the basis of the measured amount or identifying a presence of the analyte in the sample on the basis of the detected presence.

29. A method for determining an analyte in a sample, the method comprising:
(i) contacting
  (a) a first polyanion;
  (b) the sample containing the analyte, wherein the sample is a serum, a plasma, a whole blood, a sputum specimen, a stool specimen, a cerebral spinal fluid, a urine sample, a uro-genital swab, a synovial fluid, or a lymph fluid sample;
  (c) either a labeled analyte formed by labeling analyte extrinsic to the sample with a detectable marker or a labeled analogue of the analyte formed by labeling an analogue with a detectable marker, and
  (d) one or more affinity molecule/charged carrier molecule conjugates, thereby forming a first complex of the analyte in the sample and the one or more conjugates and a second complex of either the labeled analyte and the one or more conjugates or the labeled analogue and the one or more conjugates;
wherein the affinity molecule in each conjugate has an affinity against the analyte in the sample and the labeled analyte, or an affinity against the analyte in the sample and the labeled analogue, and wherein each charged carrier molecule has a net negative charge, and the charged carrier molecule causes a change in a separation property of the analyte or the analogue by binding to the analyte or the analogue through the affinity molecule to form a complex of the analyte or the analogue, with the affinity molecule/charged carrier molecule conjugate;
(ii) using a concentration medium containing a second polyanion, concentrating the second complex in a concentration channel in a microfluidic device, the concentration channel having at least one microscale dimension of between about 0.1 and about 500 microns;
(iii) using a separation medium containing a third polyanion, electrophoretically separating the second complex from any free labeled analyte or free labeled analogue in a separation channel in a microfluidic device, the separation channel having at least one microscale dimension of between about 0.1 and about 500 microns;
(iv) measuring an amount of the separated second complex or an amount of the separated free labeled analyte or the separated free labeled analogue; and
(v) determining an amount of the analyte in the sample on the basis of the measured amount;
wherein the first, second, and third polyanions reduce binding of the sample's constituents to the affinity molecule, the charged carrier molecule, or the complex and reduce interference with the determination.

30. The method of claim 28, wherein:
step (i) comprises contacting
  (a) the first polyanion,
  (b) the sample containing the analyte,
  (c) either the labeled analyte or the labeled analogue,
  (d) the one or more conjugates, and
  (e) one or more non-conjugated affinity molecules,
wherein each of the conjugated and non-conjugated affinity molecules have an affinity against the analyte in the complex sample and the labeled analyte or the analyte in the complex sample and the labeled analogue, thereby forming a first complex of the analyte in the complex sample, the non-conjugated affinity molecule, and the conjugate, and a second complex of either the labeled analyte, the non-conjugated affinity molecule, and the conjugate, or the labeled analogue, the non-conjugated affinity molecule, and the conjugate;
step (iii) comprises electrophoretically separating the second complex from any free labeled analyte or free labeled analogue;
step (iv) comprises measuring an amount of the separated second complex or an amount of the separated free labeled analyte or the separated free labeled analogue; and
step (v) comprises determining an amount of the analyte in the complex sample on the basis of the measured amount.

31. A method for determining an analyte in a sample, the method comprising:
(i) contacting
  (a) a first polyanion;
  (b) the sample containing the analyte, wherein the sample is a serum, a plasma, a whole blood, a sputum specimen, a stool specimen, a cerebral spinal fluid, a urine sample, a uro-genital swab, a synovial fluid, or a lymph fluid, sample;
  (c) either a charged carrier molecule-bound analyte formed by binding analyte extrinsic to the sample to a charged carrier molecule or a charged carrier molecule-bound analogue formed by binding an analogue of the analyte to a charged carrier molecule, and
  (d) an affinity molecule labeled by a detectable marker, thereby forming a first complex of either the charged carrier molecule-bound analyte and the labeled affinity molecule or the charged carrier molecule-bound analogue and the labeled affinity molecule and a second complex of the analyte in the sample and the labeled affinity molecule,
wherein the affinity molecule has an affinity against the analyte in the sample and the charged carrier molecule-bound analyte or the analyte in the sample and the charged carrier molecule-bound analogue, the charged carrier molecule has a net negative charge, and the charged carrier molecule has a property capable of causing a change in a separation property of the first complex;

(ii) using a concentration medium containing a second polyanion, concentrating the first complex in a concentration channel in a microfluidic device, the concentration channel having at least one microscale dimension of between about 0.1 and about 500 microns;

(iii) using a separation medium containing a third polyanion, electrophoretically separating the first complex from any second complex in a separation channel in a microfluidic device, the separation channel having at least one microscale dimension of between about 0.1 and about 500 microns;

(iv) measuring an amount of the separated first complex or an amount of the separated second complex; and (v) determining an amount of the analyte in the sample on the basis of the measured amount;

wherein the first, second, and third polyanions reduce binding of the sample's constituents to the affinity molecule, the charged carrier molecule, or the complex and reduce interference with the determination.

32. The method of claim 1, wherein the sample is selected from a serum, a plasma, a whole blood, or a urine sample.

33. The method of claim 1, wherein the analyte is one or more selected from alpha feto protein (AFP), human chorionic gonadotropin (hCG), thyroid-stimulating hormone (TSH), follicle-stimulating hormone (FSH), luteinizing hormone (LH), interleukin, Fas ligand, cancer antigen 19-9 (CA19-9), cancer antigen 125 (CA125), prostate specific antigen (PSA), hepatitis B virus antigen (HBsAg), anti-HIV antibody, or thyroxine (T4).

34. The method of claim 1, wherein contacting the sample containing the analyte with one or more conjugates to form a complex of the analyte and the conjugate is conducted in a microchannel fluidically connected to the concentration channel.

35. The method of claim 1, wherein concentrating the complex is conducted according to a concentration method selected from field amplification sample stacking (FASS), field amplification sample injection (FASI), isotachophoresis (ITP), isoelectric focusing (IF), or solid phase extraction (SPE).

36. The method of claim 1, wherein concentrating the complex is conducted according to a concentration method selected from field amplification sample stacking (FASS), or isotachophoresis (ITP).

37. The method of claim 1, wherein the charged carrier molecule comprises DNA comprising one or more synthetic sequences, wherein the one or more synthetic sequences comprises one or more nucleotides selected from a phosphorothioate analog of nucleotide, a nucleotide that contains a methylene group in the place of the oxygen in the ribose ring, or a nucleotide in which a replacement for the 2'-sugar deoxy substituent is selected from a 2'-fluoro, 2'-O-methyl, 2-O-alkoxyl, or 2'-O-allyl modification.

38. The method of claim 1, wherein the concentration media comprises one or more of a size exclusion resin, a polyacrylamide gel, polyethylene glycol (PEG), polyethyleneoxide (PEO), a co-polymer of sucrose and epichlorohydrin, polyvinylpyrrolidone (PVP), hydroxyethylcellulose (HEC), poly-N,N-dimethylacrylamide (PDMA), or an agarose gel.

39. The method of claim 1, wherein the second polyanion is added to the concentration media at a concentration of between about 0.01 to 5% (w/v).

40. The method of claim 1, wherein the second polyanion is added to the concentration media at a concentration of between about 0.05 to 2% (w/v).

41. The method of claim 1, wherein the first polyanion comprises heparin sulfate which is present at a concentration of between about 0.001 to 2% (w/v).

42. The method of claim 1, wherein the concentration channel has at least one cross-sectional microscale dimension of between about 0.1 and 200 microns.

43. The method of claim 1 or 27, wherein two or more conjugates are used, and wherein each affinity molecule in the two or more conjugates has a property capable of binding with the analyte at a different site on the analyte from every other affinity molecule.

44. The method of claim 6 or 28, wherein each conjugated and non-conjugated affinity molecule has a property capable of binding with the analyte at a different site on the analyte from every other affinity molecule.

45. The method of claim 29, wherein two or more conjugates are used, and wherein each affinity molecule in the two or more conjugates has a property capable of binding with the analyte in the sample and the labeled analyte at a different site on the analyte in the sample and a different site on the labeled analyte from every other affinity molecule, or each affinity molecule in the conjugate has a property capable of binding with the analyte in the sample and the labeled analogue at a different site on the analyte in the sample and a different site on the labeled analogue from every other affinity molecule.

46. The method of claim 30, wherein two or more affinity molecules are used, and wherein each affinity molecule has a property capable of binding with the analyte in the sample and the labeled analyte at a different site on the analyte in the sample and a different site on the labeled analyte from every other affinity molecule, or each affinity molecule has a property capable of binding with the analyte in the sample and the labeled analogue at a different site on the analyte in the sample and a different site on the labeled analogue from every other affinity molecule.

47. The method of claim 31, wherein two or more affinity molecules are used, and wherein each affinity molecule has a property capable of binding with the analyte in the sample and the charged carrier molecule-bound analyte at a different site on the analyte in the sample and a different site on the charged carrier molecule-bound analyte from every other affinity molecule, or each affinity molecule has a property capable of binding with the analyte in the sample and the charged carrier molecule-bound analogue at a different site on the analyte in the sample and a different site on the charged carrier molecule-bound analogue from every other affinity molecule.

48. The method of claim 1, wherein the step (i) further comprises:
adding the first polyanion to a solution containing the sample containing the analyte; and
contacting the solution and the one or more conjugates to form a complex of the analyte and the one or more conjugates in the presence of the first polyanion.

49. The method of claim 1, wherein the step (i) further comprises:
adding the first polyanion to a solution containing the one or more conjugates; and
contacting the solution and the sample containing the analyte to form a complex of the analyte and the one or more conjugates in the presence of the first polyanion.

50. The method of claim 6, wherein the step (i) further comprises:
adding the first polyanion to a solution containing the sample containing the analyte; and
contacting the solution and the one or more conjugates and the one or more non-conjugated affinity molecules to form a complex of the analyte, the at least one conjugate, and the at least one non-conjugated affinity molecule in the presence of the first polyanion.

51. The method of claim 6, wherein the step (i) further comprises:
adding the first polyanion to a solution containing the one or more conjugates and/or the one or more non-conjugated affinity molecules; and
contacting the solution and the sample containing the analyte and, if not present in the solution, the one or more conjugates or the one or more non-conjugated affinity molecules, to form a complex of the analyte, the at least one conjugate, and the at least one non-conjugated affinity molecule in the presence of the first polyanion.

52. The method of claim 27, wherein the step (i) further comprises:
adding the first polyanion to a solution containing the sample containing the analyte; and
contacting the solution and the one or more conjugates, wherein at least one of the one or more conjugates is labeled by a detectable marker, to form a complex containing the analyte and the at least one conjugate in the presence of the first polyanion.

53. The method of claim 27, wherein the step (i) further comprises:
adding the first polyanion to a solution containing the one or more conjugates, wherein at least one of the one or more conjugates is labeled by a detectable marker; and
contacting the solution and the sample containing the analyte to form a complex containing the analyte and the at least one conjugate in the presence of the first polyanion.

54. The method of claim 28, wherein the step (i) further comprises:
adding the first polyanion to a solution containing the sample containing the analyte; and
contacting the solution and the one or more conjugates and the one or more non-conjugated affinity molecules, wherein either at least one of the conjugates or at least one of the non-conjugated affinity molecules is labeled by a detectable marker, to form a complex containing the analyte, the at least one conjugate, and the at least one non-conjugated affinity molecule in the presence of the first polyanion.

55. The method of claim 28, wherein the step (i) further comprises:
adding the first polyanion to a solution containing the one or more conjugates and/or the one or more non-conjugated affinity molecules; and
contacting the solution and the sample containing the analyte and, if not present in the solution, with the one or more conjugates or the one or more non-conjugated affinity molecules, wherein either at least one of the conjugates or at least one of the non-conjugated affinity molecules is labeled by a detectable marker, to form a complex containing the analyte, the conjugate, and the non-conjugated affinity molecule in the presence of the first polyanion.

56. The method of claim 29, wherein the step (i) further comprises:
adding the first polyanion to a solution containing the sample containing the analyte; and
contacting the solution, either the labeled analyte or the labeled analogue, and the one or more conjugates to form the first complex and the second complex in the presence of the first polyanion.

57. The method of claim 29, wherein the step (i) further comprises:
adding the first polyanion to a solution containing the one or more conjugates; and
contacting the solution, the sample containing the analyte, and either the labeled analyte or the labeled analogue to form the first complex and the second complex in the presence of the first polyanion.

58. The method of claim 30, wherein the step (i) further comprises:
adding the first polyanion to a solution containing the sample containing the analyte; and
contacting the solution, either the labeled analyte or the labeled analogue, the one or more conjugates, and the one or more non-conjugated affinity molecules to form the first complex and the second complex in the presence of the first polyanion.

59. The method of claim 30, wherein the step (i) further comprises:
adding the first polyanion to a solution containing the one or more conjugates and/or the one or more non-conjugated affinity molecules; and
contacting the solution, the sample containing the analyte, either the labeled analyte or the labeled analogue, and, if not present in the solution, the one or more conjugates or the one or more non-conjugated affinity molecules, to form the first complex and the second complex in the presence of the first polyanion.

60. The method of claim 31, wherein the step (i) further comprises:
adding the first polyanion to a solution containing the sample containing the analyte; and
contacting the solution, either the charged carrier molecule-bound analyte or the charged carrier molecule-bound analogue, and the labeled affinity molecule to form the first complex and the second complex in the presence of the first polyanion.

61. The method of claim 31, wherein the step (i) further comprises:
adding the first polyanion to a solution containing the labeled affinity molecule; and
contacting the solution, the sample containing the analyte, and either the charged carrier molecule-bound analyte or the charged carrier molecule-bound analogue to form the first complex and the second complex in the presence of the first polyanion.

* * * * *

UNITED STATES PATENT AND TRADEMARK OFFICE
CERTIFICATE OF CORRECTION

PATENT NO. : 9,766,216 B2  
APPLICATION NO. : 10/821657  
DATED : September 19, 2017  
INVENTOR(S) : H. Garrett Wada et al.

Page 1 of 1

It is certified that error appears in the above-identified patent and that said Letters Patent is hereby corrected as shown below:

On the Title Page

Item (73), Assignees:
After "Wako Pure Chemical Industries, Ltd., Osaka (JP)" please add -- ; Caliper Life Sciences, Inc., Hopkinton, MA (US) --

Signed and Sealed this  
Seventh Day of August, 2018

Andrei Iancu  
*Director of the United States Patent and Trademark Office*